United States Patent
Bradbury et al.

(10) Patent No.: US 8,258,140 B2
(45) Date of Patent: Sep. 4, 2012

(54) CHEMICAL COMPOUNDS—643

(75) Inventors: Robert Hugh Bradbury, Macclesfield (GB); Gregory Richard Carr, Macclesfield (GB); Alfred Arthur Rabow, Macclesfield (GB); Srinivasa Rao Korupoju, Bangalore (IN); Harikrishna Tumma, Bangalore (IN)

(73) Assignee: Astrazeneca AB, Sodertalje (SE)

( * ) Notice: Subject to any disclaimer, the term of this patent is extended or adjusted under 35 U.S.C. 154(b) by 92 days.

(21) Appl. No.: 12/702,603

(22) Filed: Feb. 9, 2010

(65) Prior Publication Data
US 2010/0267699 A1 Oct. 21, 2010

Related U.S. Application Data

(60) Provisional application No. 61/187,766, filed on Jun. 17, 2009, provisional application No. 61/151,221, filed on Feb. 10, 2009.

(51) Int. Cl.
*A61K 31/501* (2006.01)
*C07D 237/02* (2006.01)

(52) U.S. Cl. .................. 514/255.01; 544/235; 544/238; 544/239

(58) Field of Classification Search .................. 544/235, 544/238, 239; 514/247, 255.01
See application file for complete search history.

(56) References Cited

U.S. PATENT DOCUMENTS

| | | | |
|---|---|---|---|
| 5,411,981 A | 5/1995 | Gaillard-Kelly et al. | |
| 5,627,201 A | 5/1997 | Gaillard-Kelly et al. | |
| RE35,956 E | 11/1998 | Gaillard-Kelly et al. | |
| 2004/0102360 A1 | 5/2004 | Barnett et al. | |
| 2006/0281750 A1 | 12/2006 | Li et al. | |
| 2010/0016279 A1 | 1/2010 | Bradbury et al. | |
| 2010/0292222 A1 | 11/2010 | Bradbury et al. | |
| 2010/0298315 A1 | 11/2010 | Albert et al. | |

FOREIGN PATENT DOCUMENTS

| | | |
|---|---|---|
| EP | 0580459 B1 | 1/1994 |
| FR | 2919870 A1 | 2/2009 |
| WO | 2001/016108 A1 | 3/2001 |
| WO | 2005040136 A1 | 5/2005 |
| WO | 2005/089118 A1 | 9/2005 |
| WO | 2006039325 A2 | 4/2006 |
| WO | 2007064797 A2 | 6/2007 |
| WO | 2007092727 A1 | 8/2007 |
| WO | 2007095423 A1 | 8/2007 |
| WO | 2007138472 A2 | 12/2007 |
| WO | 2008016192 A2 | 2/2008 |
| WO | 2008044033 A1 | 4/2008 |
| WO | 2008109104 A1 | 9/2008 |
| WO | 2009005675 A1 | 1/2009 |
| WO | 2009081197 A1 | 7/2009 |
| WO | 2010/131022 A1 | 11/2010 |

OTHER PUBLICATIONS

Vasaitis et. al. Androgen receptor inactivation contributes to antitumor efficacy of 17-hydroxylase/17,20-lyase inhibitor 3-hydroxy-17-(1H-benzimidazole-1-yl)androsta-5, 16-diene in prostate cancer; Molecular Cancer Therapeutics 2008;7(8), Aug. 2008; pp. 2348-2357.
U.S. Appl. No. 12/776,970, AstraZeneca AB, Unpublished US Application.
Cox et al, 'Discovery of 3-aminopiperidines as potent, selective and orally bioavailable dipeptidyl peptidase IV inhibitors', Bioorganic & Medicinal Chemistry Letters, 2007, pp. 4579-4583, vol. 17.
Joseph et al, 'Inhibition of prostate cancer cell growth by second-site androgen receptor antagonists', PNAS,2009, pp. 1-6, vol. 1.
English Language Abstract of French Patent Application Publication No. FR 2919870, (Aug. 9, 2007).
Bradbury et al, Small-molecule androgen receptor downregulators as an approach to treatment of advanced prostate cancer, Bioorganic & Medicinal Chemistry Letters, 2011, vol. 21, pp. 5442-5445.
Office action dated Sep. 3, 2010 relating to U.S. Appl. No. 12/338,405.

*Primary Examiner* — Paul V. Ward
(74) *Attorney, Agent, or Firm* — Astrazeneca AB

(57) ABSTRACT

The invention concerns bicyclic compounds of Formula I (I)

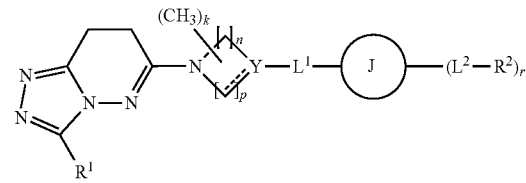

wherein $=\!=\!=\!=$, $R^1$, $R^2$, $L^1$, $L^2$, J, Y, k, n, p and r are as defined in the description. The present invention also relates to processes for the preparation of such compounds, pharmaceutical compositions containing them and their use in the treatment of androgen-receptor associated conditions, particularly prostate cancer.

8 Claims, 18 Drawing Sheets

Figure A
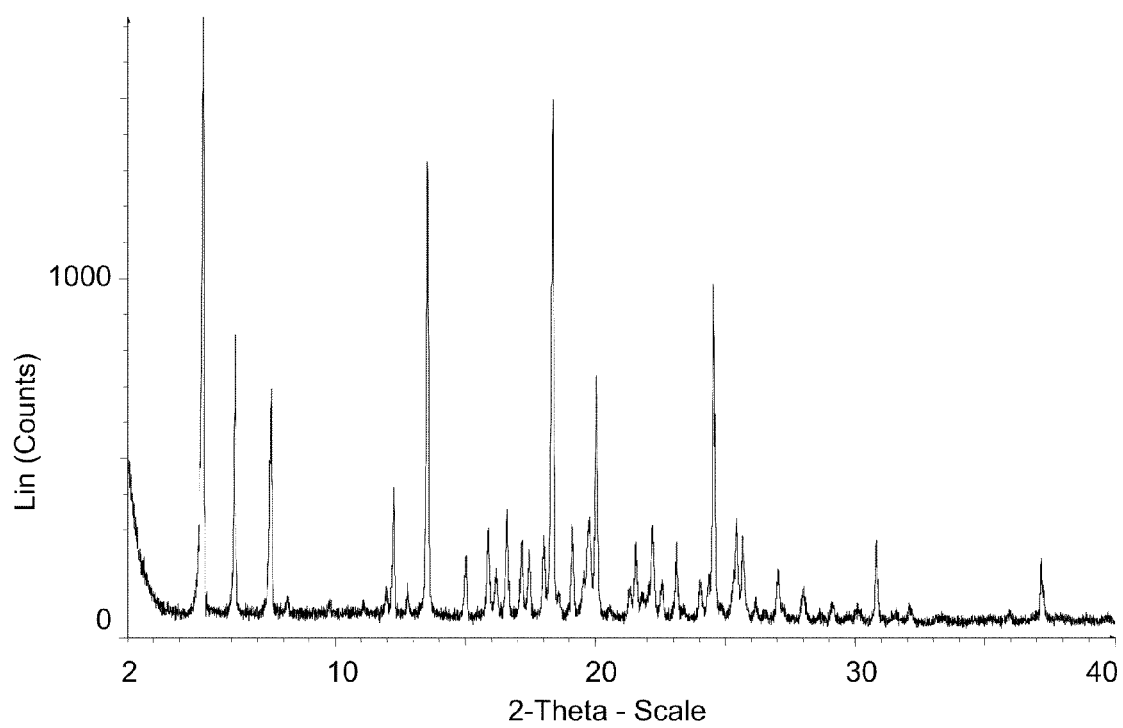

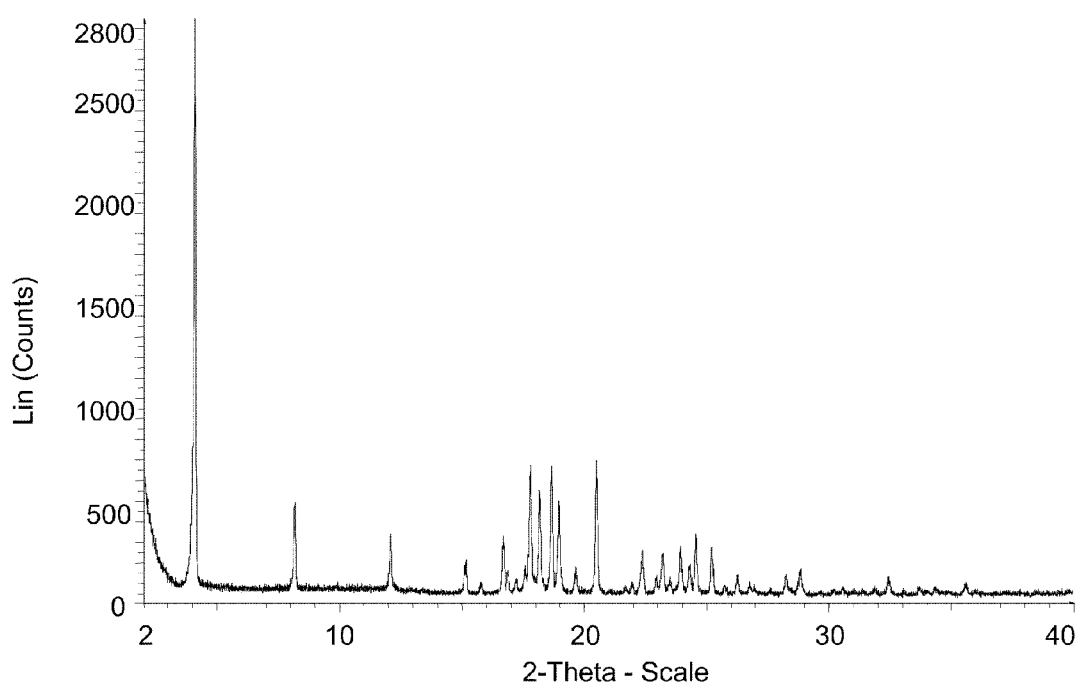
Figure B

Figure C
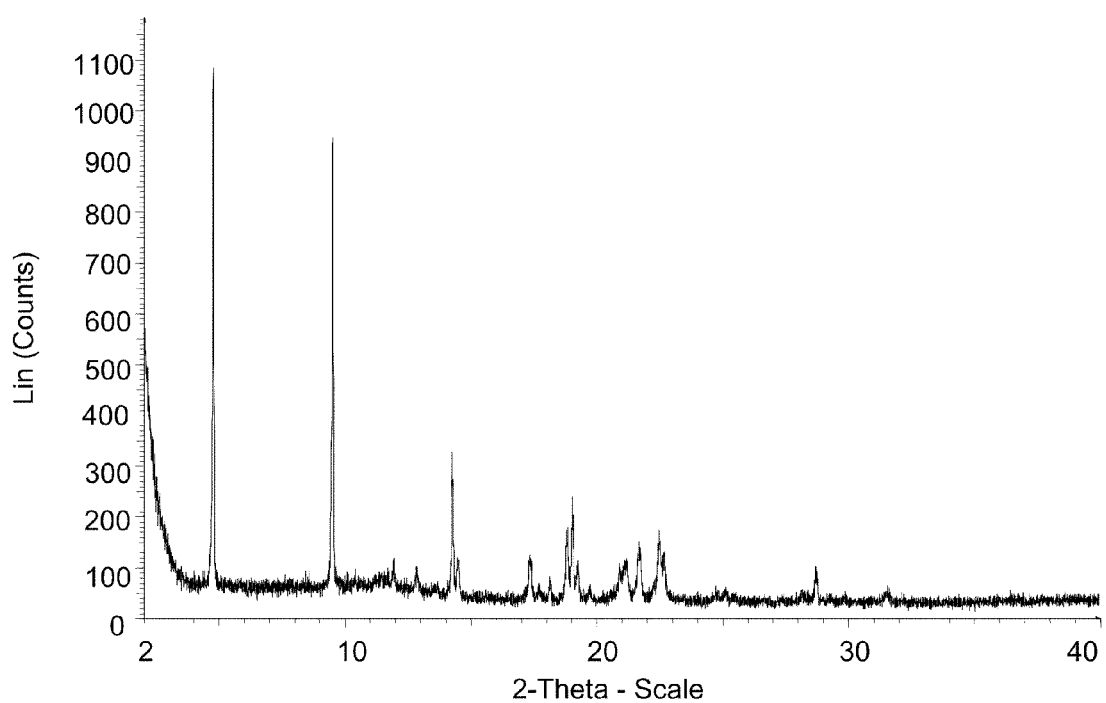

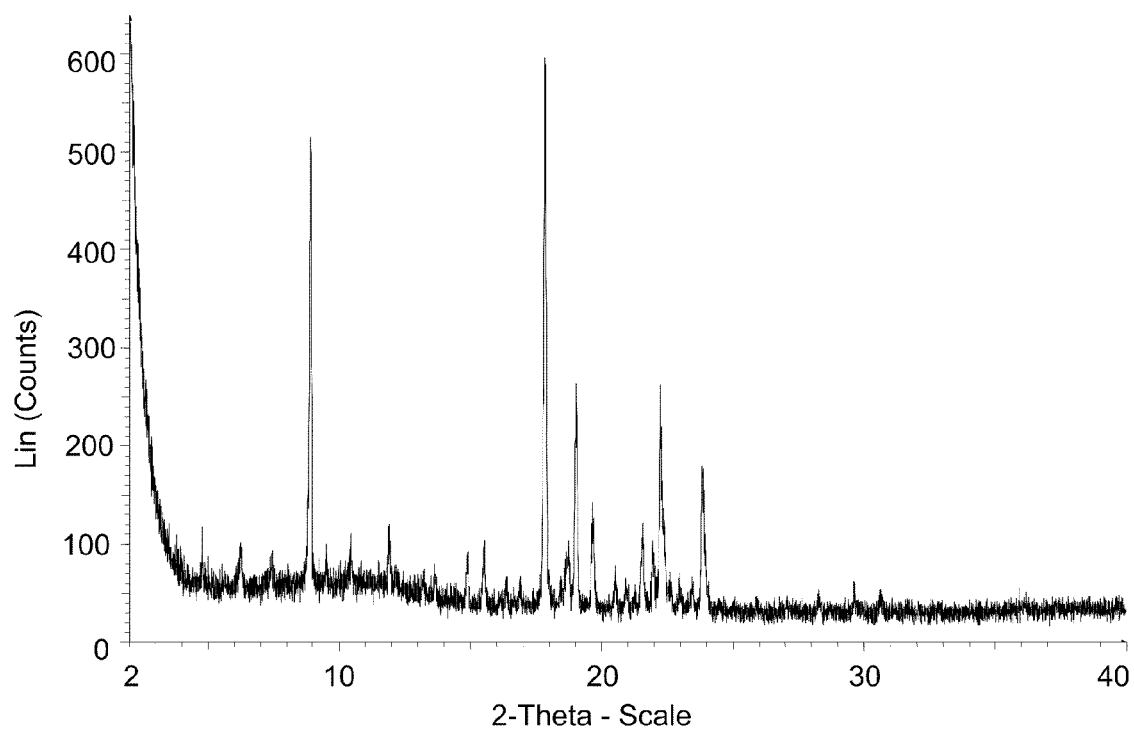
Figure D

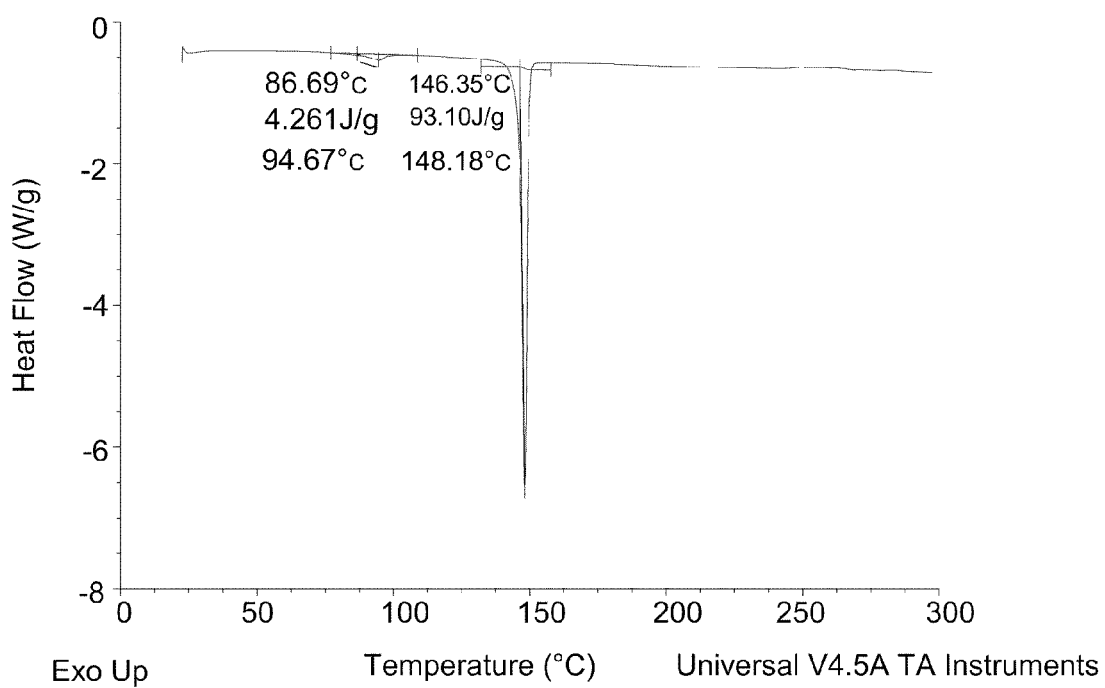
Figure E

Figure F
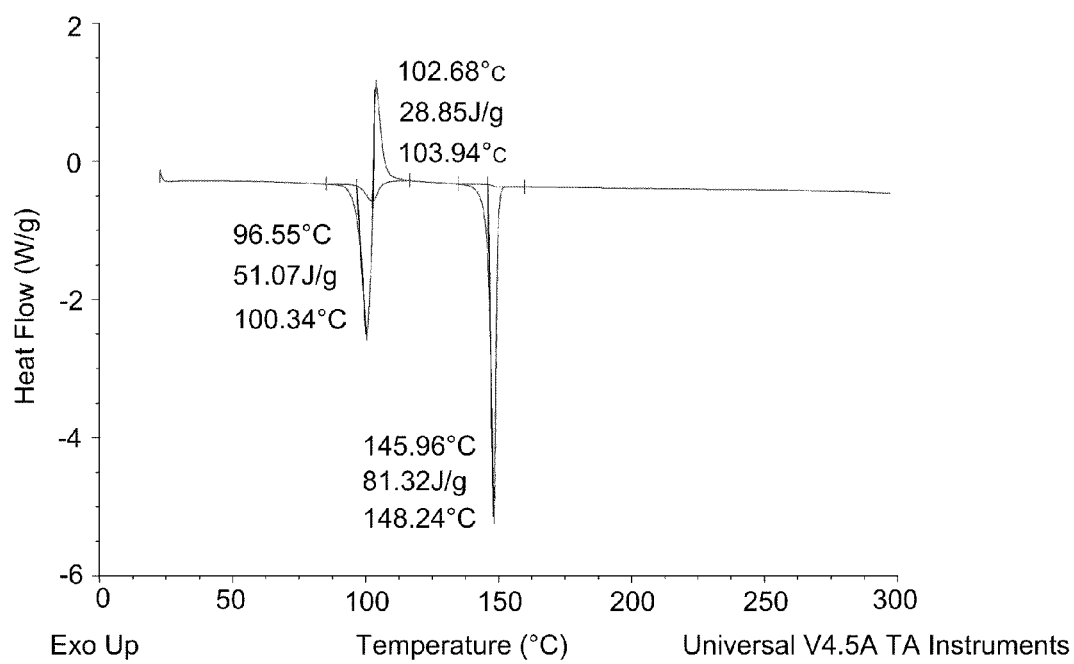

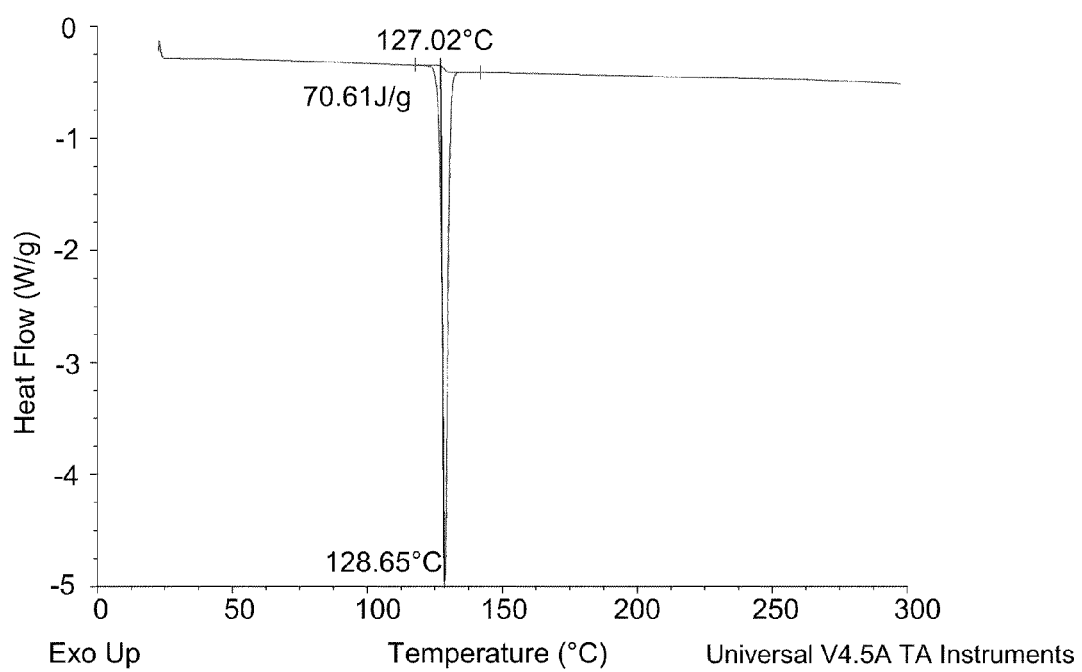
Figure G

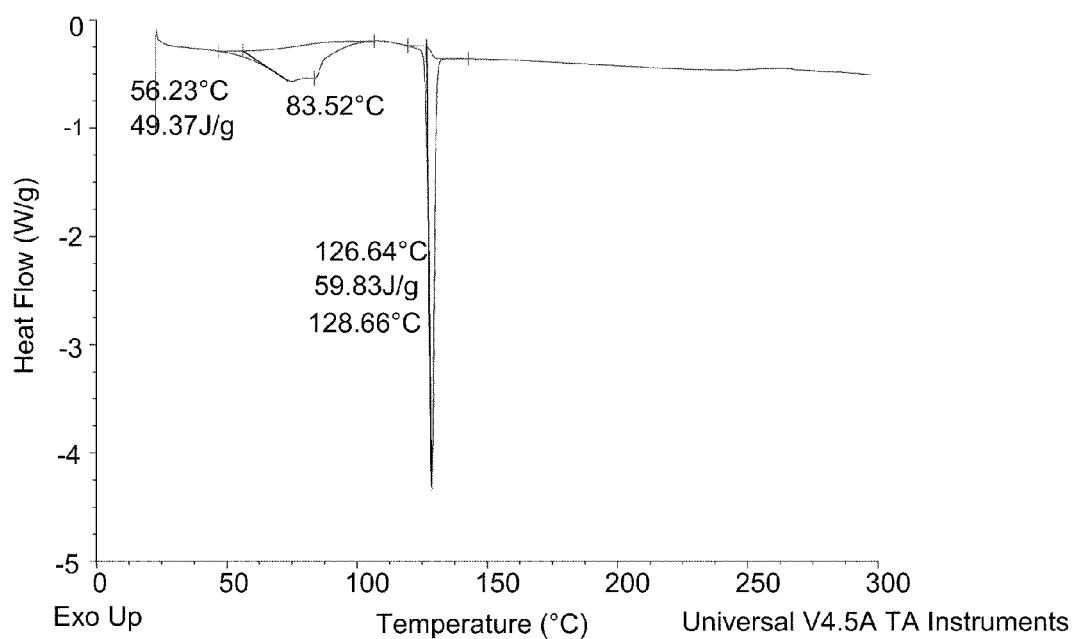
Figure H

Figure I
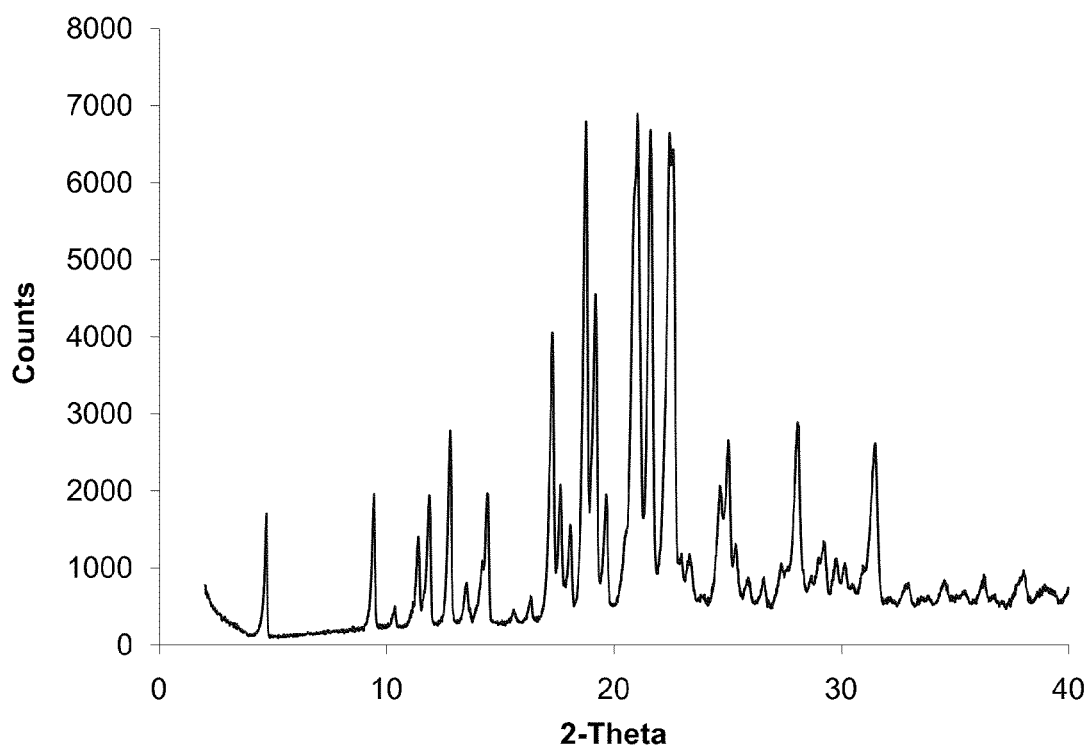

Figure J
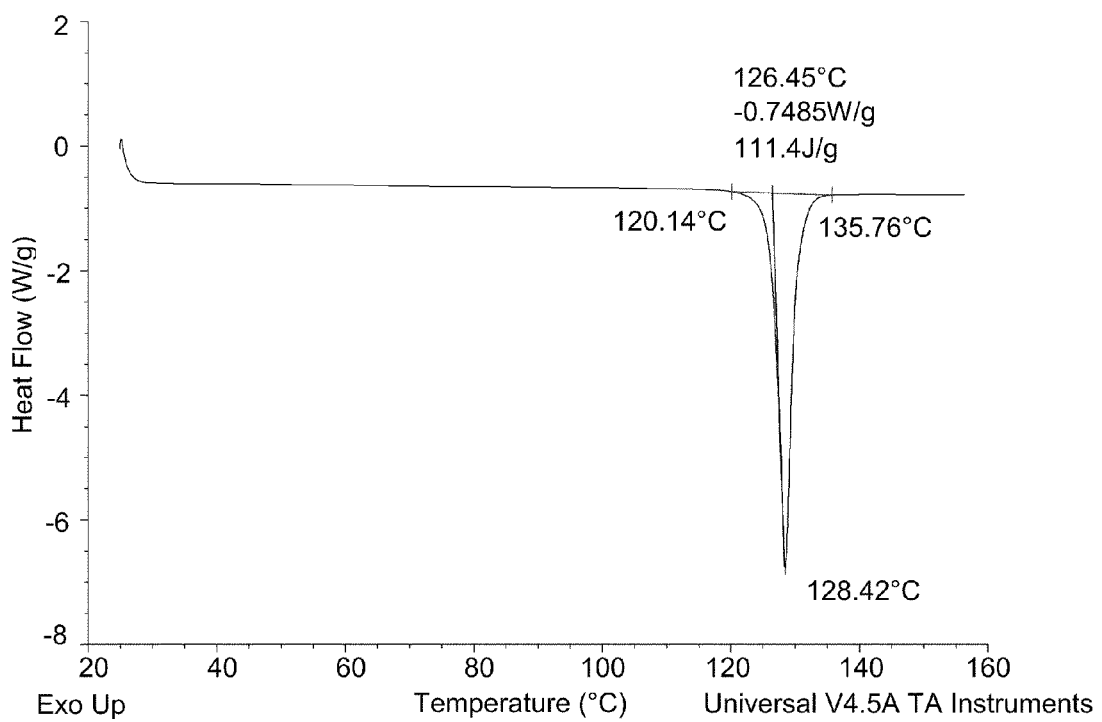

Figure K
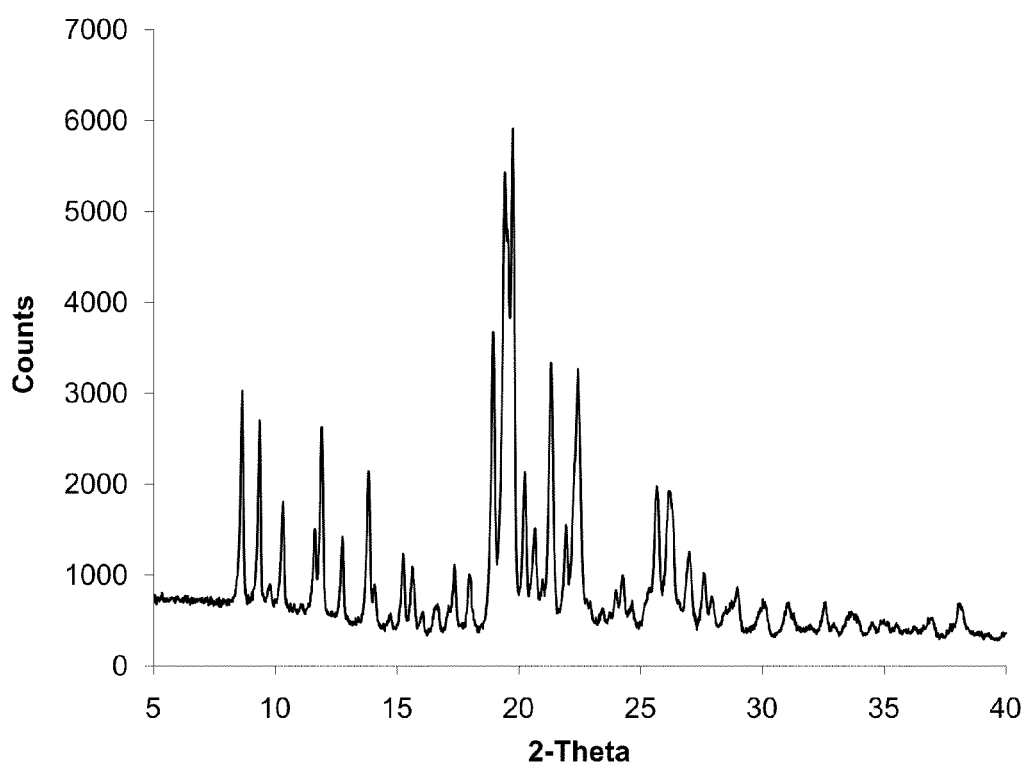

Figure L
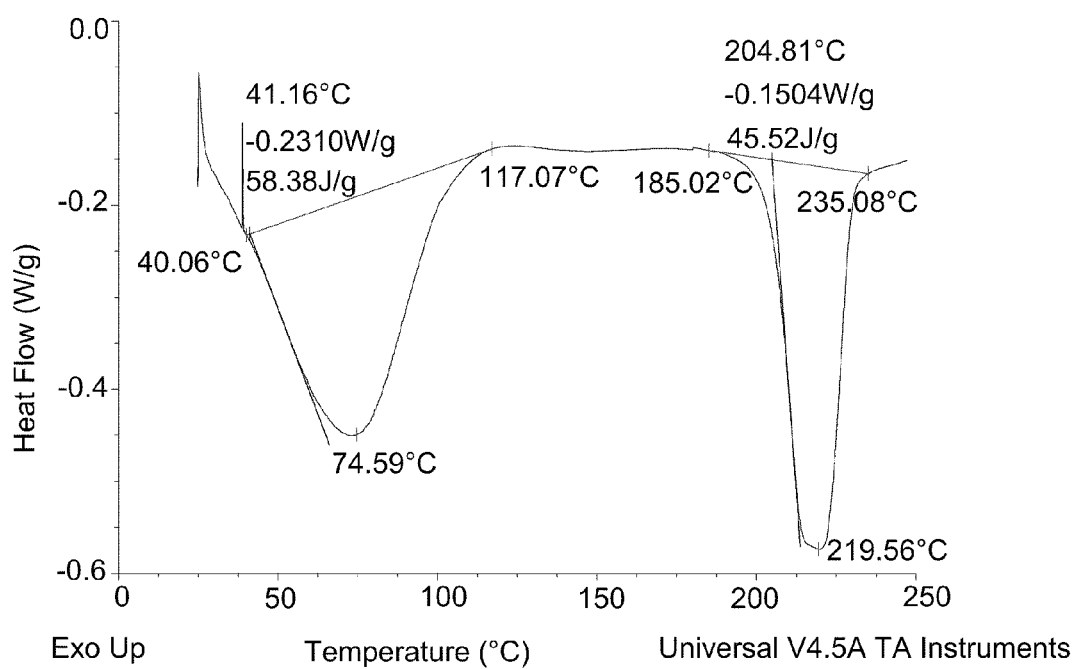

Figure M
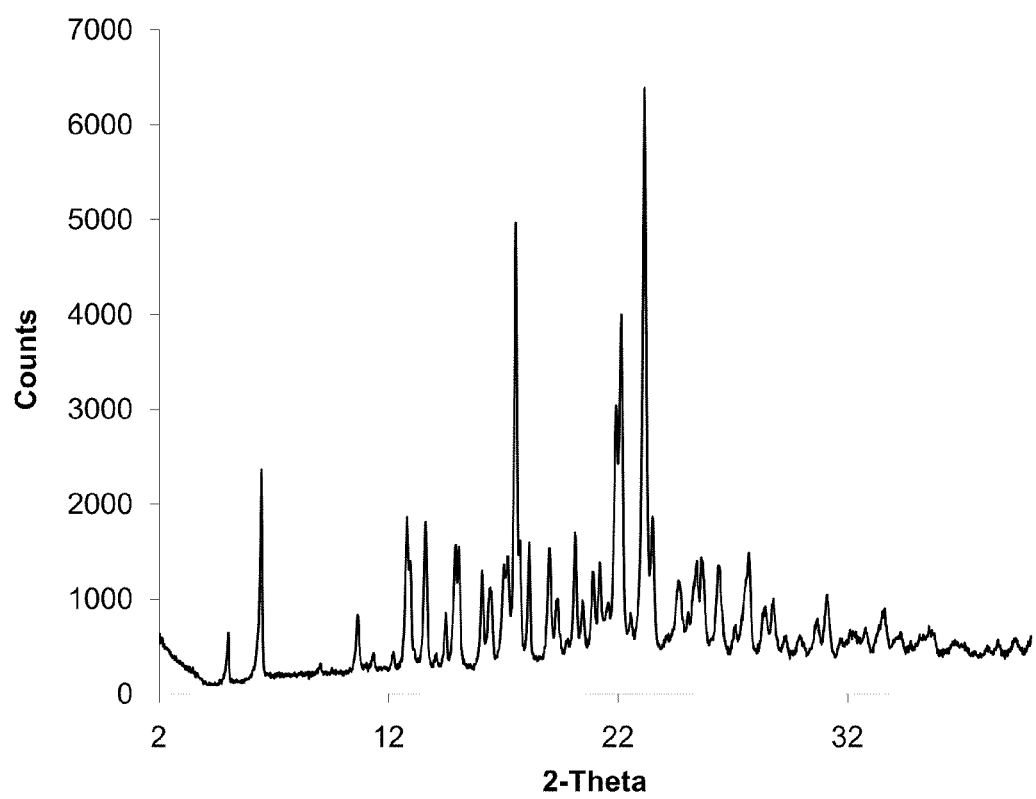

Figure N
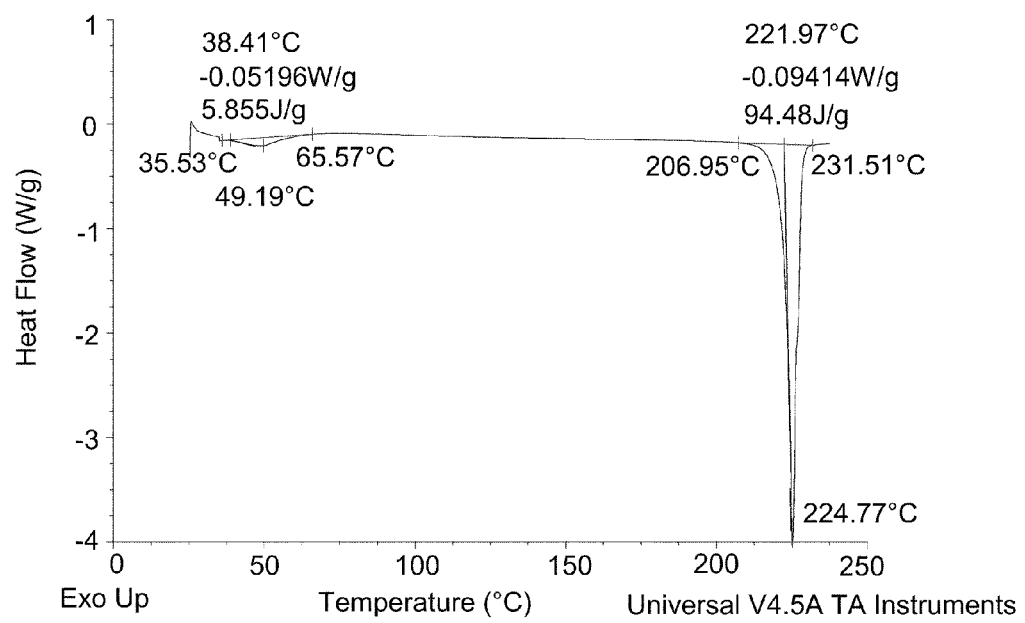

Figure O
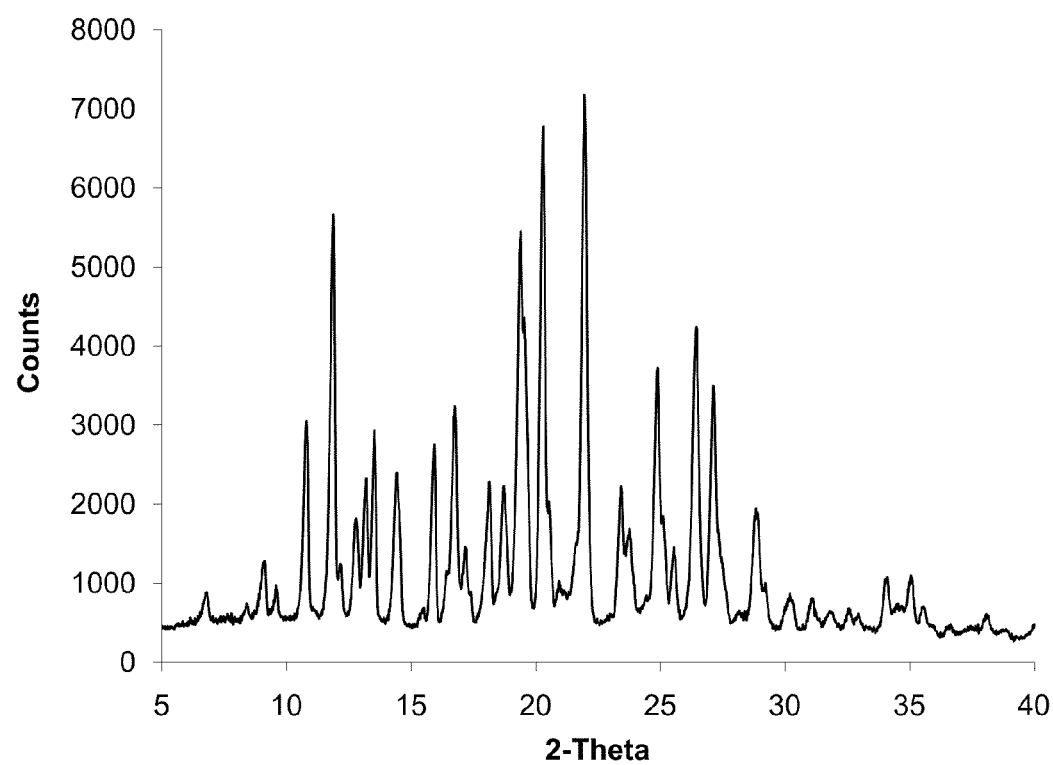

Figure P
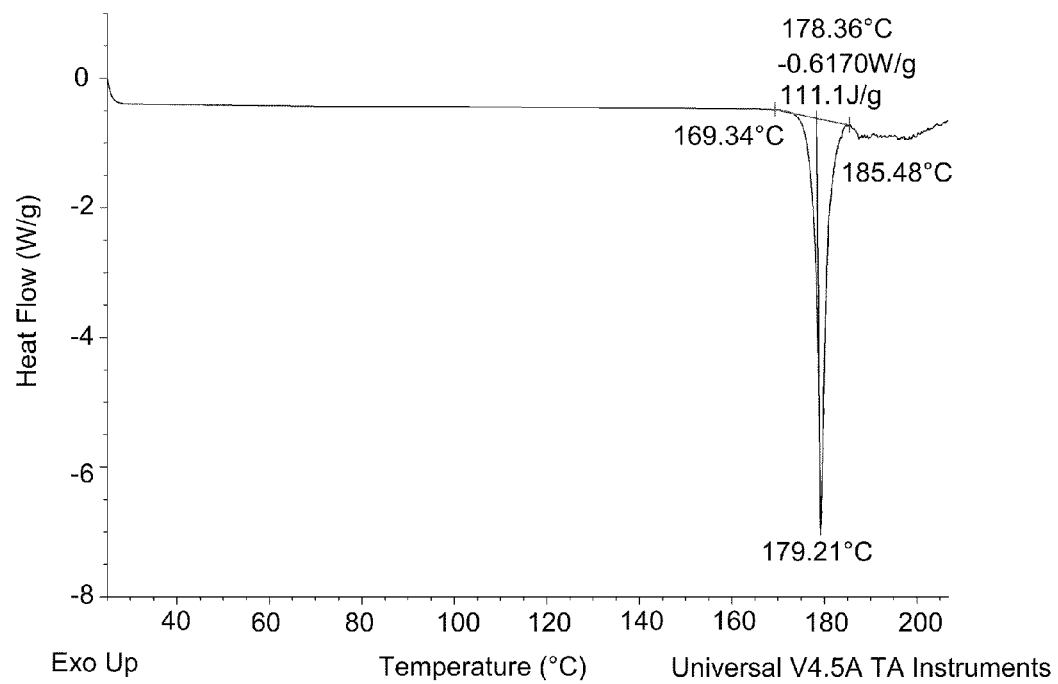

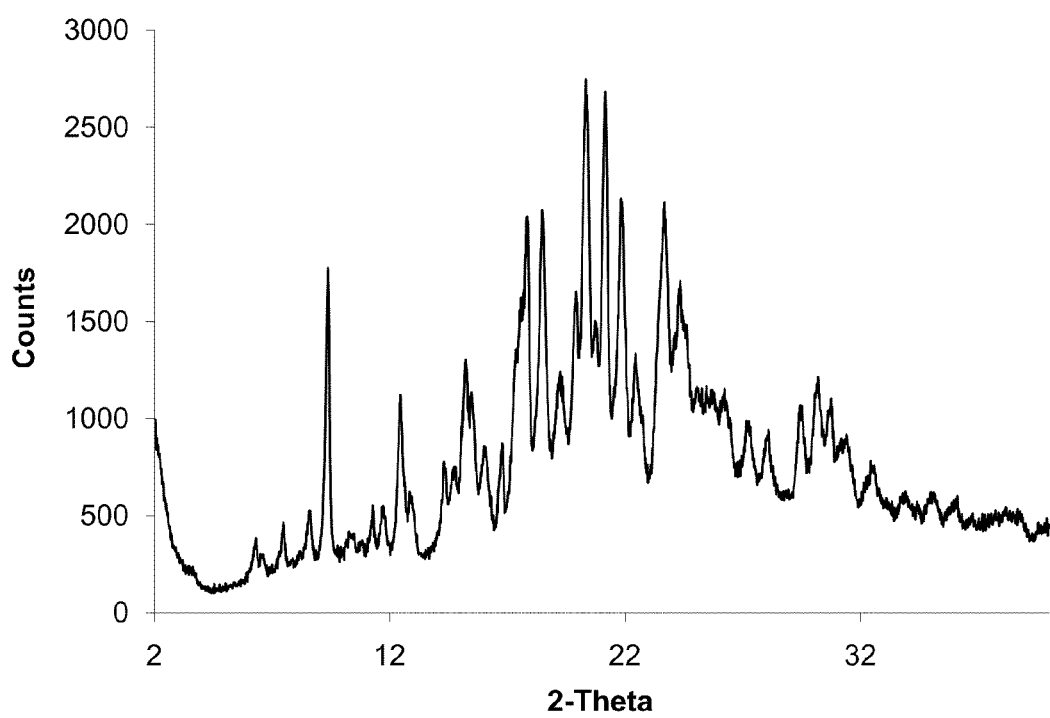
Figure Q

Figure R
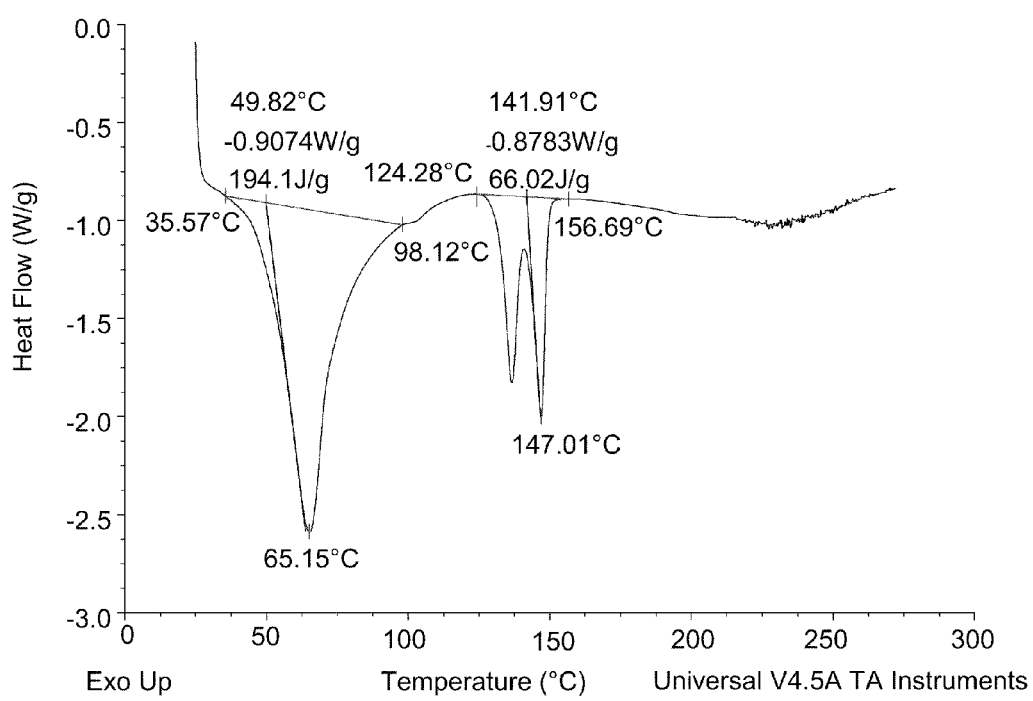

CHEMICAL COMPOUNDS—643

This application claims the benefit under 35 U.S.C. §119 (e) of Application No. 61/151,221 filed 10 Feb. 2009 and Application No. 61/187,766 filed 17 Jun. 2009.

This invention relates to new bicyclic derivatives and, more particularly, to bicyclic derivatives that act as ligands of the androgen receptor (AR). This invention also relates to methods for the preparation of such bicyclic derivatives, and novel intermediates in the preparation thereof, to pharmaceutical compositions containing such bicyclic derivatives, to the use of such bicyclic derivatives in the preparation of medicines, and to the use of such bicyclic derivatives in the treatment of androgen-receptor associated condition such as prostate cancer.

Prostate cancer is the second most common cause of death from cancer amongst men in developed countries and is projected to account for 25% of incident cases diagnosed and 9% of deaths due to cancer, accounting for over 27,000 deaths in the USA in 2009 (A. Jemal et al., CA Cancer J Clin published online May 2009).

The early stages of prostate cancer tumour growth are androgen-dependent and as such respond well to hormonal therapies aimed at causing androgen depletion by surgical (orchidectomy) or medical castration (e.g. LHRH-Agonists (Zoladex™, buserelin), LHRH antagonists (cetrorelix), or 5α-reductase inhibitors (finasteride)). These treatments are now often used in combination with androgen antagonists (e.g. Casodex™, cyproterone acetate, flutamide) to achieve total androgen blockade. The introduction of androgen deprivation therapy represented a major advance in prostate cancer treatment, however whilst highly effective initially in the majority of patients the cancer will recur within 2-3 years. This recurrence marks the transition of the cancer to a so-called castrate resistant state, where the tumour continues to grow in the presence of low circulating testosterone. At this point a classical androgen antagonist may initially be effective, but ultimately the cancer begins to grow again despite total androgen blockade. Castrate resistant prostate cancer is a largely unmet medical need with a 5 year survival rate of less than 15%. Docetaxal is currently the only treatment shown to improve survival, offering a benefit of 2 months (O. Smaletz and H. I Scher, Semin. Urol. Oncol., 2002, 20:155-163; D. A. Loblaw et al., J. Clin. Oncol., 2007, 25: 1596-1605).

There is now a body of evidence from both clinical and pre-clinical studies to support the notion that androgen receptor signalling is important in the majority of castrate resistant prostate cancers. The androgen receptor belongs to the family of steroid hormone receptors, which function as transcription factors. The binding of an androgen to the androgen receptor results in the stabilisation of the receptor and protects it form undergoing a rapid proteolytic degradation. The complex of androgen and androgen receptor is transported into the nucleus, where it regulates the expression of androgen responsive genes by binding to their androgen response DNA elements in the promoter region of such androgen responsive genes (D. J. Lamb et al. Vitam. Horm. 2001, 62, 199-230).

It is now well established that the majority of castrate resistant tumours possess a functional androgen receptor, which is frequently mutated or amplified. Receptor mutations arise in approximately 25-30% of patients treated with antagonists and can lead to a promiscuous receptor that recognises androgen antagonists as agonists or is stimulated by other steroids such as glucocorticoids. Gene amplification and over-expression of the androgen receptor is a common finding in castrate resistant cancers and leads to hypersensitivity to low levels of androgens. Pre-clinically the receptor is often over-expressed in in vitro and in vivo models of castrate resistant prostate cancer. Over expression of the receptor can convert hormone responsive lines to hormone refractory, and removal of the androgen receptor using siRNA prevents the growth of an androgen-independent xenograft model, data which support the critical role that this receptor plays in progression from androgen dependent to androgen resistant disease (B. J. Feldman; D. Feldman., Nat Rev Cancer, 2001, 1, 34-45; Chen et al, Curr Opin Pharmacol., 2008, 8, 440-8).

The identification of antiandrogens that would inhibit not only the natural form of the androgen receptor but also its mutated forms and thereby so alter the receptor molecule so that it became unstable would be very useful in the treatment of prostate tumours at various stages of growth. Such compounds could inhibit a recurrence of tumour growth or at least prolong the disease free interval. In the case of oestrogen receptors, such ligands have been identified that destabilise the receptor and lead to a reduction in the receptor content both in vitro and in vivo (S. Dauvois et al., Proc Natl. Acad. Sci. USA, 1992, 89, 4037-41; R. A. McClelland et al. Eur. J. Cancer, 1996, 32A, 413-416). In the case of the androgen receptor, a series of bicyclic derivatives capable of inducing cellular down-regulation of the androgen receptor in vitro has been described in WO 2009/081197.

A further series of bicyclic derivatives capable of inducing cellular down-regulation of the androgen receptor is described herein. According to a first aspect of the present invention there is therefore provided a compound of Formula (I), or a pharmaceutically acceptable salt thereof:

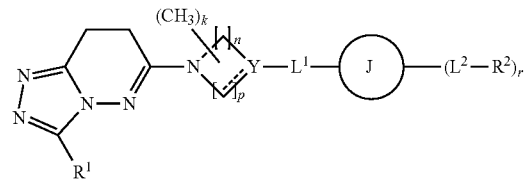

(I)

wherein
$R^1$ represents halo$C_{1-4}$alkyl;
k represents 0, 1 or 2;
n and p independently represent 1 or 2;
Y represents N, C, CH or COH;
- - - - represents a single bond when Y is N, CH or COH;
- - - - represents a double bond when Y is C, $L^1$ is a direct bond and J is indolyl or pyrrolopyridinyl;
$L^1$ represents a direct bond, —(CR$^3$R$^4$)$_t$—, —(CR$^3$R$^4$)$_v$—O—(CR$^3$R$^4$)$_v$—, —N(R$^5$)—(CH$_2$)$_q$—, —S—, —S(O)— or —S(O)$_2$—;
$R^3$ and $R^4$, identically or differently on each occurrence, represent hydrogen or methyl;
$R^5$ represents hydrogen or methyl;
q, identically or differently on each occurrence, represents 0, 1, 2, 3 or 4;
t represents 1, 2 or 3;
v, identically or differently on each occurrence, represents 0, 1 or 2;
J represents:
  aryl;
  $C_{3-6}$cycloalkyl;
  a monocyclic 4, 5, 6 or 7 membered heterocyclic ring which comprises 1, 2 or 3 heteroatoms independently selected from O, N or S;

a 5 or 6 membered monocyclic heteroaryl ring which comprises 1, 2, 3 or 4 heteroatoms independently selected from O, N or S; or a 9 or 10 membered bicyclic heteroaryl ring system which comprises 1, 2, 3, 4 or 5 heteroatoms independently selected from O, N or S;

$L^2$ represents a direct bond, $—(CR^3R^4)_t—$, $—C(O)N(R^5)—(CH_2)_q—$, $—C(O)N(R^5)—(CH_2)_q—S(O)_2—$, $—NR^5C(O)—(CH_2)_q—$, $—C(O)—(CH_2)_q—$, $—O—(CR^9R^{10})_q—$, $—O—(CR^3R^4)_q—NR^5—(CH_2)_q—$, $—O—(CR^3R^4)_q—C(O)NR^5—(CH_2)_q—$, $—S—$, $—S(O)—$ or $—S(O)_2—$;

$R^9$ and $R^{10}$, identically or differently on each occurrence, represent hydrogen, methyl, ethyl, isopropyl, cyclopropyl or methoxymethyl;

$R^2$ represents:
halo, $C_{1-6}$alkyl, $C_{2-6}$alkenyl, $C_{2-6}$alkynyl, carboxy, $C_{1-6}$alkoxy, cyano, oxo, fluoro$C_{1-6}$alkyl, hydroxy, amino, N—$C_{1-4}$alkylamino or N,N-di-$C_{1-4}$alkylamino;

aryl, wherein the aryl ring is optionally substituted with 1, 2 or 3 substituents selected from $R^6$;

a monocyclic 4, 5, 6 or 7 membered heterocyclic ring which comprises 1, 2 or 3 heteroatoms independently selected from O, N or S and wherein the heterocyclic ring is optionally substituted with 1, 2 or 3 substituents selected from $R^6$;

a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^6$; or a 9 or 10 membered bicyclic heteroaryl ring system which comprises 1, 2, 3, 4 or 5 heteroatoms independently selected from O, N or S and wherein the heterocyclic ring is optionally substituted with 1, 2 or 3 substituents selected from $R^6$;

$R^6$ represents amino, halo, $C_{1-6}$alkyl, $C_{3-6}$cycloalkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, oxetan-3-ylcarbonyl, N—$C_{1-4}$alkylamino, N,N-di-$C_{1-4}$alkylamino or $—C(O)NR^7R^8$ wherein $R^7$ and $R^8$ independently represent hydrogen or methyl; and r represents 0, 1, 2 or 3.

According to a second aspect of the present invention there is therefore provided a compound of Formula (I), or a pharmaceutically acceptable salt thereof:

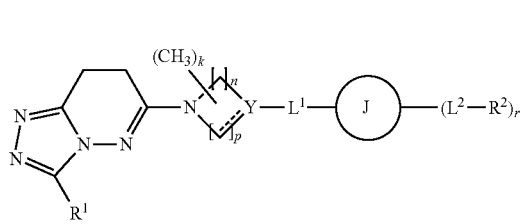

(I)

wherein
$R^1$ represents halo$C_{1-4}$alkyl;
k represents 0, 1 or 2;
n and p independently represent 1 or 2;
Y represents N, C, CH or COH;
----represents a single bond when Y is N, CH or COH;
----represents a double bond when Y is C, $L^1$ is a direct bond and J is indolyl;

$L^1$ represents a direct bond, $—(CR^3R^4)_t—$, $—(CR^3R^4)_v—O—(CR^3R^4)_v—$, $—N(R^5)—(CH_2)_q—$, $—S—$, $—S(O)—$ or $—S(O)_2—$;

$R^3$ and $R^4$, identically or differently on each occurrence, represent hydrogen or methyl;

$R^5$ represents hydrogen or methyl;

q, identically or differently on each occurrence, represents 0, 1, 2 or 3;

t represents 1, 2 or 3;

v, identically or differently on each occurrence, represents 0, 1 or 2;

J represents:
aryl;
$C_{3-6}$cycloalkyl;
a monocyclic 4, 5, 6 or 7 membered heterocylic ring which comprises 1, 2 or 3 heteroatoms independently selected from O, N or S;

a 5 or 6 membered monocyclic heteroaryl ring which comprises 1, 2, 3 or 4 heteroatoms independently selected from O, N or S; or a 9 or 10 membered bicyclic heteroaryl ring system which comprises 1, 2, 3, 4 or 5 heteroatoms independently selected from O, N or S;

$L^2$ represents a direct bond, $—(CR^3R^4)_t—$, $—C(O)N(R^5)—(CH_2)_q—$, $—C(O)N(R^5)—(CH_2)_q—S(O)_2—$, $—NR^5C(O)—(CH_2)_q—$, $—C(O)—(CH_2)_q—$, $—O—(CH_2)_q—$, $—O—(CR^3R^4)_q—NR^5—(CH_2)_q—$, $—O—(CR^3R^4)_q—C(O)NR^5—(CH_2)_q—$, $—S—$, $—S(O)—$ or $—S(O)_2—$;

$R^2$ represents:
halo, $C_{1-6}$alkyl, $C_{2-6}$alkenyl, $C_{2-6}$alkynyl, carboxy, $C_{1-6}$alkoxy, cyano, oxo, fluoro$C_{1-6}$alkyl, hydroxy, amino, N—$C_{1-4}$alkylamino or N,N-di-$C_{1-4}$alkylamino;

aryl, wherein the aryl ring is optionally substituted with 1, 2 or 3 substituents selected from $R^6$;

a monocylic 4, 5, 6 or 7 membered heterocyclic ring which comprises 1, 2 or 3 heteroatoms independently selected from O, N or S and wherein the heterocyclic ring is optionally substituted with 1, 2 or 3 substituents selected from $R^6$;

a monocylic 5 or 6 membered heteroaryl ring which comprises 1, 2, 3 or 4 heteroatoms independently selected from O, N or S and wherein the heteroaryl ring is optionally substituted with 1, 2 or 3 substituents selected from $R^6$; or a 9 or 10 membered bicyclic heteroaryl ring system which comprises 1, 2, 3, 4 or 5 heteroatoms independently selected from O, N or S and wherein the heterocyclic ring is optionally substituted with 1, 2 or 3 substituents selected from $R^6$;

$R^6$ represents amino, halo, $C_{1-6}$alkyl, $C_{2-6}$alkenyl, $C_{2-6}$alkynyl, $C_{1-6}$alkoxy, $C_{2-6}$alkanoyl, $C_{1-6}$alkoxy$C_{1-6}$alkyl, carboxy, cyano, oxo, fluoro$C_{1-6}$alkyl, hydroxy, hydroxy$C_{1-6}$alkyl, $C_{1-6}$alkylsulphanyl, $C_{1-6}$alkylsulphinyl, $C_{1-6}$alkylsulphonyl, N—$C_{1-4}$alkylamino, N,N-di-$C_{1-4}$alkylamino or $—C(O)NR^7R^8$ wherein $R^7$ and $R^8$ independently represent hydrogen or methyl; and r represents 0, 1, 2 or 3.

It is to be understood that any suitable -$L^2$-$R^2$ group of Formula (I) may be bonded to any available atom of group J and that $R^2$ may be linked to group J via any suitable linker selected from $L^2$.

It is to be understood that, insofar as certain of the compounds of Formula (I) defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula (I) defined above may exhibit the phenomenon of tautomerism. In particular, tautomerism may affect any heterocyclic groups that bear 1 or 2 oxo substituents. It is to be understood that the present invention includes in its definition any such tautomeric form, or a mixture thereof, which possesses androgen receptor ligand activity and is not to be limited merely to any one tautomeric form utilised within the formulae drawings or named in the Examples.

It is to be understood that certain compounds of Formula (I) above may exist in unsolvated forms as well as solvated forms, such as, for example, hydrated forms. It is to be understood that the present invention encompasses all such solvated forms that possess androgen receptor ligand activity. In one embodiment of the invention, there is therefore provided a compound of Formula (I) in a solvated form. In another embodiment of the invention, there is therefore provided a compound of Formula (I) in a hydrated form.

It is also to be understood that certain compounds of Formula (I) may exist in crystalline form and exhibit polymorphism. The present invention encompasses all such polymorphic forms which possess androgen receptor ligand activity. In one embodiment of the invention, there is therefore provided a compound of Formula (I), or a pharmaceutically acceptable salt or solvate thereof, in crystalline form.

The term "halo" is used herein to denote fluoro, chloro, bromo and iodo.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group.

The term "$C_{1-6}$alkyl" is intended to mean a saturated carbon chain of 1 to 6 carbon atoms in length which may be straight-chained or branched. However references to individual alkyl groups such as "propyl" are specific for the straight chain version only and references to individual branched-chain alkyl groups such as tert-butyl are specific for the branched chain version only. For example, "$C_{1-6}$alkyl" includes, but is not limited to, methyl, ethyl, propyl, isopropyl, butyl, tert-butyl, pentyl, tert-pentyl, hexyl and isohexyl. The term "$C_{1-4}$alkyl" is to be construed accordingly.

The term "$C_{2-4}$alkenyl" is intended to mean an unsaturated carbon chain of 2 to 4 carbon atoms in length, which may be straight-chained or branched, containing at least one carbon to carbon double bond. However references to individual alkenyl groups such as "propenyl" are specific for the straight chain version only and references to individual branched-chain alkyl groups such as isopropenyl are specific for the branched chain version only. For example, "$C_{2-4}$alkenyl" includes, but is not limited to, ethenyl, propenyl, isopropenyl and butenyl.

The term "$C_{2-4}$alkynyl" is intended to mean an unsaturated carbon chain of 2 to 4 carbon atoms in length, which may be straight-chained or branched, containing at least one carbon to carbon triple bond. For example, "$C_{2-4}$alkynyl" includes, but is not limited to, ethynyl, propynyl and butynyl.

The term "$C_{3-6}$cycloalkyl" is intended to mean a saturated 3 to 6 membered monocyclic carbon ring. For example "$C_{3-6}$cycloalkyl" includes cyclopropyl, cyclobutyl, cyclopentyl and cyclohexyl.

The term fluoro$C_{1-6}$alkyl" is intended to mean a saturated carbon chain of 1 to 6 carbon atoms in length which may be straight-chained or branched wherein at least one of the hydrogen atoms have been replaced by fluorine. For example, "fluoro$C_{1-6}$alkyl" includes, but is not limited to, fluoromethyl, fluoroethyl, fluoropropyl, fluoroisopropyl, fluorobutyl, fluoroisobutyl, fluoro-tert-butyl, fluoropentyl, fluoroisopentyl, fluorohexyl, fluoroisohexyl, trifluoromethyl, pentafluoroethyl, heptafluoropropyl, nonafluorobutyl, undecafluoropentyl and tridecafluorohexyl. The term "fluoro$C_{1-4}$alkyl" should be construed accordingly.

The term "$C_{1-6}$ alkoxy" is intended to mean a saturated carbon chain of 1 to 6 carbon atoms in length, which may be straight-chained or branched, linked to oxygen. For example, "$C_{1-6}$ alkoxy" includes, but is not limited to, methoxy, ethoxy, propoxy, butoxy, pentoxy and hexoxy.

The term "$C_{2-6}$alkanoyl" is intended to mean a saturated carbon chain of 1 to 5 carbon atoms in length, which may be straight-chained, branched or cyclic, linked to carbonyl. For example, "$C_{2-6}$alkanoyl" includes, but is not limited to, acetyl, propanoyl, butanoyl, pentanoyl, hexanoyl, cyclopropylcarbonyl and cyclobutylcarbonyl.

The term "$C_{1-6}$alkoxy$C_{1-6}$alkyl" is intended to mean a saturated carbon chain of 1 to 6 carbon atoms in length, which may be straight-chained or branched, linked via oxygen to another saturated carbon chain of 1 to 6 carbon atoms in length, which may be straight-chained or branched. For example, "$C_{1-6}$alkoxy$C_{1-6}$alkyl" includes, but is not limited to, methoxyethyl, methoxypropyl, ethoxypropyl, propoxyethyl and butoxypropyl.

The term "hydroxy$C_{1-6}$alkyl" is intended to mean a saturated carbon chain of 1 to 6 carbon atoms in length, which may be straight-chained or branched, wherein one of the hydrogen atoms has been replaced by a hydroxy group. For example "hydroxy$C_{1-6}$alkyl" includes, but is not limited to, hydroxymethyl, hydroxyethyl, 2-hydroxypropyl, 3-hydroxypropyl, 1-hydroxyisopropyl, 4-hydroxybutyl, hydroxypentyl, hydroxyhexyl and hydroxyisohexyl.

The term "$C_{1-6}$alkylsulphanyl" is intended to mean a saturated carbon chain of 1 to 6 carbon atoms in length, which may be straight-chained or branched, linked to sulphur. For example, "$C_{1-6}$alkylsulphanyl" includes, but is not limited to, methylsulphanyl, ethylsulphanyl, propylsulphanyl, isopropylsulphanyl, butylsulphanyl, isobutylsulphanyl, tert-butylsulphanyl, pentylsulphanyl and hexylsulphanyl.

The term "$C_{1-6}$alkylsulphinyl" is intended to mean a saturated carbon chain of 1 to 6 carbon atoms in length, which may be straight-chained or branched, linked to sulphoxide. For example, "$C_{1-6}$alkylsulphinyl" includes, but is not limited to, methylsulphinyl, ethylsulphinyl, propylsulphinyl, isopropylsulphinyl, butylsulphinyl, isobutylsulphinyl, tert-butylsulphinyl, pethylsulphinyl and hexylsulphinyl.

The term "$C_{1-6}$alkylsulphonyl" is intended to mean a saturated carbon chain of 1 to 6 carbon atoms in length, which may be straight-chained or branched, linked to sulphur dioxide. For example, "$C_{1-6}$alkylsulphonyl" includes, but is not limited to, methylsulphonyl, ethylsulphonyl, propylsulphonyl, isopropylsulphonyl, butylsulphonyl, isobutylsulphonyl, tert-butylsulphonyl, pentylsulphonyl and hexylsulphonyl.

The term "N—$C_{1-4}$alkylamino" is intended to mean a saturated carbon chain of 1 to 4 carbon atoms in length, which may be straight-chained or branched, linked to a secondary amino group. For example, "N—$C_{1-4}$alkylamino" includes, but is not limited to, methylamino, ethylamino, propylamino and butylamino.

The term "N,N-di-$C_{1-4}$alkylamino" is intended to mean a saturated carbon chain of 1 to 4 carbon atoms in length, which may be straight-chained or branched, linked to a tertiary amino group, which is in turn linked to a further saturated carbon chain of the same length. For example, "N,N-di-$C_{1-4}$alkylamino" includes, but is not limited to, N,N-dimethylamino, N,N-diethylamino, N,N-dipropylamino and N,N-dibutylamino.

The term "halo$C_{1-4}$alkyl" is intended to mean a saturated carbon chain of 1 to 4 carbon atoms in length which may be straight-chained or branched wherein at least one of the hydrogen atoms have been replaced by a halo atom. For example, "halo$C_{1-4}$alkyl" includes, but is not limited to, difluoromethyl, trifluoromethyl, chloro(difluoro)methyl, difluoroethyl and difluoropropyl.

The term "aryl" is intended to mean phenyl or naphthyl.

Unless stated otherwise, the term "monocyclic heteroaryl ring" is intended to mean a 5 or 6 membered, totally unsaturated and/or aromatic monocyclic ring which comprises 1, 2, 3 or 4 heteroatoms independently selected from nitrogen, oxygen or sulphur, linked via ring carbon atoms or ring nitrogen atoms where a bond from a nitrogen is possible, for example no bond is possible to the nitrogen of a pyridine ring, but a bond is possible through the 1-nitrogen of a pyrazole ring. Examples of 5 or 6 membered heteroaryl rings include, but are not limited to, furanyl, imidazolyl, triazolyl, tetrazolyl, pyrazinyl, pyrazolyl, pyrimidinyl, pyridazinyl, pyridinyl, pyrrolyl, isoxazolyl, oxazolyl, 1,2,4 oxadiazolyl, isothiazolyl, thiazolyl, thiadiazolyl, 1,2,4-triazolyl and thiophenyl.

Unless stated otherwise, the term "bicyclic heteroaryl ring system" is intended to mean a 9 or 10 membered, totally unsaturated and/or aromatic fused bicyclic ring system which comprises 1, 2, 3, 4 or 5 heteroatoms independently selected from nitrogen, oxygen or sulphur, linked via ring carbon atoms or ring nitrogen atoms where a bond from a nitrogen is allowed, or a 9 or 10 membered fused bicyclic ring system wherein only one ring is totally saturated and/or aromatic and which comprises 1, 2, 3, 4 or 5 heteroatoms independently selected from nitrogen, oxygen or sulphur. Examples of 5/6 and 6/6 bicyclic heteroaryl ring systems include benzofuranyl, benzimidazolyl, benzthiophenyl, benzthiazolyl, benzisothiazolyl, benzoxazolyl, benzisoxazolyl, 1,3-benzodioxolyl, indolyl, pyridoimidazolyl, pyrimidoimidazolyl, pyrrolopyridinyl, quinolinyl, isoquinolinyl, quinoxalinyl, quinazolinyl, phthalazinyl, cinnolinyl and naphthyridinyl. This definition further comprises sulphur-containing rings wherein the sulphur atom has been oxidised to an S(O) or $S(O_2)$ group.

Unless stated otherwise, the term "heterocyclic ring" is intended to mean a 4, 5, 6 or 7 membered fully saturated or partially saturated monocyclic ring which comprises 1, 2 or 3 heteroatoms selected from nitrogen, oxygen or sulphur linked via ring carbon atoms or ring nitrogen atoms. Examples of 4, 5, 6 or 7 membered heterocyclic rings include, but are not limited to, azetidinyl, tetrahydrofuranyl, dihydropyranyl, tetrahydropyranyl, pyrrolinyl, pyrrolidinyl, thiazolidinyl, morpholinyl, oxetanyl, piperidinyl, piperazinyl, dihydropyridinyl, dihydropyrimidinyl and azepanyl. This definition further comprises sulphur-containing rings wherein the sulphur atom has been oxidised to an S(O) or $S(O_2)$ group.

In further embodiments of the first aspect of the present invention, each of the following definitions of J, Y, $L^1$, $L^2$, $R^1$, $R^2$, $R^3$, $R^4$, $R^5$, $R^6$, $R^9$, $R^{10}$, n, p, k and r in paragraphs (1) to (73) hereinafter may be used individually or in combination with one or more of the other following definitions to limit the broadest definition of Formula (I). For example, the skilled person would understand that paragraphs (4), (11), (21), (24) and (35) could be combined to provided a compound of Formula (I), or a pharmaceutically acceptable salt thereof, wherein $R^1$ represents trifluoromethyl, Y represents CH, $L^1$ represents a direct bond, J represents phenyl and $L^2$ represents —O—$(CR^9R^{10})_q$—. Similarly, paragraphs (4), (11), (21) (31), (35) and (55) could be combined to provided a compound of Formula (I), or a pharmaceutically acceptable salt thereof, wherein $R^1$ represents trifluoromethyl, Y represents CH, $L^1$ represents a direct bond, J represents phenyl and $L^2$ is bonded at the para position of the phenyl ring relative to linkage $L^1$, $L^2$ represents —O—$(CR^9R^{10})_q$— and $R^2$ represents piperidinyl or piperazinyl optionally substituted with 1, 2 or 3 substituents selected from $R^6$.

(1) $R^1$ represents difluoromethyl, trifluoromethyl, chloro(difluoro)methyl, difluoroethyl or difluoropropyl;
(2) $R^1$ represents difluoromethyl, trifluoromethyl or chloro (difluoro)methyl;
(3) $R^1$ represents difluoromethyl
(4) $R^1$ represents trifluoromethyl;
(5) $R^1$ represents chloro(difluoro)methyl;
(6) Y represents N, CH or COH;
(7) Y represents C, CH or COH;
(8) Y represents CH or COH;
(9) Y represents C;
(10) Y represents N;
(11) Y represents CH;
(12) Y represents COH;
(13) k represents 0;
(14) k represents 1;
(15) k represents 2;
(16) n and p both represent 2;
(17) n represents 1 and p represents 2;
(18) n and p both represent 1;
(19) $L^1$ represents a direct bond or —$(CR^3R^4)_r$—;
(20) $L^1$ represents a direct bond, —$CH_2$—, —$CH(CH_3)$—;
(21) $L^1$ represents a direct bond;
(22) $L^1$ represents —$CH_2$—;
(23) J represents phenyl, pyridinyl, indolyl or pyrrolopyridinyl;
(24) J represents phenyl;
(25) J represents indolyl;
(26) J represents indol-3-yl;
(27) J represents pyridinyl;
(28) J represents pyridin-3-yl;
(29) J represents pyrrolopyridinyl;
(30) J represents pyrrolopyridin-3-yl;
(31) J represents phenyl and $L^2$ is bonded at the para position of the phenyl ring relative to linkage $L^1$;
(32) $L^2$ represents a direct bond;
(33) $L^2$ represents a direct bond, —O—$(CR^9R^{10})_q$— or —O—$(CR^3R^4)_q$—C(O)$NR^5$—$(CH_2)_q$—;
(34) $L^2$ represents a direct bond;
(35) $L^2$ represents —O—$(CR^9R^{10})_q$—;
(36) $L^2$ represents —O—$(CH_2)_q$—;
(37) $L^2$ represents —O—$CH_2$—$CH_2$—;
(38) $L^2$ represents —O—$CH_2$—$CH_2$—$CH_2$—;
(39) $L^2$ represents —O—$(CR^3R^4)_q$—C(O)$NR^5$—$(CH_2)_q$—;
(40) q represents 0, 1, 2 or 3;
(41) q represents 3;
(42) q represents 2;
(43) q represents 1;
(44) q represents 0;
(45) $R^3$ and $R^4$ both represent hydrogen;
(46) $R^5$ represents hydrogen;

(47) R⁵ represents methyl;
(48) R² represents halo, C₁₋₆alkyl, C₂₋₆alkenyl, C₂₋₆alkynyl, carboxy, C₁₋₆alkoxy, cyano, oxo, fluoroC₁₋₆alkyl, hydroxy, amino, N—C₁₋₄alkylamino or N,N-di-C₁₋₄alkylamino;
(49) R² represents halo, C₁₋₆alkyl, C₁₋₆alkoxy, cyano, fluoroC₁₋₆alkyl or hydroxy; R² represents fluoro, chloro, methyl, methoxy, difluoromethyl, trifluoromethyl, cyano or hydroxy;
(50) R² represents fluoro, chloro, difluoromethyl, trifluoromethyl or cyano;
(51) R² represents methyl, hydroxy, methoxy or trifluoromethyl;
(52) R² represents a monocyclic 4, 5, 6 or 7 membered heterocyclic ring which comprises 1, 2 or 3 heteroatoms independently selected from O, N or S and wherein the heterocyclic ring is optionally substituted with 1, 2 or 3 substituents selected from R⁶;
(53) R² represents a monocyclic 6 membered heterocyclic ring which comprises 1 or 2 heteroatoms independently selected from O, N or S and wherein the heterocyclic ring is optionally substituted with 1, 2 or 3 substituents selected from R⁶;
(54) R² represents piperidinyl or piperazinyl optionally substituted with 1, 2 or 3 substituents selected from R⁶;
(55) R² represents piperidinyl optionally substituted with 1, 2 or 3 substituents selected from R⁶;
(56) R² represents piperazinyl optionally substituted with 1, 2 or 3 substituents selected from R⁶;
(57) R² represents a monocyclic 5 or 6 membered heteroaryl ring which comprises 1, 2, 3 or 4 heteroatoms independently selected from O, N or S and wherein the heteroaryl ring is optionally substituted with 1, 2 or 3 substituents selected from R⁶;
(58) R² represents a monocyclic 5 membered heteroaryl ring which comprises 1 or 2 heteroatoms independently selected from O, N or S and wherein the heteroaryl ring is optionally substituted with 1, 2 or 3 substituents selected from R⁶;
(59) R² represents pyrazolyl or imidazolyl optionally substituted with 1, 2 or 3 substituents selected from R⁶;
(60) r represents 0, 1 or 2;
(61) r represents 0 or 1;
(62) r represents 0;
(63) r represents 1;
(64) r represents 2;
(65) r represents 3;
(66) R⁶ represents C₁₋₆alkyl, C₃₋₆cycloalkyl, C₂₋₆alkanoyl, fluoroC₁₋₆alkyl, C₁₋₆alkylsulphonyl or oxo;
(67) R⁶ represents methyl, ethyl, cyclopropyl, acetyl, pentanoyl, cyclopropylcarbonyl, methylsulphonyl, trifluoromethyl or oxo;
(68) R⁶ represents methyl;
(69) R⁶ represents acetyl;
(70) R⁶ represents oxetan-3-ylcarbonyl;
(71) R⁹ and R¹⁰, identically or differently on each occurrence, represent hydrogen or methyl;
(72) R⁹ and R¹⁰ both represent hydrogen.

Particular novel compounds of Formula (I) include, but are not limited to, the following compounds:

6-[4-(4-fluorobenzyl)piperazin-1-yl]-3-(trifluoromethyl)-7,8-dihydro[1,2,4]triazolo[4,3-b]pyridazine;
6-[4-(1H-indol-3-yl)-3,6-dihydropyridin-1(2H)-yl]-3-(trifluoromethyl)-7,8-dihydro[1,2,4]triazolo[4,3-b]pyridazine;
6-[4-(1H-indol-3-yl)piperidin-1-yl]-3-(trifluoromethyl)-7,8-dihydro[1,2,4]triazolo[4,3-b]pyridazine;
6-(4-{4-[3-(4-acetylpiperazin-1-yl)propoxy]phenyl}piperidin-1-yl)-3-(trifluoromethyl)-7,8-dihydro[1,2,4]triazolo[4,3-b]pyridazine;
6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine;
6-[4-(3-fluorobenzyl)piperazin-1-yl]-3-(trifluoromethyl)-7,8-dihydro[1,2,4]triazolo[4,3-b]pyridazine;
6-[4-(3-chlorobenzyl)piperazin-1-yl]-3-(trifluoromethyl)-7,8-dihydro[1,2,4]triazolo[4,3-b]pyridazine;
3-(trifluoromethyl)-6-{4-[3-(trifluoromethyl)benzyl]piperazin-1-yl}-7,8-dihydro[1,2,4]triazolo[4,3-b]pyridazine;
6-[4-(2,3-difluorobenzyl)piperazin-1-yl]-3-(trifluoromethyl)-7,8-dihydro[1,2,4]triazolo[4,3-b]pyridazine;
6-{4-[2-(difluoromethyl)-5-fluorobenzyl]piperazin-1-yl}-3-(trifluoromethyl)-7,8-dihydro[1,2,4]triazolo[4,3-b]pyridazine;
6-[4-(1H-indol-3-ylmethyl)piperazin-1-yl]-3-(trifluoromethyl)-7,8-dihydro[1,2,4]triazolo[4,3-b]pyridazine;
6-{4-[(5-fluoro-1H-indol-3-yl)methyl]piperazin-1-yl}-3-(trifluoromethyl)-7,8-dihydro[1,2,4]triazolo[4,3-b]pyridazine;
3-({4-[3-(trifluoromethyl)-7,8-dihydro[1,2,4]triazolo[4,3-b]pyridazin-6-yl]piperazin-1-yl}methyl)-1H-indole-5-carbonitrile;
4-(4-fluorophenyl)-1-[3-(trifluoromethyl)-7,8-dihydro[1,2,4]triazolo[4,3-b]pyridazin-6-yl]piperidin-4-ol;
6-(4-{4-[2-(1-methyl-1H-pyrazol-5-yl)ethoxy]phenyl}piperidin-1-yl)-3-(trifluoromethyl)-7,8-dihydro[1,2,4]triazolo[4,3-b]pyridazine;
6-(4-{4-[2-(1-methyl-1H-pyrazol-5-yl)ethoxy]phenyl}piperazin-1-yl)-3-(trifluoromethyl)-7,8-dihydro[1,2,4]triazolo[4,3-b]pyridazine;
6-[4-(1H-pyrrolo[2,3-b]pyridin-3-yl)-3,6-dihydropyridin-1(2H)-yl]-3-(trifluoromethyl)-7,8-dihydro[1,2,4]triazolo[4,3-b]pyridazine;
6-[4-(1H-pyrrolo[2,3-b]pyridin-3-yl)piperidin-1-yl]-3-(trifluoromethyl)-7,8-dihydro[1,2,4]triazolo[4,3-b]pyridazine;
N-(2-methoxyethyl)-N-methyl-2-(4-{1-[3-(trifluoromethyl)-7,8-dihydro[1,2,4]triazolo[4,3-b]pyridazin-6-yl]piperidin-4-yl}phenoxy)acetamide;
N,N-dimethyl-2-(4-{1-[3-(trifluoromethyl)-7,8-dihydro[1,2,4]triazolo[4,3-b]pyridazin-6-yl]piperidin-4-yl}phenoxy)acetamide;
N-(2-hydroxyethyl)-N-methyl-2-(4-{1-[3-(trifluoromethyl)-7,8-dihydro[1,2,4]triazolo[4,3-b]pyridazin-6-yl]piperidin-4-yl}phenoxy)acetamide;
N-butyl-N-methyl-2-(4-{1-[3-(trifluoromethyl)-7,8-dihydro[1,2,4]triazolo[4,3-b]pyridazin-6-yl]piperidin-4-yl}phenoxy)acetamide;
N-(2-methoxyethyl)-N-methyl-4-(4-{1-[3-(trifluoromethyl)-7,8-dihydro[1,2,4]triazolo[4,3-b]pyridazin-6-yl]piperidin-4-yl}phenoxy)butanamide;
N-(2-hydroxyethyl)-N-methyl-4-(4-{1-[3-(trifluoromethyl)-7,8-dihydro[1,2,4]triazolo[1,2,4]triazolo[4,3-b]pyridazin-6-yl]piperidin-4-yl}phenoxy)butanamide;
6-(4-{4-[2-(4-pentanoylpiperazin-1-yl)ethoxy]phenyl}piperidin-1-yl)-3-(trifluoromethyl)-7,8-dihydro[1,2,4]triazolo[4,3-b]pyridazine;
6-[4-(4-{2-[4-(methylsulfonyl)piperazin-1-yl]ethoxy}phenyl)piperidin-1-yl]-3-(trifluoromethyl)-7,8-dihydro[1,2,4]triazolo[4,3-b]pyridazine;
6-(4-{4-[3-(4-pentanoylpiperazin-1-yl)propoxy]phenyl}piperidin-1-yl)-3-(trifluoromethyl)-7,8-dihydro[1,2,4]triazolo[4,3-b]pyridazine;

6-[4-(4-{3-[4-(methylsulfonyl)piperazin-1-yl]
propoxy}phenyl)piperidin-1-yl]-3-(trifluoromethyl)-7,8-
dihydro[1,2,4]triazolo[4,3-b]pyridazine;
6-(4-{4-[3-(4-acetylpiperazin-1-yl)propoxy]
phenyl}piperazin-1-yl)-3-(trifluoromethyl)-7,8-dihydro
[1,2,4]triazolo[4,3-b]pyridazine;
6-(4-{4-[3-(4-pentanoylpiperazin-1-yl)propoxy]
phenyl}piperazin-1-yl)-3-(trifluoromethyl)-7,8-dihydro
[1,2,4]triazolo[4,3-b]pyridazine;
6-[4-(4-{3-[4-(methylsulfonyl)piperazin-1-yl]
propoxy}phenyl)piperazin-1-yl]-3-(trifluoromethyl)-7,8-
dihydro[1,2,4]triazolo[4,3-b]pyridazine;
6-(4-{4-[2-(4-acetylpiperazin-1-yl)ethoxy]
phenyl}piperazin-1-yl)-3-(trifluoromethyl)-7,8-dihydro
[1,2,4]triazolo[4,3-b]pyridazine;
6-(4-{4-[2-(4-pentanoylpiperazin-1-yl)ethoxy]
phenyl}piperazin-1-yl)-3-(trifluoromethyl)-7,8-dihydro
[1,2,4]triazolo[4,3-b]pyridazine;
6-[4-(4-{2-[4-(methylsulfonyl)piperazin-1-yl]
ethoxy}phenyl)piperazin-1-yl]-3-(trifluoromethyl)-7,8-
dihydro[1,2,4]triazolo[4,3-b]pyridazine;
6-{4-[4-(4,4,4-trifluorobutoxy)phenyl]piperidin-1-yl}-3-
(trifluoromethyl)-7,8-dihydro[1,2,4]triazolo[4,3-b]py-
ridazine;
4-{4-[2-(1-methyl-1H-pyrazol-5-yl)ethoxy]phenyl}-1-[3-
(trifluoromethyl)-7,8-dihydro[1,2,4]triazolo[4,3-b]py-
ridazin-6-yl]piperidin-4-ol;
1-methyl-4-[2-(4-{1-[3-(trifluoromethyl)-7,8-dihydro[1,2,
4]triazolo[4,3-b]pyridazin-6-yl]piperidin-4-yl}phenoxy)
ethyl]piperazin-2-one;
6-(4-{4-[2-(1H-imidazol-1-yl)ethoxy]phenyl}piperazin-1-
yl)-3-(trifluoromethyl)-7,8-dihydro[1,2,4]triazolo[4,3-b]
pyridazine;
6-(4-{4-[2-(2-ethyl-1H-imidazol-1-yl)ethoxy]
phenyl}piperazin-1-yl)-3-(trifluoromethyl)-7,8-dihydro
[1,2,4]triazolo[4,3-b]pyridazine;
3-(trifluoromethyl)-6-[4-(4-{2-[3-(trifluoromethyl)-1H-
pyrazol-1-yl]ethoxy}phenyl)piperazin-1-yl]-7,8-dihydro
[1,2,4]triazolo[4,3-b]pyridazine;
6-(4-{4-[2-(1H-imidazol-1-yl)ethoxy]phenyl}piperidin-1-
yl)-3-(trifluoromethyl)-7,8-dihydro[1,2,4]triazolo[4,3-b]
pyridazine;
6-(4-{4-[2-(2-ethyl-1H-imidazol-1-yl)ethoxy]
phenyl}piperidin-1-yl)-3-(trifluormethyl)-7,8-dihydro[1,
2,4]triazolo[4,3-b]pyridazine;
6-(4-{4-[2-(3,5-dimethyl-1H-pyrazol-1-yl)ethoxy]
phenyl}piperidin-1-yl)-3-(trifluoromethyl)-7,8-dihydro
[1,2,4]triazolo[4,3-b]pyridazine;
3-(trifluoromethyl)-6-[4-(4-{2-[3-(trifluoromethyl)-1H-
pyrazol-1-yl]ethoxy}phenyl)piperidin-1-yl]-7,8-dihydro
[1,2,4]triazolo[4,3-b]pyridazine;
4-{4-[2-(4-acetylpiperazin-1-yl)ethoxy]phenyl}-1-[3-(trif-
luoromethyl)-7,8-dihydro[1,2,4]triazolo[4,3-b]pyridazin-
6-yl]piperidin-4-ol;
1-ethyl-4-[2-(4-{1-[3-(trifluoromethyl)-7,8-dihydro[1,2,4]
triazolo[4,3-b]pyridazin-6-yl]piperidin-4-yl}phenoxy)
ethyl]piperazin-2-one;
1-cyclopropyl-4-[2-(4-{1-[3-(trifluoromethyl)-7,8-dihydro
[1,2,4]triazolo[4,3-b]pyridazin-6-yl]piperidin-4-
yl}phenoxy)ethyl]piperazin-2-one;
6-(4-{4-[2-(4-acetyl-1,4-diazepan-1-yl)ethoxy]
phenyl}piperidin-1-yl)-3-(trifluoromethyl)-7,8-dihydro
[1,2,4]triazolo[4,3-b]pyridazine;
(3R)-1,3-dimethyl-4-[2-(4-{1-[3-(trifluoromethyl)-7,8-di-
hydro[1,2,4]triazolo[4,3-b]pyridazin-6-yl]piperidin-4-
yl}phenoxy)ethyl]piperazin-2-one;
(3S)-1,3-dimethyl-4-[2-(4-{1-[3-(trifluoromethyl)-7,8-dihy-
dro[1,2,4]triazolo[4,3-b]pyridazin-6-yl]piperidin-4-
yl}phenoxy)ethyl]piperazin-2-one;
6-[4-(4-{2-[(3R)-4-acetyl-3-methylpiperazin-1-yl]
ethoxy}phenyl)piperidin-1-yl]-3-(trifluoromethyl)-7,8-
dihydro[1,2,4]triazolo[4,3-b]pyridazine;
6-[4-(4-{2-[(3S)-4-acetyl-3-methylpiperazin-1-yl]
ethoxy}phenyl)piperidin-1-yl]-3-(trifluoromethyl)-7,8-
dihydro[1,2,4]triazolo[4,3-b]pyridazine;
(R)-6-(4-{4-[2-(4-acetylpiperazin-1-yl)propoxy]
phenyl}piperidin-1-yl)-3-(trifluoromethyl)-7,8-dihydro
[1,2,4]triazolo[4,3-b]pyridazine;
(S)-6-(4-{4-[2-(4-acetylpiperazin-1-yl)propoxy]
phenyl}piperidin-1-yl)-3-(trifluoromethyl)-7,8-dihydro
[1,2,4]triazolo[4,3-b]pyridazine;
(S)-1-methyl-4-[1-methyl-2-(4-{1-[3-(trifluoromethyl)-7,8-
dihydro[1,2,4]triazolo[4,3-b]pyridazin-6-yl]piperidin-4-
yl}phenoxy)ethyl]piperazin-2-one;
(R) 1-methyl-4-[1-methyl-2-(4-{1-[3-(trifluoromethyl)-7,8-
dihydro[1,2,4]triazolo[4,3-b]pyridazin-6-yl]piperidin-4-
yl}phenoxy)ethyl]piperazin-2-one;
and pharmaceutically acceptable salts thereof.

A suitable pharmaceutically-acceptable salt of a compound of the Formula (I) is, for example, an acid-addition salt of a compound of the Formula I, for example an acid-addition salt with an inorganic or organic acid such as hydrochloric, hydrobromic, sulphuric, trifluoroacetic, citric, maleic, naphthalene-1,5-disulfonic, toluene-4-sulfonic or fumaric acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

In one embodiment of the invention, there is provided a pharmaceutically-acceptable salt of a compound of the Formula (I), wherein the salt is an acid-addition salt with an organic acid selected from maleic, naphthalene-1,5-disulfonic, toluene-4-sulfonic and fumaric acid.

The compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a carboxy group is, for example, an in vivo cleavable ester thereof. An in vivo cleavable ester of a compound of the Formula (I) containing a carboxy group is, for example, a pharmaceutically-acceptable ester which is cleaved in the human or animal body to produce the parent acid. Suitable pharmaceutically-acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically-acceptable pro-drug of a compound of the Formula (I) that possesses a hydroxy group is, for example, an in vivo cleavable ester or ether thereof.

An in vivo cleavable ester or ether of a compound of the Formula (I) containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N-[di-$C_{1-4}$alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$C_{1-4}$alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula (I) that possesses a carboxy group is, for example, an in vivo cleavable amide thereof, for example an amide formed with an amine such as ammonia, a $C_{1-4}$alkylamine such as methylamine, a di-$C_{1-4}$alkylamine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically-acceptable pro-drug of a compound of the Formula (I) that possesses an amino group is, for example, an in vivo cleavable amide derivative thereof. Suitable pharmaceutically-acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$)alkylpiperazin-1-ylmethyl.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

In one embodiment of the invention, there is provided an amphorous form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine.

As stated hereinbefore, certain compounds of Formula (I) may exist in crystalline form and exhibit polymorphism. According to the present invention there is therefore provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, or a pharmaceutically acceptable salt thereof.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A, which has an X-ray powder diffraction pattern with at least one specific peak at a 2θ value of about 4.9° when measured using CuKa radiation, more particularly wherein said value may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A, which has an X-ray powder diffraction pattern with at least one specific peak at a 2θ value of about 18.4° when measured using CuKa radiation, more particularly wherein said value may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A, which has an X-ray powder diffraction pattern with at least two specific peaks at 2θ values of about 4.9° and 18.4° when measured using CuKa radiation, more particularly wherein said values may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A, which has an X-ray powder diffraction pattern with specific peaks at 2θ values of about 4.9, 6.1, 7.5, 12.2, 13.5, 16.6, 18.4, 19.8, 20.0 and 24.6° when measured using CuKa radiation, more particularly wherein said values may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A, which has an X-ray powder diffraction pattern substantially the same as the X-ray powder diffraction pattern shown in Figure A when measured using CuKa radiation.

As stated hereinbefore, certain compounds of Formula (I) may exist in a solvated form. According to the present invention there is therefore provided a solvated form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A ethylacetate solvate, which has an X-ray powder diffraction pattern with at least one specific peak at a 2θ value of about 4.1° when measured using CuKa radiation, more particularly wherein said value may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A ethylacetate solvate, which has an X-ray powder diffraction pattern with at least one specific peak at a 2θ value of about 20.5° when measured using CuKa radiation, more particularly wherein said value may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A ethylacetate solvate, which has an X-ray powder diffraction pattern with at least two specific peaks at 2θ values of about 4.1° and 20.5° when measured using CuKa radiation, more particularly wherein said values may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A ethylacetate solvate, which has an X-ray powder diffraction pattern with specific peaks at 2θ values of about 4.1, 8.2, 12.1, 16.7, 17.8, 18.2, 18.7, 19.0, 20.5 and 24.6° when measured using CuKa radiation, more particularly wherein said values may be plus or minus 0.5° 2θ.

In one embodiment of the present invention, there is provided a crystalline form of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine, Form A ethylacetate solvate, which has an X-ray powder diffraction pattern substantially the same as the X-ray powder diffraction pattern shown in Figure B when measured using CuKa radiation.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A, which has an X-ray powder diffraction pattern with at least one specific peak at a 2θ value of about 4.7° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A, which has an X-ray powder diffraction pattern with at least one specific peak at a 2θ value of about 9.5° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A, which has an X-ray powder diffraction pattern with at least two specific peaks at 2θ values of about 4.7° and 9.5° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A, which has an X-ray powder diffraction pattern with specific peaks at 2θ values of about 4.7, 9.5, 12.0, 14.3, 17.4, 18.8, 19.0, 21.7, 22.5 and 22.7° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A, which has an X-ray powder diffraction pattern substantially the same as the X-ray powder diffraction pattern shown in Figure C when measured using CuKa radiation.

As stated hereinbefore, certain compounds of Formula (I) may exist in a solvated form, for example a hydrated form. According to the present invention there is therefore provided a hydrated form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A hydrate, which has an X-ray powder diffraction pattern with at least one specific peak at a 2θ value of about 17.8° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A hydrate, which has an X-ray powder diffraction pattern with at least one specific peak at a 2θ value of about 8.9° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A hydrate, which has an X-ray powder diffraction pattern with at least two specific peaks at 2θ values of about 17.8° and 8.9° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A hydrate, which has an X-ray powder diffraction pattern with specific peaks at 2θ values of about 4.8, 8.9, 15.5, 17.8, 19.0, 19.7, is 21.6, 22.0, 22.3 and 23.9° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, Form A hydrate, which has an X-ray powder diffraction pattern substantially the same as the X-ray powder diffraction pattern shown in Figure D when measured using CuKa radiation.

As stated hereinbefore, certain compounds of Formula (I) may form acid addition salts. In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2, 4]triazolo[4,3-b]pyridazine napadisylate which has an X-ray powder diffraction pattern with at least one specific peak at a 2θ value of about 19.8° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate which has an X-ray powder diffraction pattern with at least one specific peak at a 2θ value of about 19.4° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate which has an X-ray powder diffraction pattern with at least two specific peaks at 2θ values of about 19.8° and 19.4° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate which has an X-ray powder diffraction pattern with specific peaks at 2θ values of about 8.7, 9.4, 11.9, 13.8, 18.9, 19.4, 19.8, 20.3, 21.3 and 22.4° when measured using CuKa radiation, more particularly wherein is said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate which has an X-ray powder diffraction pattern substantially the same as the X-ray powder diffraction pattern shown in Figure K when measured using CuKa radiation.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate which has an X-ray powder diffraction pattern with at least one specific peak at a 2θ value of about 23.1° when measured using CuKa radiation, more particularly wherein said value may be plus or minus 0.5°2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate which has an X-ray powder diffraction pattern with at least one specific peak at a 2θ value of about 17.5° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate which has an X-ray powder diffraction pattern with at least two specific peaks at 2θ values of about 23.1° and 17.5° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate which has an X-ray powder diffraction pattern with specific peaks at 2θ values of about 6.5, 12.8, 13.6, 14.9, 17.5, 20.1, 21.9, 22.1, 23.1 and 23.5° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate which has an X-ray powder diffraction pattern substantially the same as the X-ray powder diffraction pattern shown in Figure M when measured using CuKa radiation.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate which has an X-ray powder diffraction pattern with at least one specific peak at a 2θ value of about 20.3° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate which has an X-ray powder diffraction pattern with at least one specific peak at a 2θ value of about 22.0° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate which has an X-ray powder diffraction pattern with at least two specific peaks at 2θ values of about 20.3° and 22.0° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate which has an X-ray powder diffraction pattern with specific peaks at 2θ values of about 11.9, 13.5, 16.8, 19.4, 19.6, 20.3, 22, 24.9, 26.5 and 27.2° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate which has an X-ray powder diffraction pattern substantially the same as the X-ray powder diffraction pattern shown in Figure O when measured using CuKa radiation.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate which has an X-ray powder diffraction pattern with at least one specific peak at a 2θ value of about 20.4° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate which has an X-ray powder diffraction pattern with at least one specific peak at a 2θ value of about 21.1° when measured using CuKa radiation, more particularly wherein said value may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate which has an X-ray powder diffraction pattern with at least two specific peaks at 2θ values of about 20.4° and 21.1° when measured using CuKa radiation, more particularly wherein said values may be plus or minus 0.5° 2θ.

In one embodiment of the present invention, there is provided a crystalline form of 6-(4-{4-[2-(4-acetylpiperazin-1- yl)ethoxy]phenyl}piperidin-1-yl)-3-(trifluoromethyl)-7,8-dihydro[1,2,4]triazolo[4,3-b]pyridazine fumarate which has an X-ray powder diffraction pattern with specific peaks at 2θ values of about 9.4, 15.2, 17.9, 18.5, 19.9, 20.4, 21.1, 21.9, 23.7 and 24.3° when measured using CuKa radiation, more particularly wherein said values may be plus or minus 0.5° 2θ.

In one embodiment of the present invention, there is provided a crystalline form of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate which has an X-ray powder diffraction pattern substantially the same as the X-ray powder diffraction pattern shown in Figure Q when measured using CuKa radiation.

When it is stated that the present invention relates to a crystalline form the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2θ values of the X-ray powder diffraction pattern may vary slightly from one machine to another or from one sample to another, and so the values quoted are not to be construed as absolute.

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

Generally, a measurement error of a diffraction angle in an X-ray powder diffractogram is approximately plus or minus 0.5° 2-theta, and such degree of a measurement error should be taken into account when considering the X-ray powder diffraction pattern in Figures A, B, C, D, I, K, M, O and Q and when reading Tables A, B, C, D, E, F, G, H and I. Furthermore, it should be understood that intensities might fluctuate depending on experimental conditions and sample preparation (preferred orientation). Preferred orientation occurs when there is a tendency for the crystal morphology (shape) to exhibit a particular orientation such as acicular (needle-like), resulting in a non-random orientation of the crystals when sampled for XRPD analysis. This can result in differences in relative intensity of peaks.

Preparation of Compounds of Formula (I)

Certain processes for the synthesis of compounds of Formula (I) are provided as a further feature of the invention. Thus, according to a further aspect of the invention there is provided a process for the preparation of a compound of Formula (I) or a pharmaceutically acceptable salt thereof, which comprises a process (a), (b), (c), (d), (e) or (f) wherein, unless otherwise defined, the variables are as defined hereinbefore for compounds of Formula (I):

(a) when Y in Formula (I) is N, CH or COH, reduction of a compound of Formula (II):

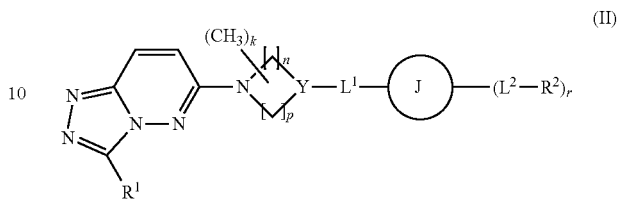

(b) when Y in Formula (I) is CH and $L^1$ is a direct bond, reduction of a compound of Formula (III):

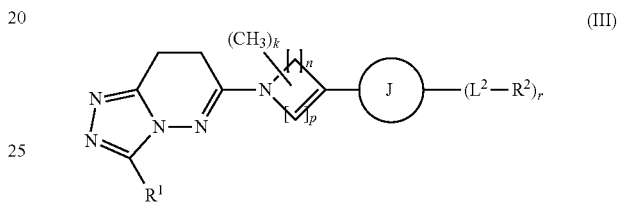

(c) when Y in Formula (I) is N and $L^1$ is —$(CH_2)_t$—, reaction of a compound of Formula (IV) with a compound of Formula (V): or

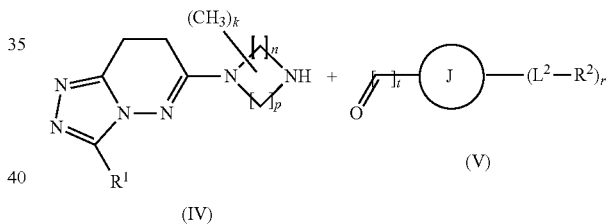

(d) when Y in Formula (I) is C, ----- represents a double bond, $L^1$ is a direct bond and J is indolyl or pyrrolopyridinyl, reaction of a compound of Formula (VI) with a compound of Formula (VII) wherein X represents CH or N:

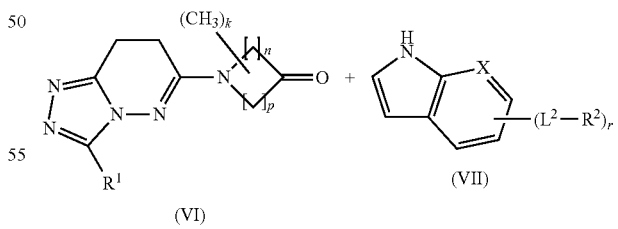

(e) when $R^2$ is a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$, $L^2$ is a direct bond, —$(CR^3R^4)_r$—, —$C(O)N(R^5)$—$(CH_2)_q$—, —$NR^5C(O)$—$(CH_2)_q$—; —$C(O)$—$(CH_2)_q$—, —$O$—$(CR^9R^{10})_q$—, —$O$—$(CR^3R^4)_q$—$NR^5$—$(CH_2)_q$—, or —O—$(CR^3R^4)_q$—$C(O)NR^5$—$(CH_2)_q$— and q is 2, 3 or 4, reaction of a compound of Formula (XVIII) with a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$:

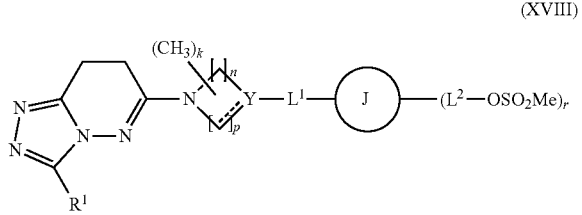

(XVIII)

(f) when $R^2$ is a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$; $L^2$ is —O—$(CR^9R^{10})_q$—; and
q is 2, 3, or 4;
wherein the final occurrence of —$CR^9R^{10}$— represents —$CHR^{9a}$—; and
wherein $R^{9a}$ represents methyl, ethyl, isopropyl, cyclopropyl or methoxymethyl; reaction of a compound of a compound of Formula (XIX) with a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$:

example dichloromethane, a suitable acid, for example acetic acid, and at a suitable temperature, for example 0 to 50° C., more suitably at about room temperature.

Process (d)—compounds of Formula (VI) may be reacted with compounds of Formula (VII) in the presence of a base, for example potassium hydroxide, a suitable solvent, for example methanol, and at a suitable temperature, for example 50 to 100° C., more suitably about 65° C.

Process (e)—compounds of Formula (XVIII) may be reacted with a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$ in the presence of a base, for example DIPEA, a suitable solvent, for example DMF, and at a suitable temperature, for example 0 to 100° C., more suitably about 20° C.

Process (f)—compounds of Formula (XIX) may be reacted with a monocyclic 4, 5, 6 or 7 membered heterocyclic ring which comprises 1 N atom and optionally comprises 1 or 2 further heteroatoms independently selected from O, N or S and wherein the heterocyclic ring is optionally substituted with 1, 2 or 3 substituents selected from $R^6$ in the presence of a suitable acid, for example acetic acid, a suitable reducing agent, for example sodium triacetoxyborohydride, a suitable catalyst, for example $MgSO_4$, a suitable solvent, for example THF, and at a suitable temperature, for example 0 to 50° C., more suitably at about room temperature.

A process for the preparation of compounds of Formula (I) may comprise converting a compound of Formula (I) into another compound of Formula (I) using standard chemical reactions well-known to those skilled in the art to produce another compound of the invention. Similarly, a process for the preparation of precursor compounds of Formula (II) may

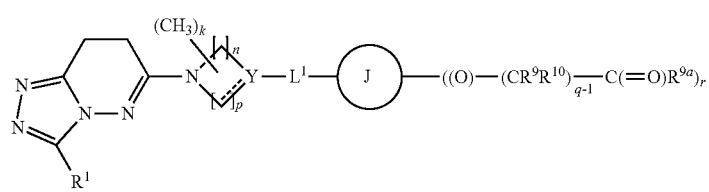

(XIX)

and thereafter, if necessary:
(i) converting a compound of Formula (I) into another compound of Formula (I);
(ii) removing any protecting groups;
(iii) separating a racemic mixture into separate enantiomers;
(iv) preparing a pharmaceutically acceptable salt thereof; and/or
(v) preparing a crystalline form thereof.

Specific reaction conditions for processes (a) to (f) above are as follows:

Processes (a) and (b)—compounds of Formula (II) and (III) may be reduced in the presence of a suitable metal catalyst, for example palladium on carbon, ammonium formate and a suitable solvent, for example ethanol, by heating to a suitable temperature, for example 50 to 100° C., more suitably about 78° C.

Process (c)—compounds of Formula (IV) may be reacted with compounds of Formula (V) in the presence of a suitable reducing agent, for example (Polystyrylmethyl)trimethylammonium cyanoborohydride, a suitable solvent, for comprise converting a compound of Formula (II) into another compound of Formula (II). Chemical conversions of this type are well known to those skilled in the art and may include functional group interconversions such as hydrolysis, hydrogenation, hydrogenolysis, oxidation or reduction, and/or further functionalisation by standard reactions such as amide or metal-catalysed coupling, or nucleophilic displacement reactions. Examples of such conversions are described, for instance, in *Comprehensive Organic Chemistry*, Volume 2, p 3, D. Barton and D. Ollis Eds, Pergamon, 1979, *Comprehensive Functional Group Transformations*, A. R. Katritzky, O. Meth-Cohn, and C. W. Rees Eds., Pergamon, 1995, and by various authors in *Houben-Weyl, Methods of Organic Chemistry*, Verlag Chemie, various years, and references therein.

A process for the manufacture of compounds of Formula (I) in the form of a single enantiomer may comprise separating a racemic compound of the invention into separate enantiomers.

Examples of suitable methods for separating the enantiomers of a racemic compound are well known to those skilled in the art and include chromatography using a suitable chiral stationary phase; or conversion of a racemic mixture into diastereomeric derivatives, separation of the mixture of diastereomeric derivatives into two single diastereomers, and regeneration of a separate single enantiomer from each separate single diastereomer; or selective chemical reaction of one of the enantiomers of a racemic compound (kinetic resolution) using a diastereoselective reaction catalysed by a microbiological agent or an enzyme.

Alternatively, compounds of the invention in the form of a single enantiomer may be prepared by using chiral starting materials to carry out one of the processes described in the preceding sections.

It will be appreciated by a person skilled in the art that it may be necessary/desirable to protect any sensitive groups in the compounds in some of the processes/reactions mentioned herein. The instances where protection is necessary or desirable, and suitable methods for providing such protection are known to those skilled in the art. Conventional protecting groups may be used in accordance with standard practice (for illustration see P. G. M. Wuts and T. W. Green, *Protective Groups in Organic Synthesis*, 4th Edition, John Wiley and Sons, 2002). Thus, if reactants include groups such as amino, carboxy or hydroxy it may be desirable to protect the group in some of the reactions mentioned herein.

Any protecting groups utilised in the processes described herein may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The protecting groups may be removed at any convenient stage in the synthesis using conventional techniques well known in the chemical art.

Precursor compounds of Formula (II) may be prepared by reacting a compound of Formula (VIII), wherein G is a suitable leaving group such as halogen, for example chloro, with a compound of Formula (IX), wherein all other variables are as defined hereinbefore for compounds of Formula (I) unless otherwise defined:

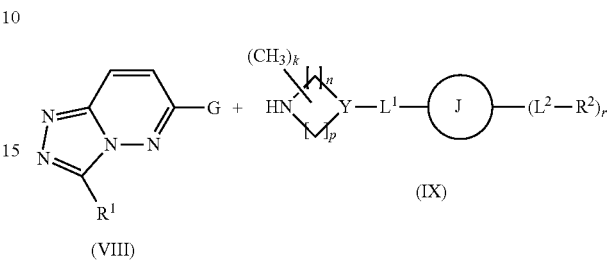

and thereafter, if necessary:
(i) converting a compound of Formula (II) into another compound of Formula (II);
(ii) removing any protecting groups; and/or
(iii) separating a racemic mixture into separate enantiomers.

The above reaction may be carried out by combining compounds of Formulae (VIII) and (IX) in a suitable solvent, for example dimethylformamide or dimethylacetamide, at a suitable temperature, for example between 25° C. and 250° C., more particularly between 50° C. and 150° C., in the presence of a suitable base, for example diisopropylethylamine.

Precursor compounds of Formula (III) and (VI) may be prepared according to Scheme 1 below wherein G is a suitable leaving group such as halogen, for example chloro, and all other variables are as defined hereinbefore for compounds of Formula (I):

Scheme 1

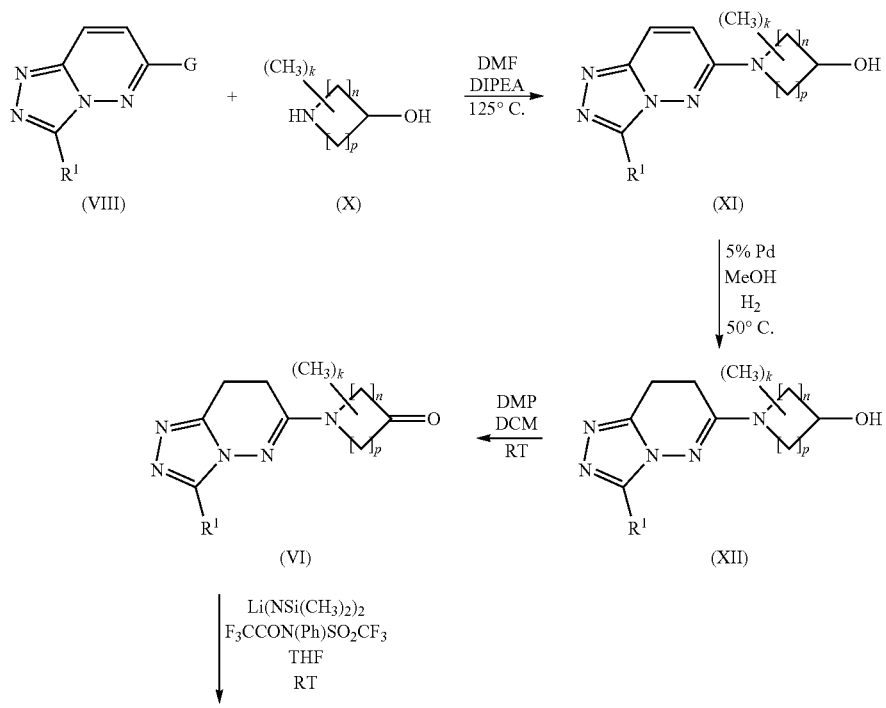

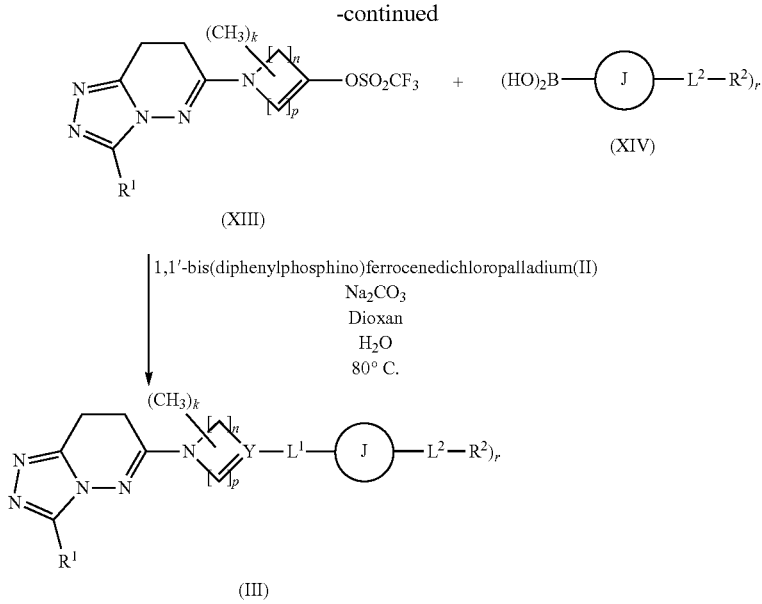

Precursor compounds of Formula (IV) may be prepared according to Scheme 2 below wherein G is a suitable leaving group such as halogen, for example chloro, P$^1$ represents a suitable protecting group, for example N-tert-butoxycarbonyl, and all other variables are as defined hereinbefore for compounds of Formula (I):

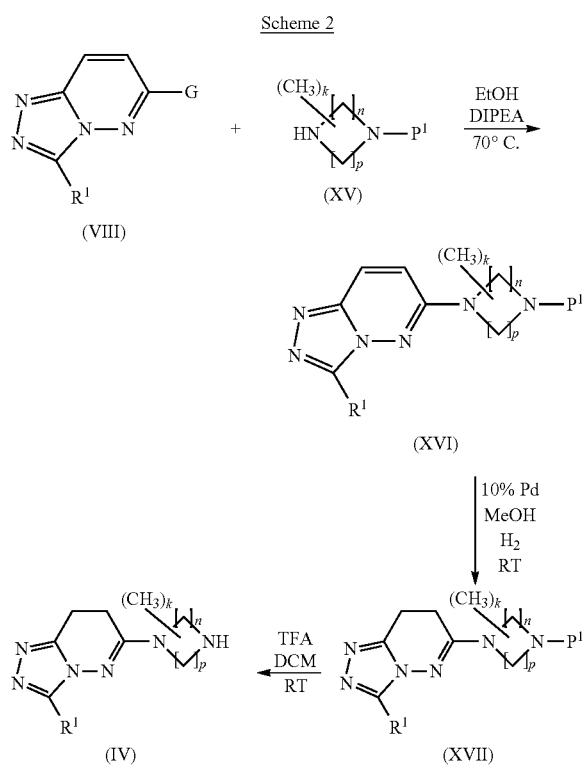

Compounds of Formula (XVIII) wherein L$^2$ is a direct bond, —(CR$^3$R$^4$)$_t$—, —C(O)N(R$^5$)—(CH$_2$)$_q$—, —NR$^5$C(O)—(CH$_2$)$_q$—, —C(O)—(CH$_2$)$_q$—, —O—(CR$^9$R$^{10}$)$_q$—, —O—(CR$^3$R$^4$)$_q$—NR$^5$—(CH$_2$)$_q$—, or —O—(CR$^3$R$^4$)$_q$—C(O)NR$^5$—(CH$_2$)$_q$— and q is 2, 3 or 4 may be prepared by reacting a compound of Formula (XX):

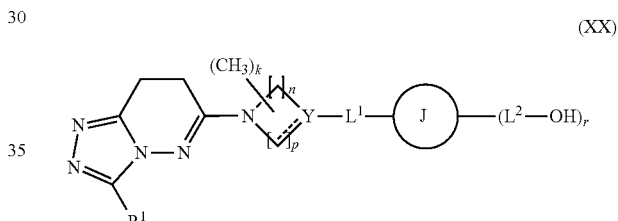

with a solution of methanesulfonyl chloride in a suitable solvent, for example DCM, in the presence of a suitable base, for example triethylamine, and at a suitable temperature, for example 0° C. under nitrogen.

Compounds of Formula (XIX) wherein L$^2$ is —O—(CR$^9$R$^{10}$)$_q$—, q is 2, 3, or 4, the final occurrence of —CR$^9$R$^{10}$— represents —CHR$^{9a}$— and R$^{9a}$ represents methyl, ethyl, isopropyl, cyclopropyl or methoxymethyl may be prepared by reacting a compound of Formula (XX) with a compound of formula Cl—(CR$^9$R$^{10}$)$_q$-1-C(=O)R$^{9a}$ in a suitable solvent, for example DMA, in the presence of a suitable base, for example potassium carbonate, and at a suitable temperature, for example 50 to 150° C., more preferably about 100° C.

Compounds of Formula (VIII) may be made by methods well-known to those skilled in the art including methods according to or analogous to methods described in the chemical literature, for instance as described in in W. L. Mosby, *Heterocyclic Compounds*, Vol. 15 Part 1 and Part 2, *Systems with Bridgehead Nitrogen*, Interscience, 1961; R. N. Castle, *Heterocyclic Compounds*, Vol. 27, *Condensed Pyridazines*, Wiley, 1973; and *Heterocyclic Chemistry*, Vol. 35, Condensed Pyrazines, G. W. H. Cheeseman and R. F. Cookson, Wiley, 1979 and references therein. In particular, compounds of Formula (VIII) wherein G represents chloro and R$^1$ represents trifluoromethyl may be obtained as described in Monatsh. Chem. (1972) 103(6), 1591-603.

Compounds of Formulae (V), (IX), (XIV) and (XX) may be made by methods well-known to those skilled in the art including methods according to or analogous to methods described in the chemical literature, for instance J. R. Malpass, *Aliphatic and Cyclic Amines in Comprehensive Organic Chemistry*, Volume 2, p 3, D. Barton and D. Ollis Eds, Pergamon, 1979, J. M. J. Gladych and D. Hartley, *Polyfunctional Amines in Comprehensive Organic Chemistry*, Volume 2, p 61, D. Barton and D. Ollis Eds, Pergamon, 1979; *Houben-Weyl Methods of Organic Chemistry*, Vol E 23 e *Cyclic Compounds I* (1999) to Vol E 23 j *Cyclic Compounds VI* (2000) and references therein and modified as required by functional group transformations well-known to those skilled in the art including methods according to or analogous to methods described in the chemical literature, for instance Comprehensive Functional Group Transformations, A. R. Katritzky, O. Meth-Cohn, and C. W. Rees Eds., Pergamon, 1995, and references therein. Compounds of Formulae (V) and (IX) may also be made by methods according to or analogous to those described herein for the preparation of Examples of the present invention.

Compounds of Formulae (VII), (X) and (XV) are available from commercial sources or may be prepared by methods well-known to those skilled in the art including methods according to or analogous to methods described in the chemical literature.

Biological Assays

The ability of compounds to reduce Androgen Receptor (AR) numbers was assessed in a cell based immuno-fluorescence assay using the LNCaP prostate epithelial cell line.

a) LNCaP Androgen Receptor Down-Regulation Cell Assay

This immunofluorescence end point assay measures the ability of a test compound to down-regulate and reduce measured levels of the AR in the LNCaP prostate carcinoma cell line (LNCaP clone FGC (CRL-1740) obtained from the American Type Culture Collection (ATCC)).

LNCaP cells were cultured in Growth Medium (phenol red free Roswell Park Memorial Institute (RPMI) 1640 (Invitrogen Code no. 11835-063) containing 2 mM L-Glutamine (Invitrogen Code no. 25030-024) and 1% (v/v) Penicillin/Streptomycin (10000 units/ml Penicillin and 10000 μg/ml of Streptomycin utilising penicillin G (sodium salt) and streptomycin sulphate: prepared in normal saline, Invitrogen Code no. 15140122) and 10% (v/v) foetal bovine serum (FBS)) in a 5% $CO_2$ air incubator at 37° C. Cells for assay were harvested from T175 stock flasks by washing once in PBS (phosphate buffered saline, pH 7.4) (Invitrogen Code no. 14190-094) and harvested using 5 mls of 1× Trypsin/ethylaminediaminetetraacetic acid (EDTA) (10× Trypsin-EDTA, 5.0 g/L Trypsin, 2.0 g/L of EDTA.4Na and 8.5 g/L of NaCl, without Phenol Red, Invitrogen Code no. 15400-054) diluted in PBS solution. A 5 ml volume of Growth Medium was added to each flask (as above except that 5% (v/v) charcoal stripped FBS (HyClone Code no. SH30068.03) was included instead of 10% (v/v) FBS). Cells were syringed at least twice using a sterile 18 G×1.5" (1.2×40 mm) broad gauge needle and cell density was measured using a haemocytometer. Cells were further diluted in Growth Medium plus 5% (v/v) charcoal stripped FBS and seeded at a density of $6.5 \times 10^3$ cells per well (in 90 ul) into transparent, black, tissue culture treated 96 well plates (Packard, No. 6005182).

Test data reported herein was generated using two different compounds preparation and dosing methods. In method (1) a 10 mM compound stock solution in 100% (v/v) DMSO was serially diluted in 4-fold steps in 100% (v/v) DMSO using a Thermo Scientific Matrix SerialMate. The diluted compounds were then further diluted 1 in 30 in assay media using a Thermo Scientific Matrix PlateMate and a 10 μl aliquot of this dilution was dosed to cells manually using a multi-channel pipette. In method (2) starting with a 10 mM compound stock solution, the Labcyte Echo 550 was used to generate a compound concentration response set diluted in 30 μl of assay media. The Echo 550 is a liquid handler that uses acoustic technology to perform direct microplate-to-microplate transfers of DMSO compound solutions. The system can be programmed to transfer volumes as low as 2.5 nL in multiple increments between microplates and in so doing generates a serial dilution of compound which is then back-filled to normalise the DMSO concentration across the dilution range. A 10 μl volume of diluted compound is then dosed to cells using a Thermo Scientific Matrix PlateMate.

Plates were incubated overnight at 37° C., 5% $CO_2$. Wells were then dosed with compound prepared by one of the 2 methods above and further incubated for 20-22 hours at 37° C., 5% $CO_2$. Plates were fixed by the addition of 20 μl of 10% (v/v) formaldehyde solution (in PBS) to each well (final formaldehyde conc.=1.67% (v/v)) and left at room temperature for 10 mins. This fixative solution was removed and cells were washed with 250 μl of PBS/0.05% (v/v) Tween 20 (PBST) using an automated plate washer. This process was then repeated twice more.

Immunostaining was performed at room temperature. Cells were permeabilised by the addition of 35 μl of PBS containing 0.5% Tween 20 and incubated for 1 hour at room temperature. Permeabilisation solution was removed and cells were washed with 250 μl of PBST using an automated plate washer. This process was then repeated twice more. 35 μl of Blocking Solution (PBST containing 3% (w/v) Marvel dried skimmed milk (Nestle)) was added to each well and plates were incubated at room temperature for a minimum of 1 hour. Following removal of the Blocking Solution with a plate washer, 35 μl of mouse anti-human AR monoclonal antibody (clone AR441) (immunogen—synthetic peptide corresponding to amino acids 229-315 of the human AR coupled to keyhole limpet hemocyanin, DAKO, Code No. M3562), diluted 1:500 in Blocking Solution, was added to each well and incubated for 1 hour. Then this primary antibody solution was removed from the wells followed by 3×100 μl PBST washes using a plate washer. Then 35 μl of Alexa-Fluor 488 goat anti-mouse IgG secondary antibody (Invitrogen, Code No. A-11001), diluted 1:500 in Blocking Solution, was added to each well. Henceforth, wherever possible, plates were protected from light exposure. The plates were incubated for 1 hour and then the secondary antibody solution was removed from the wells followed by 3×100 ul PBST washes using a plate washer. Then 50 μl of PBST was added to each well and plates were covered with a black plate seal and stored at 4° C. before being read. Plates were read within six hours of completing the immunostaining.

The Green Fluorescent AR-associated signal in each well was measured using an Acumen Explorer HTS Reader (TTP Labtech Ltd., Cambridge). AR-associated fluorescence emission can be detected at 530 nm following excitation at 488 nm. The instrument is a laser-scanning fluorescence microplate cytometer which samples the well at regular intervals and uses threshold algorithms to identify all fluorescent intensities above the solution background without the need to generate and analyse an image. These fluorescent objects can be quantified and provide a measure of the AR levels in cells. Fluorescence dose response data obtained with each compound was exported into a suitable software package (such as Origin) to perform curve fitting analysis. Down-regulation of AR levels was expressed as an $IC_{50}$ value. This was determined by calculation of the concentration of compound that was required to give a 50% reduction of the AR signal.

The following table discloses biological data for compounds of the present invention using the aforementioned down-regulation assay.

| Example Number | Androgen Receptor Down-regulation Assay (a) $IC_{50}/\mu M$ |
| --- | --- |
| 1 | 6 |
| 2 | 3.2 |
| 3 | 1.2 |
| 4.1 | 1.2 |
| 5.1 | 1.8 |
| 6 | 4 |
| 7 | 2.9 |
| 8 | 2.7 |
| 9 | 4.1 |
| 10 | 1 |
| 11 | 8.6 |
| 12 | 3.4 |
| 13 | >11 |
| 14 | >15 |
| 15 | 0.94 |
| 16 | 3.2 |
| 17 | 4.4 |
| 18 | 3.2 |
| 19 | 2.9 |
| 20 | 4.1 |
| 21 | 26 |
| 22 | 0.46 |
| 23 | 1.3 |
| 24 | 2.5 |
| 25 | 0.93 |
| 26 | 1.5 |
| 27 | 0.67 |
| 28 | 1 |
| 29 | 10 |
| 30 | 6.7 |
| 31 | 18 |
| 32 | 20 |
| 33 | 7.8 |
| 34 | 23 |
| 35 | 2.3 |
| 36 | 4.5 |
| 37 | 1.7 |
| 38 | 7.8 |
| 39 | 4.8 |
| 40 | 1.5 |
| 41 | 2.9 |
| 42 | 0.66 |
| 43 | 1 |
| 44 | 0.55 |
| 45 | 12 |
| 46 | 1.5 |
| 47 | 1.4 |
| 48 | 0.7 |
| 49 | 0.045 |
| 50 | 0.76 |
| 51 | 0.25 |
| 52 | 0.32 |
| 53 | 0.18 |
| 54 | 0.14 |
| 55 | 0.18 |
| 56 | 0.38 | b) Androgen Receptor—Ligand Binding Domain Competitive Binding Assay

The ability of compounds to bind to isolated Androgen Receptor Ligand binding domain (AR-LBD) was assessed in competition assays using a Fluorescence Polarisation (FP) detection end-point.

For the FP test, an assay test kit was purchased from Invitrogen and used to measure compound binding to the isolated rat AR-LBD which shares 100% sequence identity to the human AR-LBD. The Invitrogen PolarScreen™ Androgen Receptor Competitor Assay Red (Product Code No. PV4293), is a fluorescence polarisation (FP)—based competition assay which measures if test compound can displace a fluorescently-labelled tracer compound. If the test compound binds to the AR-LBD it will prevent the formation of the receptor/tracer complex, which will result in a low polarisation value. If the test compound does not bind the receptor, it will have no effect on formation of the receptor/tracer complex, and the measured polarisation value of the tracer will remain high.

The assay was performed as follows with all reagent additions carried out using the Thermo Scientific Matrix PlateMate:

1. Acoustic dispense 120 nl of the test compound into a black low volume 384 well assay plates.
2. Volumes of reagents are added to give the following final concentrations of assay components:—0.5 mM DTT, 2 nM fluormone, 12 nM AR-LBD in the Invitrogen Assay Buffer
3. Dispense 15 µl of the assay mix into each well of the assay plate
4. Cover the assay plate to protect the reagents from light and evaporation, and incubate at room temperature for 4-6 hours.
5. Excite at 530 nM and measure the fluorescent emission signal of each well at 590 nm in FP mode using the BMG PheraSTAR or other suitable plate reader.

Compounds were dosed directly from a compound source microplate containing serially diluted compound (4 wells containing 10 mM, 0.1 mM, 1 µM and 10 nM final compound respectively) to an assay microplate using an Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then backfilled to normalise the DMSO concentration across the dilution range. In total 120 nL of compound plus DMSO was added to each well and compounds tested in a 12-point concentration response format over a final compound concentration range of 100, 30, 10, 3, 1, 0.3, 0.1, 0.03, 0.01, 0.003, 0.001, 0.0001 µM, respectively.

FP dose response data obtained with each compound was exported into a suitable software package (such as Origin) to perform curve fitting analysis. Competitive AR binding may be expressed as an $IC_{50}$ value. This is determined by calculation of the concentration of compound that is required to give a 50% reduction in tracer compound binding to AR-LBD.

The following table discloses biological data for certain compounds of the present invention using the aforementioned androgen receptor ligand binding domain competitive binding assay.

| Example Number | Androgen Receptor Ligand Binding Domain Competitive Binding Assay (b) $IC_{50}/\mu M$ |
| --- | --- |
| 4.1 | 23.82 |
| 5.1 | 22.86 |
| 37 | 61.93 |
| 51 | 30.3 |

Pharmaceutical Compositions and Methods of Treatment Comprising Compounds of Formula (I)

According to a further aspect of the invention there is provided a pharmaceutical composition which comprises a compound of the Formula (I), or a pharmaceutically acceptable salt thereof, as defined hereinbefore in association with a pharmaceutically-acceptable diluent or carrier. The composition may be in a form suitable for oral administration, for example as a tablet or capsule; for parenteral injection (including intravenous, subcutaneous, intramuscular, intravascular or infusion) as a sterile solution, suspension or emulsion; for topical administration as an ointment or cream; or for rectal administration as a suppository. For example, a composition suitable for pre-clinical in vivo intravenous administration comprises 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine formulated as a solution in 20/20/60 DMA/PEG400/HP-β-CD (dimethylacetamide/polyethylene glycol 400/hydroxypropyl-β-cyclodextrin) (20% w/v) in purified water at a concentration of up to 50 mg/mL corresponding to 96.23 μmol/mL. Alternatively, a composition suitable for oral administration comprises 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine formulated as a solution in 20% w/v SBE-β-CD (sulfobutyl ether-β-cyclodextrin) in purified water, adjusted to pH4 at concentrations in the range of 0.1 to 28 mg/mL of parent compound, corresponding to 0.19 to 53.89 μmol/mL.

For oral administration in a clinical setting, a compound of the invention would preferably be administered in tablet form. For example, the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compound of Formula (I) will normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient. For example, 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine could be administered to a human patient at a dose of 75 to >3000 mg BID (twice a day), more particularly about 280 mg BID, and 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine could be administered to a human patient at a dose of 30 to 240 mg BID, more particularly about 60 mg BID, or 65 to 730 mg UID (once a day), more particularly about 145 mg UID. The predicted human doses of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine and 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine are based on a standard human weighing 70 kg and BID doses are per dose (i.e. half the total daily dose).

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

We have found that the compounds defined in the present invention are effective modulators of the androgen receptor. Accordingly, the compounds of the present invention are expected to be potentially useful agents in the treatment of diseases or medical conditions mediated alone or in part by the androgen receptor. Compounds of the invention induce down-regulation of the androgen receptor and/or may be selective agonists, partial agonists, antagonists or partial antagonists of the androgen receptor.

The compounds of the invention may be useful in the treatment of androgen receptor-associated conditions. An "androgen receptor-associated condition," as used herein, denotes a condition or disorder which can be treated by modulating the function or activity of an androgen receptor in a subject, wherein treatment comprises prevention, partial alleviation or cure of the condition or disorder. Modulation may occur locally, for example, within certain tissues of the subject, or more extensively throughout a subject being treated for such a condition or disorder.

There is therefore provided a compound of Formula (I), or a pharmaceutically acceptable salt thereof, for use as a medicament.

In one embodiment, compounds of the present invention may be administered to animals, for example humans, for the treatment of a variety of conditions and disorders, including, but not limited to the treatment of androgen-sensitive diseases or disorders whose progress or onset is aided by activation of the androgen receptor or androgen receptor modulators. Examples of particular androgen-sensitive diseases or disorders include, but are not limited to, androgen-sensitive cancers such as prostate cancer and other cancers composed of malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; and androgen sensitive disorders such as benign prostatic hyperplasia and prostamegaly, acne (acne vulgaris), seborrhoea, hirsutism (hypertrichosis), androgenic alopecia and male pattern baldness, precocious puberty, endometriosis, polycystic ovarian syndrome, treatment of spermatogenesis, conteracting preeclampsia, eclampsia of pregnancy and preterm labor, treatment of premenstrual syndrome, treatment of vaginal dryness, sexual perversion, virilisation, and the like. Compounds of the invention may also be used to improve ovulation in a domestic animal.

In another embodiment, compounds of the present invention may be administered to animals, for example humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular-24 dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; age related decreased testosterone levels in men, male menopause, hypogonadism, male hormone replacement, male and female sexual dysfunction (e.g., erectile dysfunction, decreased sex drive, sexual well-being, decreased libido), urinary incontinence, male and female contraception, hair loss, and the enhancement of bone and muscle performance/strength.

The term treatment is also intended to include prophylactic treatment.

In addition, the conditions, diseases, and maladies collectively referenced to as "Syndrome X" or Metabolic Syndrome as detailed in Johannsson J. Clin. Endocrinol. Metab., 82, 727-34 (1997), may be treated employing the compounds of the invention.

In one embodiment the androgen-receptor associated conditions include prostate cancer, benign prostatic hyperplasia and prostamegaly, acne (acne vulgaris), seborrhoea, hirsutism (hypertrichosis), androgenic alopecia and male pattern baldness, precocious puberty, polycystic ovarian syndrome, sexual perversion, virilisation, and the like. Compounds of the invention may also be used to improve ovulation in a domestic animal.

Accordingly, the present invention relates to a method of treating any one of the aforementioned androgen-receptor associated condition in a warm-blooded animal, such as man, in need of such treatment which comprises administering to said animal an effective amount of a compound of the Formula (I), or a pharmaceutically acceptable salt thereof, as defined hereinbefore.

According to a further aspect the present invention relates to the use of compound of Formula (I), or a pharmaceutically acceptable salt thereof, as hereinbefore defined in the manufacture of a medicament for the treatment of any one of the aforementioned androgen-receptor associated conditions.

According to another aspect of the present invention there is provided a compound of the Formula (I), or a pharmaceutically acceptable salt or pro-drug thereof, as defined hereinbefore for use in the treatment of any one of the aforementioned androgen-receptor associated conditions.

According to another aspect of the present invention there is provided a compound of the Formula (I), or a pharmaceutically acceptable salt thereof, as defined hereinbefore for use in a method of treatment of the animal body, such as the human body, by therapy.

According to a further aspect of the invention there is provided the use of a compound of the Formula (I), or a pharmaceutically acceptable salt or pro-drug thereof, as defined hereinbefore in the manufacture of a medicament for use in the production of an anti-androgenic effect in a warm-blooded animal such as man.

According to a further feature of this aspect of the invention there is provided a method for producing an anti-androgenic effect in a warm-blooded animal, such as man, in need of such treatment which comprises administering to said animal an effective amount of a compound of the Formula (I), or a pharmaceutically acceptable salt thereof, as defined hereinbefore.

The term "anti-androgenic effect" is used herein to mean the inhibition and/or down regulation of androgen receptors.

According to a further aspect of the invention there is provided the use of a compound of the Formula (I), or a pharmaceutically acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a compound of the Formula (I), or a pharmaceutically acceptable salt thereof, as defined hereinbefore.

According to an additional feature of this aspect of the invention there is provided a method of treating androgen-sensitive cancers in a warm-blooded animal, such as man, in need of such treatment which comprises administering to said animal an effective amount of a compound of the Formula (I), or a pharmaceutically acceptable salt thereof, as defined hereinbefore.

According to a further feature of the invention there is provided a compound of the Formula (I), or a pharmaceutically acceptable salt thereof, as defined hereinbefore for use in the treatment of androgen-sensitive cancers.

According to a further feature of the invention there is provided the use of a compound of the Formula (I), or a pharmaceutically acceptable salt thereof, as defined hereinbefore in the manufacture of a medicament for use in the treatment of androgen-sensitive cancers.

According to an additional feature of this aspect of the invention there is provided a method of treating prostate cancer in a warm-blooded animal, such as man, in need of such treatment which comprises administering to said animal an effective amount of a compound of the Formula (I), or a pharmaceutically acceptable salt thereof, as defined hereinbefore. In one embodiment of this aspect of the invention, the prostate cancer is hormone resistant.

According to a further aspect of the invention there is provided a method for treating prostate cancer which comprises administering to a warm-blooded animal, such as man, in need thereof a therapeutically effective amount of a compound of the Formula (I), or a pharmaceutically acceptable salt thereof, as defined in claim 1.

According to a further feature of the invention there is provided a compound of the Formula (I), or a pharmaceutically acceptable salt thereof, as defined hereinbefore for use in the treatment of prostate cancer, more particularly hormone resistant prostate cancer.

According to a further feature of the invention there is provided the use of a compound of the Formula (I), or a pharmaceutically acceptable salt thereof, as defined hereinbefore in the manufacture of a medicament for use in the treatment of prostate cancer, more particularly hormone resistant prostate cancer.

Hormone resistant prostate cancer (HRPC) arises when the prostate cancer progresses to the hormone-independent and castrate resistant stage of the disease.

According to an additional feature of this aspect of the invention there is provided a method of treating any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation; in a warm-blooded animal, such as man, in need of such treatment which comprises administering to said animal an effective amount of a compound of the Formula (I), or a pharmaceutically acceptable salt thereof, as defined hereinbefore.

According to a further feature of the invention there is provided a compound of the Formula (I), or a pharmaceutically acceptable salt thereof, as defined hereinbefore for use in the treatment of any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation.

According to a further feature of the invention there is provided the use of a compound of the Formula (I), or a pharmaceutically acceptable salt thereof, as defined hereinbefore in the manufacture of a medicament for use in the treatment of any one of the following conditions: benign prostatic hyperplasia, prostamegaly, acne (acne vulgaris), seborrhoea, hirsutism (hypertrichosis), androgenic alopecia and male pattern baldness, precocious puberty, polycystic ovarian syndrome, sexual perversion, or virilisation.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The compounds of Formula (I) defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), LHRH antagonists or LHRH agonists (for example goserelin, leuprorelin and buserelin), progestogens (for example megestrol acetate), aromatase inhibitors (for example as anastrozole, letrozole, vorazole and exemestane), inhibitors of 5α-reductase such as finasteride and androgen-synthesis inhibitors such as those that inhibit the 17-α-hydroxylase enzyme (for example abiraterone);

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-

{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in is International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

According to this aspect of the invention there is provided a combination suitable for use in the treatment of prostate cancer, in particular HRPC, comprising a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, and:

an androgen-synthesis inhibitor (for example abiraterone);
an endothelin receptor antagonist (for example zibotentan (ZD4054) or atrasentan); or
an LHRH agonist (for example goserelin, leuprorelin or buserelin).

Therefore in a further aspect of the invention there is provided a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with:

an androgen-synthesis inhibitor (for example abiraterone);
an endothelin receptor antagonist (for example zibotentan (ZD4054) or atrasentan); or
an LHRH agonist (for example goserelin, leuprorelin or buserelin).

According to a further aspect of the invention there is provided a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with an androgen-synthesis inhibitor. A suitable androgen-synthesis inhibitor is, for example, abiraterone According to a further aspect of the invention there is provided a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with an endothelin receptor antagonist. A suitable endothelin receptor antagonist is, for example, zibotentan (ZD4054) or atrasentan.

According to a further aspect of the invention there is provided a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with an LHRH agonist. A suitable LHRH agonist is, for example, goserelin, leuprorelin or buserelin.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with:
 an androgen-synthesis inhibitor (for example abiraterone);
 an endothelin receptor antagonist (for example zibotentan (ZD4054) or is atrasentan); or
 an LHRH agonist (for example goserelin, leuprorelin or buserelin), and in association with a pharmaceutically acceptable diluent or carrier.

According to a further aspect of the invention there is provided a pharmaceutical composition which comprises a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with:
 an androgen-synthesis inhibitor (for example abiraterone);
 an endothelin receptor antagonist (for example zibotentan (ZD4054) or atrasentan); or
 an LHRH agonist (for example goserelin, leuprorelin or buserelin); and in association with a pharmaceutically acceptable diluent or carrier for use in the treatment of prostate cancer, in particular HRPC.

According to another feature of the invention there is provided the use of a compound of the Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with
 an androgen-synthesis inhibitor (for example abiraterone);
 an endothelin receptor antagonist (for example zibotentan (ZD4054) or atrasentan); or
 an LHRH agonist (for example goserelin, leuprorelin or buserelin);
in the manufacture of a medicament for use in the treatment of prostate cancer, in particular HRPC, in a warm-blooded animal, such as man.

According to another feature of the invention there is provided a compound of the Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with
 an androgen-synthesis inhibitor (for example abiraterone);
 an endothelin receptor antagonist (for example zibotentan (ZD4054) or is atrasentan); or
 an LHRH agonist (for example goserelin, leuprorelin or buserelin);
for use in the treatment of prostate cancer, in particular HRPC, in a warm-blooded animal, such as man.

Therefore in an additional feature of the invention, there is provided a method of the treatment of prostate cancer, in particular HRPC, in a warm-blooded animal, such as man, in need of such treatment which comprises administering to said animal an effective amount of a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with:
 an androgen-synthesis inhibitor (for example abiraterone);
 an endothelin receptor antagonist (for example zibotentan (ZD4054) or atrasentan); or
 an LHRH agonist (for example goserelin, leuprorelin or buserelin).

According to a further aspect of the present invention there is provided a kit comprising a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in combination with:
 an androgen-synthesis inhibitor (for example abiraterone);
 an endothelin receptor antagonist (for example zibotentan (ZD4054) or atrasentan); or
 an LHRH agonist (for example goserelin, leuprorelin or buserelin).

According to a further aspect of the present invention there is provided a kit comprising:
a) a compound of Formula I as defined hereinbefore, for example 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof, in a first unit dosage form;
b) an androgen-synthesis inhibitor (for example abiraterone), an endothelin receptor is antagonist (for example zibotentan (ZD4054) or atrasentan) or an LHRH agonist (for example goserelin, leuprorelin or buserelin); in a second unit dosage form; and
c) container means for containing said first and second dosage forms.

EXAMPLES

The invention will now be illustrated in the following Examples in which, generally:
(i) temperatures are given in degrees Celsius (° C.); unless stated otherwise, operations were carried out at room or ambient temperature, that is, at a temperature in the range of 18 to 25° C.;
(ii) organic solutions were dried over anhydrous magnesium sulfate or anhydrous sodium sulfate; evaporation of solvent was carried out using a rotary evaporator under reduced pressure (600 to 4000 Pascals; 4.5 to 30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and/or analytical LC-MS, and reaction times where given are for illustration only.
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 400 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; bs, broad singlet;
(viii) chemical symbols have their usual meanings; SI units and symbols are used;
(ix) Mass spectra (MS) and LC-MS data were generated on an LC-MS system where the HPLC component comprised generally either an Agilent 1100, Waters Alliance HT (2790 & 2795) equipment or an HP1100 pump and Diode Array with CTC autosampler and was run on a Phenomenex Gemini C18 5 μm, 50×2 mm column (or similar) eluting with either acidic eluent (for example, using a gradient between 0-95% water/acetonitrile with 5% is of a 1% formic acid in 50:50 water:acetonitrile (v/v) mixture), or basic eluent (for example, using a gradient between 0-95% water/acetonitrile with 5% of a 0.1% 880 Ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the (M+H)+ for positive ion mode and (M−H)− for negative ion mode. In Examples 5.5 to 5.9, the HPLC component of the LC-MS was performed on a Kromasil C18 column (150 mm×4.6 mm, 5 μm) or a Zorbax SB-aqua column (150 mm×4.6 mm, 3.5 m) eluting with an appropriate aqueous methanol and acetonitrile gradient buffered with ammonium acetate, with UV (230 nm and 254 nm) and using +ve and −ve multimode ionisation (ES (Electrospray Ionisation) and APCI (Atmospheric Pressure Chemical Ionisation));

(x) unless stated otherwise compounds containing an asymmetrically substituted carbon and/or sulfur atom have not been resolved;

(xi) any microwave reactions were carried out in either a Biotage Optimizer EXP, or a CEM Explorer microwave;

(xii) preparative high performance liquid chromatography (HPLC) was performed on a Gilson instrument using the following conditions:

Column: C18 reversed-phase silica, for example, Waters Abridge', 5 μm silica, 19×100 mm, or 30×100 mm, using decreasingly polar solvent mixtures as eluent (decreasing ratio of Solvent A to Solvent B)
Solvent A: Water with 1% ammonium hydroxide
Solvent B: Acetonitrile
Flow rate: 28 ml/min or 61 ml/min
Gradient: Tailored to suit each compound—generally 7-10 min in length
Wavelength: 254 nm (xiii) Strong cation exchange (SCX) chromatography was performed on pre-packed cartridges (for example, ISOLUTE SCX-2 propyl sulfonic acid-based cartridges supplied by International Sorbent Technology), using a basic eluent (for example, 2M ammonia in methanol);

(xiv) The X-ray powder diffraction spectra were determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffract+ software. For Examples 5.5 to 5.9, the X-ray powder diffraction spectra were determined by mounting a sample of the crystalline material on a Panalytical stainless steel holder. The sample was spun at 120 revolutions per minute (to improve counting statistics) and irradiated with X-rays generated by a copper long-fine focus tube operated at 40 kV and 30 mA with a wavelength of 1.5406 angstroms. The X-rays from the source were passed through a 0.02 rad soller slit, a fixed 1° divergence slit, and 2° anti-scatter slit. A PIXcel detector detected the diffracted X-rays after the X-rays passed through a Ni Kβ filter, 0.04 rad soller slit, and 8 mm secondary anti-scatter slit. The sample was scanned in the range 5 degrees to 40 degrees 2-theta in theta-theta mode with step size of 0.01 deg 2-theta and scan speed 0.1 deg 2-theta per second. The total scan time was 6 minutes 20 seconds. Control and data capture was by means of X'Pert data collector and analysed using X'Pert High Score software.

The % relative intensities of the peaks are categorised in Table 1 below.

TABLE 1

| % Relative Intensity* | Definition |
| --- | --- |
| 25-100 | vs (very strong) |
| 10-25 | s (strong) |
| 3-10 | m (medium) |
| 1-3 | w (weak) |

*The relative intensities are derived from diffractograms measured with fixed slits Analytical Instrument: Bruker D4 or Panalytical.

(xv) Differential Scanning Calorimetry (DSC) was performed using a TA Instruments Q1000 DSC. Typically less than 5 mg of material contained in a standard aluminium pan fitted with a lid was heated over the temperature range 25° C. to 325° C. at a constant heating rate of 10° C. per minute. A purge gas using nitrogen was used—flow rate 100 per minute. For Examples 5.5 to 5.9, DSC was performed using a TA Instruments Q2000 and a purge gas nitrogen flow rate of 50 ml per minute.

(xvi) the following abbreviations have been used herein, where necessary:—

| | |
| --- | --- |
| DCM | dichloromethane |
| DIAD | diisopropyl azodicarboxylate |
| DIPEA | N,N-diisopropylethylamine |
| DMA | N,N-dimethyl acetamide |
| DMF | N,N-dimethylformamide |
| DMP | Dess-Martin periodinane (1,1,1-triacetoxy-1,1-dihydro-1,2-benziodoxol-3(1H)-one) |
| DMSO | dimethylsulphoxide |
| EtOAc | ethyl acetate |
| EtOH | ethanol |
| HATU | O-(7-azabenzotriazol-1-yl)-N,N,N',N'-tetramethyluronium Hexafluorophosphate |
| HPLC | high performance liquid chromatography |
| MeOH | methanol |
| MTBE | methyl tertiarybutyl ether |
| RT | room temperature |
| SCX | strong cation exchange |
| TFA | trifluoroacetic acid |
| THF | tetrahydrofuran |

Example 1

Preparation of 6-[4-(4-fluorobenzyl)piperazin-1-yl]-3-(trifluoromethyl)-7,8-dihydro[1,2,4]triazolo[4,3-b]pyridazine

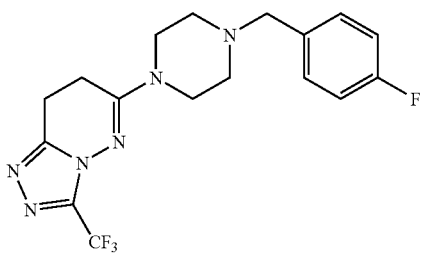

(Polystyrylmethyl)trimethylammonium cyanoborohydride (4.1 mmol/g, 125 mg, 0.510 mmol) was added to 6-(piperazin-1-yl)-3-(trifluoromethyl)-7,8-dihydro-[1,2,4]triazolo[4,3-b]pyridazine (100 mg, 0.365 mmol) and 4-fluorobenzaldehyde (63 mg, 0.510 mmol) in 10% acetic acid in DCM (2.2 mL). The resulting mixture was stirred at ambient temperature for 16 hours, then the resin removed by filtration and the solvents evaporated. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to give 6-[4-(4-fluorobenzyl)piperazin-1-yl]-3-(trifluoromethyl)-7,8-dihydro[1,2,4]triazolo[4,3-b]pyridazine (85 mg, 61%) as a solid. 1H NMR (399.9 MHz, DMSO-d6) δ 2.44 (4H, m), 2.88 (2H, t), 3.13 (2H, t), 3.52 (6H, m), 7.16 (2H, m), 7.36 (2H, m); m/z=383 [M+H]+.

The 6-piperazin-1-yl-3-(trifluoromethyl)-7,8-dihydro[1,2,4]triazolo[4,3-b]pyridazine used as starting material was prepared as follows:—

Preparation of tert-butyl 4-[3-(trifluoromethyl)-[1,2,4]triazolo[4,3-b]pyridazin-6-yl]piperazine-1-carboxylate A mixture of tert-butyl piperazine-1-carboxylate (8.29 g, 44.5 mmol) and ethanol (90 mL) was added to a mixture of DIPEA (9.16 mL, 52.6 mmol) and 6-chloro-3-(trifluoromethyl)-[1,2,4]triazolo[3,4-f]pyridazine (obtained as described in Monatsh. Chem. (1972) 103(6), 1591-603) (9.0 g, 40.4 mmol) in ethanol (90 mL). The mixture was heated at 70° C. for 11 hours and then allowed to cool to ambient temperature to give a precipitate. The is precipitate was collected by filtration, washed with chilled ethanol and then with water, and dried under vacuum to afford tert-butyl 4-[3-(trifluoromethyl)-[1,2,4]triazolo[4,3-b]pyridazin-6-yl]piperazine-1-carboxylate (13.64 g, 90.6%) as a white solid that was used without further purification.

1H NMR (300.132 MHz, DMSO-d6) d 1.43 (s, 9H), 3.48 (m, 4H), 3.62 (m, 4H), 7.58 (d, 1H), 8.28 (d, 1H); m/z=373 (M+H)+.

Preparation of tert-butyl 4-[3-(trifluoromethyl)-7,8-dihydro[1,2,4]triazolo[4,3-b]pyridazin-6-yl]piperazine-1-carboxylate 10% Palladium on carbon (0.563 g, 0.53 mmol) and tert-butyl 4-(3-(trifluoromethyl)-[1,2,4]triazolo[4,3-b]pyridazin-6-yl)piperazine-1-carboxylate (1.97 g, 5.29 mmol) were stirred in MeOH (30 mL) under an atmosphere of hydrogen at atmospheric temperature and pressure for 3 days. The catalyst was removed by filtration and the solvents evaporated. The residues were re-dissolved in MeOH (50 mL), 5% palladium on carbon (0.4 g, 0.09 mmol) was added and the mixture was stirred under an atmosphere of hydrogen at 50° C. and 5 Bar pressure until complete conversion was obtained. The catalyst was removed by filtration, washed with MeOH then DCM/MeOH and the solvent was evaporated to afford tert-butyl 4-(3-(trifluoromethyl)-7,8-dihydro-[1,2,4]triazolo[4,3-b]pyridazin-6-yl)piperazine-1-carboxylate (1.880 g, 9%) as a solid.

1H NMR (399.9 MHz, DMSO-d6) δ 1.36 (9H, s), 2.84 (2H, t), 3.08 (2H, t), 3.35 (4H, m), 3.46 (4H, m); m/z=375 [M+H]+.

Preparation of 6-piperazin-1-yl-3-(trifluoromethyl)-7,8-dihydro[1,2,4]triazolo[4,3-b]pyridazine TFA (5 mL) was added to tert-butyl 4-[3-(trifluoromethyl)-7,8-dihydro[1,2,4]triazolo[4,3-b]pyridazin-6-yl]piperazine-1-carboxylate (1.88 g, 5.02 mmol) in DCM (5 mL). The resulting solution was stirred at ambient temperature for 30 minutes then added to a SCX column. The desired product was eluted from the column using 2M ammonia in methanol and the solvents were evaporated to dryness to give 6-(piperazin-1-yl)-3-(trifluoromethyl)-7,8-dihydro-[1,2,4]triazolo[4,3-b]pyridazine (1.360 g, 99%) as a solid.

1H NMR (399.9 MHz, DMSO-d6) δ 1.12 (1H, br s), 2.75 (4H, m), 2.88 (2H, m), 3.13 (2H, m), 3.43 (4H, m); m/z=275 [M+H]+.

Example 2

Preparation of 6-[4-(1H-indol-3-yl)-5,6-dihydropyridin-1(2H)-yl]-3-(trifluoromethyl)-7,8-dihydro-[1,2,4]triazolo[4,3-b]pyridazine

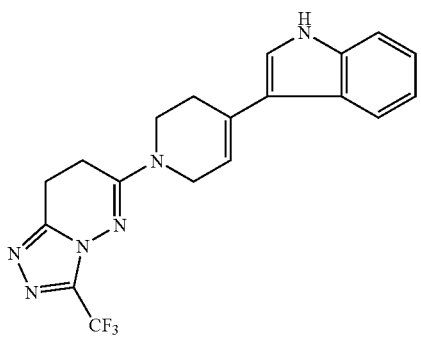

Potassium hydroxide (156 mg, 2.79 mmol) was added to 1-[3-(trifluoromethyl)-7,8-dihydro-[1,2,4]triazolo[4,3-b]pyridazin-6-yl]piperidin-4-one (200 mg, 0.70 mmol) and 1H-indole (90 mg, 0.77 mmol) in MeOH (3 mL). The resulting mixture was stirred at 65° C. for 20 hours. The reaction mixture was evaporated to dryness then quenched with saturated aqueous ammonium chloride (0.5 mL), diluted with water (50 mL) and extracted with ethyl acetate (2×50 mL). The combined organic layers were washed with saturated brine (25 mL), dried over MgSO4, filtered and evaporated to afford crude product. The crude product was purified by flash silica chromatography, elution gradient 0 to 5% MeOH in DCM. Pure fractions were evaporated to dryness to afford 6-[4-(1H-indol-3-yl)-5,6-dihydropyridin-1(2H)-yl]-3-(trifluoromethyl)-7,8-dihydro-[1,2,4]triazolo[4,3-b]pyridazine (107 mg, 40%) as a solid.

1H NMR (399.9 MHz, DMSO-d6) δ 2.66 (2H, m), 3.00 (2H, t), 3.18 (2H, t), 3.77 (2H, m), 4.25 (2H, m), 6.23 (1H, m), 7.06 (1H, m), 7.13 (1H, m), 7.40 (1H, d), 7.48 (1H, d), 7.87 (1H, d), 11.21 (1H, s); m/z=387 [M+H]+.

The 1-[3-(trifluoromethyl)-7,8-dihydro-[1,2,4]triazolo[4,3-b]pyridazin-6-yl]piperidin-4-one used as starting material was prepared as follows:—

Preparation of 1-[3-(trifluoromethyl)-[1,2,4]triazolo[4,3-b]pyridazin-6-yl]piperidin-4-ol 4-Hydroxypiperidine (10.91 g, 107.84 mmol) was added to 6-chloro-3-(trifluoromethyl)-[1,2,4]triazolo[4,3-b]pyridazine (20 g, 89.87 mmol) and DIPEA (23.48 mL, 134.80 mmol) in DMF (200 mL). The resulting solution was stirred at 125° C. for 2 hours. The reaction mixture was evaporated to dryness, redissolved in DCM and purified by flash silica chromatography, elution gradient 0 to 5% MeOH in DCM. Pure fractions were evaporated to dryness to give a beige solid which was stirred with ether then filtered to afford 1-[3-(trifluoromethyl)-[1,2,4]triazolo[4,3-b]pyridazin-6-yl]piperidin-4-ol (22.64 g, 88%) as a solid.

1H NMR (399.9 MHz, DMSO-d6) δ 1.46 (2H, m), 1.85 (2H, m), 3.32 (2H, m), 3.78 (1H, m), 3.96 (2H, m), 4.78 (1H, d), 7.61 (1H, d), 8.22 (1H, d); m/z=288 [M+H]+.

Preparation of 1-[3-(trifluoromethyl)-7,8-dihydro-[1,2,4]triazolo[4,3-b]pyridazin-6-yl]piperidin-4-ol 1-[3-(Trifluoromethyl)-[1,2,4]triazolo[4,3-b]pyridazin-6-yl]piperidin-4-ol (5 g, 17.41 mmol) and 5% palladium on carbon (50% wet, 0.963 g, 0.23 mmol) in MeOH (50 mL) were stirred under an atmosphere of hydrogen at 5 bar and 50° C. for 16 hours. The reaction was incomplete and further 5% palladium on carbon (50% wet, 0.963 g, 0.23 mmol) was added and the mixture was stirred at 50° C. for a further 16 hours. The catalyst was removed by filtration and washed with MeOH/DCM mixtures. The solvents were evaporated to give 1-[3-(trifluoromethyl)-7,8-dihydro-[1,2,4]triazolo[4,3-b]pyridazin-6-yl]piperidin-4-ol (4.93 g, 98%) as a solid.

1H NMR (399.9 MHz, DMSO-d6) δ 1.41 (2H, m), 1.79 (2H, m), 2.89 (2H, t), 3.13 (2H, t), 3.21 (2H, m), 3.75 (1H, m), 3.84 (2H, m), 4.77 (1H, s); m/z=290 [M+H]+.

Preparation of 1-[3-(trifluoromethyl)-7,8-dihydro-[1,2,4]triazolo[4,3-b]pyridazin-6-yl]piperidin-4-one 1,1,1-Triacetoxy-1,1-dihydro-1,2-benziodoxol-3(1H)-one (3.52 g, 8.30 mmol) was added to 1-[3-(trifluoromethyl)-7,8-dihydro-[1,2,4]triazolo[4,3-b]pyridazin-6-yl]piperidin-4-ol (2.0 g, 6.91 mmol) in DCM (30 mL). The resulting suspension was stirred at ambient temperature for 90 minutes. The reaction mixture was diluted with DCM (300 mL) and washed with 2M NaOH (2×200 mL). The organic layer was dried over MgSO4, filtered and evaporated to afford crude product. The crude product was purified by flash silica chromatography, elution gradient 5 to 10% MeOH in DCM. Pure fractions were evaporated to dryness to give 1-[3-(trifluoromethyl)-7,8-dihydro-[1,2,4]triazolo[4,3-b]pyridazin-6-yl]piperidin-4-one (0.640 g, 32%) as a solid.

1H NMR (399.9 MHz, DMSO-d6) δ 2.46 (4H, m), 2.95 (2H, t), 3.14 (2H, t), 3.80 (4H, m); m/z=288 [M+H]+.

Example 3

Preparation of 6-[4-(1H-indol-3-yl)piperidin-1-yl]-3-(trifluoromethyl)-7,8-dihydro[1,2,4]triazolo[4,3-b]pyridazine

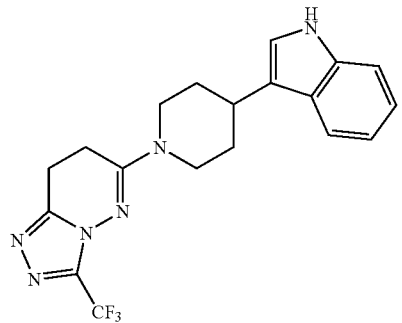

10% Palladium on carbon (23.96 mg, 0.02 mmol) was added to 6-[4-(1H-indol-3-yl)-5,6-dihydropyridin-1(2H)-yl]-3-(trifluoromethyl)-7,8-dihydro-[1,2,4]triazolo[4,3-b]pyridazine (obtained as described in Example 2) (87 mg, 0.23 mmol) and ammonium formate (71.0 mg, 1.13 mmol) in ethanol (20 mL). The resulting mixture was stirred at 78° C. for 2 hours. The reaction mixture was cooled to room temperature, evaporated to dryness, then re-dissolved in ethyl acetate (25 mL) and the solution washed sequentially with water (20 mL) and saturated brine (10 mL). The organic layer was dried over MgSO4, filtered and evaporated to afford 6-[4-(1H-indol-3-yl)piperidin-1-yl]-3-(trifluoromethyl)-7,8-dihydro[1,2,4]triazolo[4,3-b]pyridazine (60.0 mg, 69%) as a solid.

1H NMR (399.9 MHz, DMSO-d6) δ 1.69 (2H, m), 2.05 (2H, m), 2.95 (2H, t), 3.06-3.18 (5H, m), 4.29 (2H, m), 6.98 (1H, m), 7.07 (1H, m), 7.35 (1H, d), 7.60 (1H, d), 10.83 (1H, s); m/z=389 [M+H]+.

Example 4.1

Preparation of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine

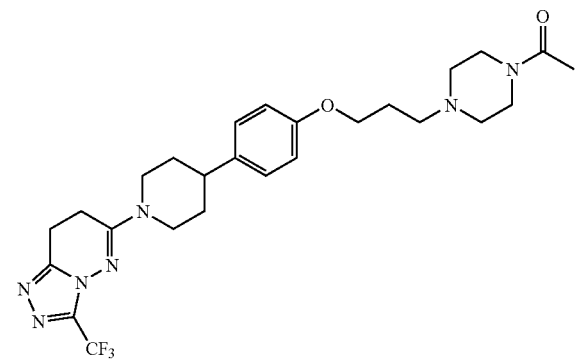

DIPEA (0.159 mL, 0.92 mmol) was added to 6-[4-[4-[3-(piperazin-1-yl)propoxy]phenyl]piperidin-1-yl]-3-(trifluoromethyl)-7,8-dihydro-[1,2,4]triazolo[4,3-b]pyridazine (150 mg, 0.31 mmol), acetic acid (0.021 mL, 0.37 mmol) and HATU (139 mg, 0.37 mmol) in DMF (2 mL). The resulting solution was stirred at ambient temperature for 16 hours then purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to give 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine (75 mg, 46.1%) as a solid.

1H NMR (399.9 MHz, CDCl3) δ 1.69 (2H, m), 1.92-1.99 (4H, m), 2.08 (3H, s), 2.41-2.47 (4H, m), 2.54 (2H, t), 2.71-2.80 (3H, m), 3.00 (2H, m), 3.21 (2H, t), 3.46 (2H, m), 3.62 (2H, m), 4.01 (2H, t), 4.31 (2H, m), 6.86 (2H, d), 7.11 (2H, d); m/z=534 [M+H]+.

The starting 6-[4-[4-[3-(piperazin-1-yl)propoxy]phenyl]piperidin-1-yl]-3-(trifluoromethyl)-7,8-dihydro-[1,2,4]triazolo[4,3-b]pyridazine was prepared as follows:

Preparation of benzyl 4-(trifluoromethylsulfonyloxy)-5,6-dihydropyridine-1(2H)-carboxylate A solution of benzyl 4-oxopiperidine-1-carboxylate (88.57 g, 379.70 mmol) in THF (300 mL) was added dropwise to lithium bis(trimethylsilyl)amide (1M in THF) (418 mL, 417.67 mmol) at −78° C., over a period of 1 hour under nitrogen. The resulting mixture was stirred at −78° C. for 90 minutes then a solution of 1,1,1-trifluoro-N-phenyl-N-(trifluoromethylsulfonyl)methanesulfonamide (142 g, 398.68 mmol) in THF (600 mL) was added dropwise over a period of 1 hour. The resulting mixture was stirred at −78° C. for 30 minutes, then allowed to warm to room temperature and stirred for 16 hours. The reaction mixture was quenched with 2M NaOH (450 mL). The layers were separated and the organic layer was washed with 2M NaOH (360 mL). The solvent was evaporated, then the residue was re-dissolved in diethyl ether (1500 mL) and the solution washed with water (500 mL). The organic layer was dried over MgSO4, filtered and evaporated to afford benzyl 4-(trifluoromethylsulfonyloxy)-5,6-dihydropyridine-1(2H)-carboxylate (124 g, 81%) as an oil.

1H NMR (399.9 MHz, DMSO-d6) δ 2.43 (2H, m), 3.62 (2H, m), 4.06 (2H, m), 5.10 (2H, s), 6.02 (1H, m), 7.34 (5H, m).

Preparation of benzyl 4-(4-hydroxyphenyl)-5,6-dihydropyridine-1(2H)-carboxylate

Sodium carbonate (96 g, 909.79 mmol) was added to benzyl 4-(trifluoromethylsulfonyloxy)-5,6-dihydropyridine-1(2H)-carboxylate (123.1 g, 303.26 mmol) and 4-hydroxyphenylboronic acid (46.0 g, 333.59 mmol) in a mixture of dioxan (1000 mL) and water (250 mL). The resulting mixture was bubbled with nitrogen for 10 minutes then 1,1'-bis(diphenylphosphino)ferrocenedichloropalladium(II) (5.49 g, 7.58 mmol) was added and the reaction mixture was heated at 80° C. for 1 hour, then cooled to room temperature. The reaction mixture was diluted with DCM (2 L) and washed with water (2 L). The aqueous washing was re-extracted with DCM (1 L), then the combined organics were washed with saturated brine (500 mL), dried over MgSO4, filtered and evaporated to afford crude product. The crude product was purified by flash silica chromatography, elution gradient 10 to 30% EtOAc in isohexane. Fractions containing the desired product were evaporated to dryness then triturated with isohexane, filtered and is dried to afford benzyl 4-(4-hydroxyphenyl)-5,6-dihydropyridine-1(2H)-carboxylate (62.3 g, 66.4%) as a solid.

1H NMR (399.9 MHz, DMSO-d6) δ 2.44 (2H, m), 3.61 (2H, m), 4.05 (2H, m), 5.12 (2H, s), 5.99 (1H, m), 6.73 (2H, d), 7.26 (2H, d), 7.32-7.40 (5H, m), 9.45 (1H, s); m/z=310 [M+H]+.

Preparation of tert-butyl 4-[3-[4-(piperidin-4-yl)phenoxy]propyl]piperazine-1-carboxylate DIAD (5.20 mL, 26.39 mmol) was added dropwise to benzyl 4-(4-hydroxyphenyl)-5,6-dihydropyridine-1(2H)-carboxylate (6.80 g, 21.99 mmol), tert-butyl 4-(3-hydroxypropyl)piperazine-1-carboxylate (5.91 g, 24.19 mmol) and triphenylphosphine (6.92 g, 26.39 mmol) in THF (100 mL) under nitrogen. The resulting solution was stirred at ambient temperature for 3 hours. The reaction mixture was evaporated to dryness then the residues were dissolved in ether (50 mL) and stirred for 10 minutes at ambient temperature. The resulting precipitate was removed by filtration. The filtrate was washed with water (50 mL) and saturated brine (50 mL), then dried over MgSO4, filtered and evaporated. The residue was dissolved in DCM (50 mL) and the solution was washed with 2M NaOH (50 mL), followed by saturated brine (50 mL), then dried over MgSO4, filtered, evaporated and purified by flash silica chromatography, elution gradient 30 to 70% ethyl acetate in isohexane. Fractions were evaporated to a gum, which was dissolved in MeOH (150 mL) and stirred with 5% palladium on carbon (50% wet, 1.907 g, 0.45 mmol) under an atmosphere of hydrogen at 5 bar and 25° C. for 16 hours. The catalyst was removed by filtration, washed with MeOH and the solvents were evaporated to give crude product. The crude product was purified by flash silica chromatography, elution gradient 0 to 10% 2M ammonia in methanol in DCM. Fractions containing the desired product were evaporated to dryness to give tert-butyl 4-[3-[4-(piperidin-4-yl)phenoxy]propyl]piperazine-1-carboxylate (4.95 g, 56%) as a solid.

1H NMR (399.9 MHz, CDCl3) δ 1.46 (9H, s), 1.60 (2H, m), 1.81 (2H, m), 1.95 (2H, m), 2.40 (4H, m), 2.50-2.59 (3H, m), 2.73 (2H, m), 3.18 (2H, m), 3.43 (4H, m), 4.00 (2H, t), 6.84 (2H, d), 7.12 (2H, d); m/z=404 [M+H]+.

Preparation of tert-butyl 4-[3-[4-[1-(3-(trifluoromethyl)-[1,2,4]triazolo[4,3-b]pyridazin-6-yl]piperidin-4-yl]phenoxy]propyl]piperazine-1-carboxylate DIPEA (2.417 mL, 13.88 mmol) was added to 6-chloro-3-(trifluoromethyl)-[1,2,4]triazolo[4,3-b]pyridazine (obtained as described in Monatsh. Chem. 1972, 103, 1591) (2.059 g, 9.25 mmol) and tert-butyl 4-[3-[4-(piperidin-4-yl)phenoxy]propyl]piperazine-1-carboxylate (3.92 g, 9.71 mmol) in DMF (30 mL). The resulting solution was stirred at 80° C. for 2 hours. The reaction mixture was cooled to room temperature and evaporated to dryness. The resulting solid was triturated with water, then collected by filtration, washed with ether and dried to afford tert-butyl 4-[3-[4-[1-(3-(trifluoromethyl)-[1,2,4]triazolo[4,3-b]pyridazin-6-yl]piperidin-4-yl]phenoxy]propyl]piperazine-1-carboxylate (4.67 g, 86%) as a solid.

1H NMR (399.9 MHz, CDCl3) δ 1.46 (9H, s), 1.54 (2H, m), 1.76 (2H, m), 1.99 (2H, m), 2.08-2.82 (7H, m), 3.11 (2H, m), 3.50-3.66 (4H, m), 4.04 (2H, t), 4.37 (2H, m), 6.84 (2H, d), 7.12 (3H, m), 7.93 (1H, d); m/z=590 [M+H]+.

Preparation of tert-butyl 4-[3-[4-(1-[3-(trifluoromethyl)-7,8-dihydro-[1,2,4]triazolo[4,3-b]pyridazin-6-yl)piperidin-4-yl]phenoxy]propyl]piperazine-1-carboxylate 10% Palladium on carbon (0.859 g, 0.81 mmol) was added to tert-butyl 4-[3-[4-[1-(3-(trifluoromethyl)-[1,2,4]triazolo[4,3-b]pyridazin-6-yl]piperidin-4-yl]phenoxy]propyl]piperazine-1-carboxylate (2.38 g, 4.04 mmol) and ammonium formate (2.55 g, 40.36 mmol) in ethanol (100 mL). The resulting mixture was stirred at 78° C., with further portions of ammonium formate being added every 5 hours until the reaction was complete. The reaction mixture was cooled to room temperature and the catalyst was removed by filtration. The filtrate was evaporated to dryness, the residue was re-dissolved in DCM (100 mL) and the solution was washed with water (50 mL) and brine (50 mL). The solvents were evaporated to give tert-butyl 4-[3-[4-(1-[3-(trifluoromethyl)-7,8-dihydro-[1,2,4]triazolo[4,3-b]pyridazin-6-yl)piperidin-4-yl]phenoxy]propyl]piperazine-1-carboxylate (2.090 g, 88%) as a solid.

1H NMR (399.9 MHz, CDCl3) δ 1.46 (9H, s), 1.68 (2H, m), 1.92-2.00 (4H, m), 2.41 (4H, m), 2.53 (2H, m), 2.71-2.80 (3H, m), 3.00 (2H, m), 3.21 (2H, t), 3.44 (4H, m), 4.01 (2H, t), 4.30 (2H, m), 6.85 (2H, d), 7.11 (2H, d); m/z=592 [M+H]+.

Preparation of 6-[4-[4-[3-(piperazin-1-yl)propoxy]phenyl]piperidin-1-yl]-3-(trifluoromethyl)-7,8-dihydro-[1,2,4]triazolo[4,3-b]pyridazine TFA (10 mL) was added to tert-butyl 4-[3-[4-(1-[3-(trifluoromethyl)-7,8-dihydro-[1,2,4]triazolo[4,3-b]pyridazin-6-yl)piperidin-4-yl]phenoxy]propyl]piperazine-1-carboxylate (2.09 g, 3.53 mmol) in DCM (10 mL). The resulting solution was stirred at ambient temperature for 1 hour then added to an SCX column. The desired product was eluted from the column using 2M ammonia in methanol and the solvents were evaporated to dryness to afford 6-[4-[4-[3-(piperazin-1-yl)propoxy]phenyl]piperidin-1-yl]-3-(trifluoromethyl)-7,8-dihydro-[1,2,4]triazolo[4,3-b]pyridazine (1.700 g, 98%) as a solid.

1H NMR (399.9 MHz, CDCl3) δ 1.69 (2H, m), 1.92-1.99 (4H, m), 2.41-2.52 (6H, m), 2.71-2.80 (3H, m), 2.90 (4H, m), 3.00 (2H, m), 3.21 (2H, t), 4.00 (2H, t), 4.31 (2H, m), 6.86 (2H, d), 7.11 (2H, d); m/z=492 [M+H]+.

Example 4.2

Larger scale preparation of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine 10% Palladium on carbon (0.276 g, 0.26 mmol) was added to 6-[4-[4-[3-(4-acetylpiperazin-1-yl)propoxy]phenyl]piperidin-1-yl]-3-(trifluoromethyl)[1,2,4]triazolo[4,3-b]pyridazine (13.80 g, 25.96 mmol) and ammonium formate (16.37 g, 259.61 mmol) in ethanol (300 mL) at 20° C. The resulting slurry was stirred at 76° C. for 32 hours, regularly adding more ammonium formate and catalyst to force the reaction to completion. The cooled reaction mixture was filtered through diatomaceous earth and the filtrate was concentrated under vacuum to give a colourless gum which was dissolved in DCM (1 L) and the solution washed with water (1 L). The organic layer was washed with brine, dried (Na$_2$SO$_4$), filtered and evaporated to dryness. The crude product was purified by flash silica chromatography, elution gradient 0 to 8% MeOH in DCM. Pure fractions were evaporated to dryness and the resulting oil was triturated with ether to give 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine (9.90 g, 71.4%) as a white solid.

1H NMR (399.9 MHz, CDCl3) δ 1.69 (2H, m), 1.92-1.99 (4H, m), 2.08 (3H, s), 2.41-2.47 (4H, m), 2.54 (2H, t), 2.71-2.80 (3H, m), 3.00 (2H, m), 3.21 (2H, t), 3.46 (2H, m), 3.62 (2H, m), 4.01 (2H, t), 4.31 (2H, m), 6.86 (2H, d), 7.11 (2H, d); m/z=534 [M+H]+.

The 6-[4-[4-[3-(4-acetylpiperazin-1-yl)propoxy]phenyl]piperidin-1-yl]-3-(trifluoromethyl)[1,2,4]triazolo[4,3-b]pyridazine used as starting material was prepared as follows:—

Preparation of benzyl 4-[4-[3-(4-acetylpiperazin-1-yl)propoxy]phenyl]-5,6-dihydropyridine-1(2H)-carboxylate DIAD (12.98 ml, 65.94 mmol) was added dropwise over 1 hour (exotherm to 5° C. with slight delay after initial addition) to a solution of benzyl 4-(4-hydroxyphenyl)-5,6-dihydropyridine-1(2H)-carboxylate (obtained as described in Example 4.1, preparation of starting materials) (13.6 g, 43.96 mmol), 3-(4-acetylpiperazine-1-yl)propanol (obtained as described in PCT Int. Appl. WO2003064413, Example 1, preparation of starting materials) (9.01 g, 48.36 mmol) and triphenylphosphine (17.30 g, 65.94 mmol) in THF (272 ml) at 0° C. under nitrogen. The resulting dark solution was stirred at 0° C. for 2 hours then warmed to room temperature and stirred overnight. The reaction mixture was concentrated and the crude product was purified by silica gel chromatography, eluting with 0-15% MeOH in EtOAc to give benzyl 4-[4-[3-(4-acetylpiperazin-1-yl)propoxy]phenyl]-5,6-dihydropyridine-1(2H)-carboxylate (17.39 g, 36.4 mmol, 83%) as a pale orange oil that solidified on standing.

1H NMR (399.902 MHz, DMSO-d6) δ 1.88 (2H, m), 1.98 (3H, s), 2.33 (2H, t), 2.38 (2H, t), 2.42-2.50 (4H, m), 3.38-3.46 (4H, m), 3.63 (2H, s), 4.02 (2H, t), 4.07 (4H, 1), 5.15 (2H, s), 6.06 (1H, s), 6.93 (2H, d) and 7.29-7.42 (7H, m); m/z=478 [M+H]+.

Preparation of 4-[4-[3-(4-acetylpiperazin-1-yl)propoxy]phenyl]piperidine

Benzyl 4-[4-[3-(4-acetylpiperazin-1-yl)propoxy]phenyl]-5,6-dihydropyridine-1(2H)-carboxylate (17 g, 35.59 mmol) and 5% palladium on carbon (3.37 g, 31.68 mmol) in iso-propanol (170 mL) were stirred under an atmosphere of hydrogen at 5 bar and 40° C. for 2 hours. The reaction mixture was filtered through diatomaceous earth, washing through with iso-propanol. The combined organics were evaporated to dryness to give crude product, which was purified by silica gel chromatography eluting with 0-10% MeOH in DCM, then 10% 7M ammonia in methanol in DCM, to give 4-[4-[3-(4-acetylpiperazin-1-yl)propoxy]phenyl]piperidine (9.4 g, 27.2 mmol, 76%) as a white solid.

1H NMR (399.9 MHz, DMSO-d$_6$) δ 1.41-1.51 (2H, m), 1.63-1.67 (2H, m), 1.83-1.90 (2H, m), 1.99 (3H, s), 2.31 (2H, t), 2.38 (2H, t), 2.42-2.60 (5H, m), 3.01 (2H, d), 3.17 (1H, s), 3.42 (4H, q), 3.98 (2H, t), 6.83-6.86 (2H, m), 7.10-7.13 (2H, m); m/z=346 [M+H]+.

Preparation of 6-[4-[4-[3-(4-acetylpiperazin-1-yl)propoxy]phenyl]piperidin-1-yl]-3-(trifluoromethyl)[1,2,4]triazolo[4,3-b]pyridazine DIPEA (5.21 mL, 29.93 mmol) was added to 6-chloro-3-(trifluoromethyl)-[1,2,4]triazolo[4,3-b]pyridazine (obtained as described in Monatsh. Chem. 1972, 103, 1591) (6.06 g, 27.21 mmol) and 4-[4-[3-(4-acetylpiperazin-1-yl)propoxy] phenyl]piperidine (9.40 g, 27.21 mmol) in DMF (200 mL). The resulting solution was stirred at 80° C. for 1 hour. The reaction mixture was cooled to room temperature then evaporated to dryness. Water (600 mL) was then added and the mixture extracted with DCM (2×600 mL). The combined organic layers were dried (Na$_2$SO$_4$), filtered and concentrated under reduced pressure. The crude product was purified by flash silica chromatography, elution gradient 0 to 10% MeOH in DCM. Pure fractions were evaporated to dryness to afford 6-[4-[4-[3-(4-acetylpiperazin-1-yl)propoxy]phenyl]piperidin-1-yl]-3-(trifluoromethyl)[1,2,4]triazolo[4,3-b]pyridazine (13.80 g, 95%) as an orange solid.

1H NMR (399.902 MHz, DMSO-d6) δ 1.58-1.73 (2H, m), 1.80-1.93 (4H, m), 1.98 (3H, s), 2.32 (2H, t), 2.37 (2H, t), 2.41-2.48 (3H, m), 2.75-2.86 (1H, m), 3.12 (2H, t), 3.37-3.47 (4H, m), 4.00 (2H, t), 4.40 (2H, d), 6.86 (2H, d), 7.17 (2H, d), 7.66 (1H, d) and 8.24 (1H, d). m/z=532 [M+H]+.

Example 4.3

Preparation of 6-[4-[4-[3-(4-acetylpiperazin-1-yl) propoxy]phenyl]piperidin-1-yl]-3-(trifluoromethyl)-7,8-dihydro[1,2,4]triazolo[4,3-b]pyridazine Form A The X-ray powder diffraction spectra for 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine showed the material to be crystalline (Form A). This material had a melting point of 146.4° C. (onset).

6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A was produced on slurrying the material in methanol or acetonitrile. This was performed by measuring approximately 20 mg of the original material into a vial with a magnetic flea and adding approximately 2 ml of solvent. The vial was then sealed tightly with a cap and left to stir on a magnetic stirrer plate. After 3 days the sample was removed from the plate, the cap taken off and the slurry left to dry under ambient conditions before it was analysed by XRPD and DSC.

6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A is characterised by providing at least one of the following 2θ values measured using CuKa radiation: 4.9 and 18.4° and by providing an X-ray powder diffraction pattern substantially as shown in Figure A. The ten most prominent peaks are shown in Table A:

TABLE A

Ten most Prominent X-Ray Powder Diffraction peaks for 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A

| Angle 2-Theta (2θ) | Intensity % | Relative Intensity |
|---|---|---|
| 4.9 | 100.0 | vs |
| 18.4 | 86.6 | vs |
| 13.5 | 76.8 | vs |
| 24.6 | 56.8 | vs |
| 6.1 | 48.8 | vs |
| 20.0 | 42.1 | vs |
| 7.5 | 39.8 | vs |

TABLE A-continued

Ten most Prominent X-Ray Powder Diffraction peaks for 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A

| Angle 2-Theta (2θ) | Intensity % | Relative Intensity |
|---|---|---|
| 12.2 | 23.9 | s |
| 16.6 | 20.0 | s |
| 19.8 | 19.4 | s | vs = very strong
s = strong

Differential Scanning Calorimetry (DSC) analysis of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A showed an initial event with an onset at 86.7° C. and a peak at 94.7° C. followed by a subsequent melt with an onset of 146.4° C. and a peak at 148.2° C. (Figure E). The first of these events is due to loss of unbound solvent. DSC analysis thus showed that 6-[4-[4-[3-(4-acetylpiperazin-1-yl) propoxy]phenyl]piperidin-1-yl]-3-(trifluoromethyl)-7,8-dihydro[1,2,4]triazolo[4,3-b]pyridazine Form A is a high melting solid with an onset of melting at about 146.4° C. and a peak at about 148.2° C.

Example 4.4

Preparation of 6-[4-[4-[3-(4-acetylpiperazin-1-yl) propoxy]phenyl]piperidin-1-yl]-3-(trifluoromethyl)-7,8-dihydro[1,2,4]triazolo[4,3-b]pyridazine Form A ethylacetate solvate 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate was produced by slurrying 6-[4-[4-[3-(4-acetylpiperazin-1-yl)propoxy] phenyl]piperidin-1-yl]-3-(trifluoromethyl)-7,8-dihydro[1,2,4]triazolo[4,3-b]pyridazine Form A in ethylacetate. Approximately 20 mg of the original material was placed in a vial with a magnetic flea, and approximately 2 ml of ethylacetate added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate) was determined to be crystalline by XRPD and seen to be different to previously seen forms.

6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate is characterised by providing at least one of the following 2θ values measured using CuKa radiation: 4.1 and 20.5° and by providing an X-ray powder diffraction pattern substantially as shown in Figure B. The ten most prominent peaks are shown in Table B:

TABLE B

Ten most Prominent X-Ray Powder Diffraction peaks for 6-[4-[4-[3-(4-acetylpiperazin-1-yl)propoxy]penyl]piperidin-1-yl]-3-(trifluoromethyl)-7,8-dihydro[1,2,4]triazolo[4,3-b]pyridazine Form A ethylacetate solvate

| Angle 2-Theta (2θ) | Intensity % | Relative Intensity |
|---|---|---|
| 4.1 | 100.0 | vs |
| 20.5 | 24.2 | s |
| 17.8 | 23.3 | s |
| 18.7 | 23.3 | s |
| 18.2 | 19.2 | s |
| 19.0 | 17.4 | s |
| 8.2 | 17.1 | s |
| 24.6 | 11.6 | s |
| 12.1 | 11.4 | s |
| 16.7 | 11.2 | s | vs = very strong
s = strong

DSC analysis of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate showed an initial endothermic event with an onset at 96.5° C. and a peak at 100.3° C. (Figure F). This was then followed by an exothermic event with onset at 102.7° C. and a peak at 104.0° C. followed by a subsequent melt with an onset of 146.0° C. and a peak of 148.2° C. DSC analysis thus showed that 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate is a high melting solid with an onset of desolvation at about 96.5° C. and a peak at about 100.3° C. and a melt with onset at about 146.0° C. and a peak at about 148.2° C.

Example 5.1

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine

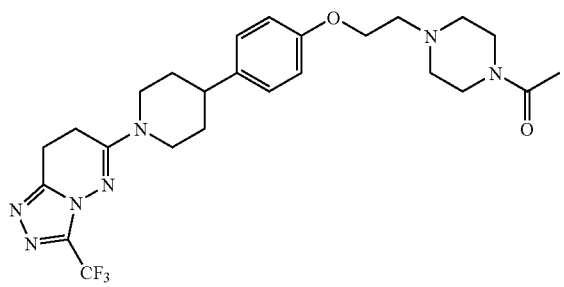

A solution of acetyl chloride (0.027 mL, 0.38 mmol) in DCM (0.5 mL) was added dropwise to 6-[4-[4-[2-(piperazin-1-yl)ethoxy]phenyl]piperidin-1-yl]-3-(trifluoromethyl)-7,8-dihydro-[1,2,4]triazolo[4,3-b]pyridazine (150 mg, 0.31 mmol) and triethylamine (0.088 mL, 0.63 mmol) in DCM (1 mL) cooled to 0° C. under nitrogen. The resulting solution was stirred at 0° C. for 5 minutes then allowed to warm to room temperature and stirred for 15 minutes. The reaction mixture was diluted with water (2 mL), passed through a phase separating cartridge and then the organic layer was evaporated to afford crude product. The crude product was purified by preparative HPLC (Waters XBridge Prep C18 OBD column, 5μ silica, 19 mm diameter, 100 mm length), using decreasingly polar mixtures of is water (containing 1% ammonia) and MeCN as eluents. Fractions containing the desired compound were evaporated to dryness to give 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (80 mg, 49%) as a gum.

1H NMR (399.9 MHz, CDCl3) δ 1.69 (2H, m), 1.95 (2H, m), 2.08 (3H, s), 2.56 (4H, m), 2.71-2.84 (5H, m), 3.00 (2H, m), 3.22 (2H, t), 3.48 (2H, m), 3.63 (2H, m), 4.10 (2H, t), 4.31 (2H, m), 6.86 (2H, d), 7.12 (2H, d); m/z=520 [M+H]+.

The 6-[4-[4-[2-(piperazin-1-yl)ethoxy]phenyl]piperidin-1-yl]-3-(trifluoromethyl)-7,8-dihydro-[1,2,4]triazolo[4,3-b]pyridazine used as starting material was prepared as follows:—

Preparation of tert-butyl 4-[2-[4-(1-(benzyloxycarbonyl)-1,2,3,6-tetrahydropyridin-4-yl)phenoxy]ethyl]piperazine-1-carboxylate DIAD (12.60 mL, 64.00 mmol) was added dropwise to benzyl 4-(4-hydroxyphenyl)-5,6-dihydropyridine-1(2H)-carboxylate (obtained as described in Example 4.1, preparation of starting materials) (16.5 g, 53.34 mmol), tert-butyl 4-(2-hydroxyethyl)piperazine-1-carboxylate (CAS 77279-24-4) (14.74 g, 64.00 mmol) and triphenylphosphine (16.79 g, 64.00 mmol) in THF (150 mL) under nitrogen. The resulting solution was stirred at ambient temperature for 16 hours. The reaction mixture was evaporated to dryness then the residue was stirred in ether (200 mL) for 10 minutes at room temperature. The resulting precipitate was removed by filtration and discarded. The ether filtrate was washed with water (100 mL) followed by saturated brine (100 mL), then dried over MgSO4, filtered and evaporated to give crude product. The crude product was purified by flash silica chromatography, elution gradient 20 to 60% EtOAc in isohexane. Fractions containing the desired product were evaporated to dryness to afford tert-butyl 4-[2-[4-(1-(benzyloxycarbonyl)-1,2,3,6-tetrahydropyridin-4-yl)phenoxy]ethyl]piperazine-1-carboxylate (34.6 g, 82%) as a gum which was contaminated with 34% by weight triphenylphosphine oxide.

1H NMR (399.9 MHz, DMSO-d6) δ 1.40 (9H, s), 2.42-2.47 (6H, m), 2.71 (2H, m), 3.32 (4H, m), 3.62 (2H, m), 4.03-4.10 (4H, m), 5.12 (2H, s), 6.06 (1H, m), 6.92 (2H, d), 7.31-7.40 (7H, m); m/z=522 [M+H]+.

Preparation of tert-butyl 4-[2-[4-(piperidin-4-yl)phenoxy]ethyl]piperazine-1-carboxylate tert-Butyl 4-[2-[4-(1-(benzyloxycarbonyl)-1,2,3,6-tetrahydropyridin-4-yl)phenoxy]ethyl]piperazine-1-carboxylate (66% pure by weight) (34.62 g, 43.80 mmol) and 5% palladium on carbon (50% wet) (4.47 g, 1.05 mmol) in MeOH (250 mL) were stirred under an atmosphere of hydrogen at 5 bar and 60° C. for 4 hours. The catalyst was removed by filtration and the solvents evaporated to give crude product. The crude product was purified by flash silica chromatography, eluting with 60% EtOAc in isohexane then 15% 2M ammonia/MeOH in DCM. Pure fractions were evaporated to dryness to afford tert-butyl 4-[2-[4-(piperidin-4-yl)phenoxy]ethyl]piperazine-1-carboxylate (15.42 g, 90%) as a solid.

1H NMR (399.9 MHz, CDCl3) δ 1.46 (9H, s), 1.62 (2H, m), 1.81 (2H, m), 2.50-2.59 (5H, m), 2.73 (2H, m), 2.80 (2H, t), 3.18 (2H, m), 3.44 (4H, m), 4.09 (2H, t), 6.85 (2H, d), 7.13 (2H, d); m/z=390 [M+H]+.

Preparation of tert-butyl 4-[2-[4-[1-(3-(trifluoromethyl)-[1,2,4]triazolo[4,3-b]pyridazin-6-yl]piperidin-4-yl]phenoxy]ethyl]piperazine-1-carboxylate DIPEA (2.348 mL, 13.48 mmol) was added to 6-chloro-3-(trifluoromethyl)-[1,2,4]triazolo[4,3-b]pyridazine (obtained as described in Monatsh. Chem. 1972, 103, 1591) (2 g, 8.99 mmol) and tert-butyl 4-[2-[4-(piperidin-4-yl)phenoxy]ethyl] piperazine-1-carboxylate (3.68 g, 9.44 mmol) in DMF (30 mL). The resulting solution was stirred at 80° C. for 2 hours. The reaction mixture was cooled to room temperature and the solvents evaporated to dryness. The resulting solid was triturated with water then collected by is filtration, washed with ether and dried to afford tert-butyl 4-[2-[4-[1-(3-(trifluoromethyl)-[1,2,4]triazolo[4,3-b]pyridazin-6-yl]piperidin-4-yl] phenoxy]ethyl]piperazine-1-carboxylate (5.02 g, 97%) as a solid.

1H NMR (399.9 MHz, CDCl3) δ 1.46 (9H, s), 1.76 (2H, m), 2.00 (2H, m), 2.54 (4H, m), 2.75-2.86 (3H, m), 3.11 (2H, m), 3.46 (4H, m), 4.11 (2H, m), 4.37 (2H, m), 6.87 (2H, d), 7.13 (3H, m), 7.92 (1H, d); m/z=576 [M+H]+.

Preparation of tert-butyl 4-[2-[4-[1-[3-(trifluoromethyl)-7,8-dihydro-[1,2,4]triazolo[4,3-b]pyridazin-6-yl)piperidin-4-yl]phenoxy]ethyl]piperazine-1-carboxylate 10% Palladium on carbon (0.924 g, 0.87 mmol) was added to tert-butyl 4-[2-[4-[1-(3-(trifluoromethyl)-[1,2,4]triazolo [4,3-b]pyridazin-6-yl]piperidin-4-yl]phenoxy]ethyl]piperazine-1-carboxylate (2.5 g, 4.34 mmol) and ammonium formate (2.74 g, 43.43 mmol) in ethanol (100 mL). The resulting mixture was stirred at 78° C., with further portions of ammonium formate being added every 5 hours until the reaction was complete. The reaction mixture was cooled to room temperature and the catalyst was removed by filtration. The filtrate was evaporated to dryness, redissolved in DCM (100 mL) and the solution was washed with water (100 mL) followed by brine (50 mL), then the solvents were evaporated to afford tert-butyl 4-[2-[4-[1-[3-(trifluoromethyl)-7,8-dihydro-[1,2,4]triazolo[4,3-b]pyridazin-6-yl)piperidin-4-yl]phenoxy] ethyl]piperazine-1-carboxylate (2.020 g, 81%) as a solid.

1H NMR (399.9 MHz, CDCl3) δ 1.46 (9H, s), 1.69 (2H, m), 1.95 (2H, m), 2.52 (4H, m), 2.71-2.82 (5H, m), 3.00 (2H, m), 3.22 (2H, t), 3.45 (4H, m), 4.09 (2H, m), 4.31 (2H, m), 6.86 (2H, d), 7.12 (2H, d); m/z=578 [M+H]+.

Preparation of 6-[4-[4-[2-(piperazin-1-yl)ethoxy]phenyl]piperidin-1-yl]-3-(trifluoromethyl)-7,8-dihydro-[1,2,4]triazolo[4,3-b]pyridazine TFA (10 mL) was added to tert-butyl 4-[2-[4-[1-[3-(trifluoromethyl)-7,8-dihydro-[1,2,4]triazolo[4,3-b]pyridazin-6-yl)piperidin-4-yl]phenoxy]ethyl]piperazine-1-carboxylate (2.02 g, 3.50 mmol) in DCM (10 mL). The resulting solution was stirred at ambient temperature for 1 hour then added to an SCX column. The desired product was eluted from the column using 2M ammonia/MeOH and the solvents were evaporated to afford 6-[4-[4-[2-(piperazin-1-yl)ethoxy]phenyl]piperidin-1-yl]-3-(trifluoromethyl)-7,8-dihydro-[1,2,4] triazolo[4,3-b]pyridazine (1.660 g, 99%) as a solid.

1H NMR (399.9 MHz, CDCl3) δ 1.68 (2H, m), 1.95 (2H, m), 2.55 (4H, m), 2.70-2.80 (5H, m), 2.91 (4H, m), 3.00 (2H, m), 3.22 (2H, t), 4.09 (2H, m), 4.30 (2H, m), 6.87 (2H, d), 7.11 (2H, d); m/z=478 [M+H]+.

Example 5.2

Larger scale preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Ammonium formate (99 g, 1568.94 mmol) was added to 6-[4-[4-[2-(4-acetylpiperazin-1-yl)ethoxy]phenyl]piperidin-1-yl]-3-(trifluoromethyl)[1,2,4]triazolo[4,3-b]pyridazine (81.2 g, 156.89 mmol) and 10% palladium on carbon (8.35 g, 7.84 mmol) in EtOH (810 mL) under nitrogen. The resulting mixture was stirred at 70° C. for 6 hours, then ammonium formate (50 g) was added. The mixture was stirred at 70° C. for 2 hours then further portions of 10% palladium on carbon (8.35 g, 7.84 mmol) and ammonium formate (50 g) were added and stirring continued at 70° C. for a further 10 hours. Ammonium formate (50 g) was added and the reaction mixture was stirred at 70° C. for 24 hours then cooled to room temperature. The catalyst was removed by filtration and the reaction charged with further 10% palladium on carbon (8.35 g, 7.84 mmol) and stirred at 70° C. for 16 hours. Further ammonium formate (50 g) was added and the stirring continued for 5 hours. The reaction mixture was cooled to room temperature and a further portion of 10% palladium on carbon (8.35 g, 7.84 mmol) was added. The mixture was heated to 70° C. for a 30 hours, cooled to room temperature and the catalyst removed by filtration and washed with EtOH. The solvent was evaporated and the residue dissolved in DCM (500 mL) and the solution washed with water (500 mL). The aqueous layer was re-extracted with DCM (500 mL), then EtOAc (500 mL×2). The combined extracts were dried over MgSO4, filtered and evaporated to give crude product. The crude product was purified by flash silica chromatography, elution gradient 0 to 5% MeOH in DCM. Pure fractions were evaporated to dryness to afford a gum, which was slurried with ether (300 mL) and re-evaporated. Methyl tert-butyl ether (250 mL) was added and the mixture was stirred vigorously for 3 days. The solid was collected by filtration and dried to afford 6-(4-{4-[2-(4-acetylpiperazin-1-yl)ethoxy] phenyl}piperidin-1-yl)-3-(trifluoromethyl)-7,8-dihydro[1,2,4]triazolo[4,3-b]pyridazine (60.8 g, 75%) as a solid.

1H NMR (399.9 MHz, CDCl3) δ 1.62 (2H, m), 1.88 (2H, m), 2.02 (3H, s), 2.49 (4H, m), 2.65-2.78 (5H, m), 2.94 (2H, m), 3.15 (2H, t), 3.42 (2H, m), 3.57 (2H, m), 4.03 (2H, t), 4.24 (2H, m), 6.80 (2H, d), 7.06 (2H, d); m/z=520 [M+H]+.

The 6-[4-[4-[2-(4-acetylpiperazin-1-yl)ethoxy]phenyl]piperidin-1-yl]-3-(trifluoromethyl)[1,2,4]triazolo[4,3-b]pyridazine used as starting material was prepared as follows:—

Preparation of 4-(piperidin-4-yl)phenol

Benzyl 4-(4-hydroxyphenyl)-5,6-dihydropyridine-1(2H)-carboxylate (obtained as described in Example 4.1, preparation of starting materials) (37.7 g, 121.86 mmol) and 5% palladium on carbon (7.6 g, 3.57 mmol) in methanol (380 mL) were stirred under an atmosphere of hydrogen at 5 bar and 25° C. for 2 hours. The catalyst was removed by filtration, washed with MeOH and the solvents evaporated. The crude material was triturated with diethyl ether, then the desired product collected by filtration and dried under vacuum to afford 4-(piperidin-4-yl)phenol (20.36 g, 94%) as a solid.

1H NMR (399.9 MHz, DMSO-d6) δ 1.46 (2H, m), 1.65 (2H, m), 2.45 (1H, m), 2.58 (2H, m), 3.02 (2H, m), 6.68 (2H, d), 7.00 (2H, d), 9.15 (1H, s); m/z=178 [M+H]+.

Preparation of 4-{1-[3-(trifluoromethyl)[1,2,4]triazolo[4,3-b]pyridazin-6-yl]piperidin-4-yl}phenol DIPEA (48.2 mL, 276.86 mmol) was added to 6-chloro-3-(trifluoromethyl)-[1,2,4]triazolo[4,3-b]pyridazine (obtained as described in Monatsh. Chem. 1972, 103, 1591) (24.65 g, 110.74 mmol) and 4-(piperidin-4-yl)phenol (20.61 g, 116.28 mmol) in DMF (200 mL). The resulting solution was stirred at 80° C. for 1 hour. The reaction mixture was cooled to room temperature, then evaporated to dryness and re-dissolved in DCM (1 L) and washed with water (2×1 L). The organic layer was washed with saturated brine (500 mL), then dried over MgSO4, filtered and evaporated to afford crude product. The crude product was triturated with ether to afford 4-{1-[3-(trifluoromethyl)[1,2,4]triazolo[4,3-b]pyridazin-6-yl]piperidin-4-yl}phenol (36.6 g, 91%) is as a solid.
1H NMR (399.9 MHz, DMSO-d6) δ 1.64 (2H, m), 1.87 (2H, m), 2.75 (1H, m), 3.09 (2H, m), 4.40 (2H, m), 6.69 (2H, d), 7.05 (2H, d), 7.65 (1H, d), 8.24 (1H, d), 9.15 (1H, s); m/z=364 [M+H]+.

Preparation of 2-(4-{1-[3-(trifluoromethyl)[1,2,4]triazolo[4,3-b]pyridazin-6-yl]piperidin-4-yl}phenoxy)ethanol A solution of ethylene carbonate (121 g, 1376.13 mmol) in DMF (200 mL) was added dropwise to a stirred suspension of 4-{1-[3-(trifluoromethyl)[1,2,4]triazolo[4,3-b]pyridazin-6-yl]piperidin-4-yl}phenol (100 g, 275.23 mmol) and potassium carbonate (76 g, 550.45 mmol) in DMF (200 mL) at 80° C. over a period of 15 minutes under nitrogen. The resulting mixture was stirred at 80° C. for 20 hours. The reaction mixture was cooled to room temperature, then concentrated and diluted with DCM (2 L), and washed sequentially with water (1 L) and saturated brine (500 mL). The organic layer was dried over MgSO4, filtered and evaporated to afford crude product. The crude product was purified by flash silica chromatography, elution gradient 70 to 100% EtOAc in isohexane. Fractions containing the desired product were evaporated to dryness then triturated with EtOAc (150 mL). The resulting solid was washed with further EtOAc (50 mL) and ether then dried to give 2-(4-{1-[3-(trifluoromethyl)[1,2,4]triazolo[4,3-b]pyridazin-6-yl]piperidin-4-yl}phenoxy)ethanol. The filtrate was evaporated and further purified by flash silica chromatography, elution gradient 70 to 100% EtOAc in isohexane. Fractions containing the desired product were evaporated to dryness then triturated with ether, dried and combined with the material previously collected to afford 2-(4-{1-[3-(trifluoromethyl)[1,2,4]triazolo[4,3-b]pyridazin-6-yl]piperidin-4-yl}phenoxy)ethanol (89 g, 79%) as a solid.
1H NMR (399.9 MHz, DMSO-d6) δ 1.66 (2H, m), 1.88 (2H, m), 2.80 (1H, m), 3.10 (2H, m), 3.70 (2H, m), 3.95 (2H, t), 4.41 (2H, m), 4.85 (1H, t), 6.87 (2H, d), 7.18 (2H, d), 7.67 (1H, d), 8.25 (1H, d); m/z=408 [M+H]+.

Preparation of 2-(4-{1-[3-(trifluoromethyl)[1,2,4]triazolo[4,3-b]pyridazin-6-yl]piperidin-4-yl}phenoxy)ethyl methanesulfonate A solution of methanesulfonyl chloride (20.37 mL, 262.16 mmol) in DCM (300 mL) was is added to 2-(4-{1-[3-(trifluoromethyl)[1,2,4]triazolo[4,3-b]pyridazin-6-yl]piperidin-4-yl}phenoxy)ethanol (89 g, 218.46 mmol) and triethylamine (60.9 mL, 436.93 mmol) in DCM (900 mL) at 0° C. over a period of 30 minutes under nitrogen. The resulting solution was stirred at 0° C. for 1 hour. The reaction mixture was diluted with DCM (1 L), and washed with water (2 L). The organic layer was dried over MgSO4, filtered and evaporated to afford 2-(4-{1-[3-(trifluoromethyl)[1,2,4]triazolo[4,3-b]pyridazin-6-yl]piperidin-4-yl}phenoxy)ethyl methanesulfonate (104 g, 98%) as a solid.
1H NMR (399.9 MHz, DMSO-d6) δ 1.67 (2H, m), 1.89 (2H, m), 2.83 (1H, m), 3.11 (2H, m), 3.23 (3H, s), 4.23 (2H, t), 4.41 (2H, m), 4.52 (2H, t), 6.91 (2H, d), 7.21 (2H, d), 7.66 (1H, d), 8.24 (1H, d); m/z=486 [M+H]+.

Preparation of 6-[4-[4-[2-(4-acetylpiperazin-1-yl)ethoxy]phenyl]piperidin-1-yl]-3-(trifluoromethyl)[1,2,4]triazolo[4,3-b]pyridazine DIPEA (107 mL, 613.00 mmol) was added to 2-(4-{1-[3-(trifluoromethyl)[1,2,4]triazolo[4,3-b]pyridazin-6-yl]piperidin-4-yl}phenoxy)ethyl methanesulfonate (99 g, 204.33 mmol) and N-acetylpiperazine (28.8 g, 224.77 mmol) in DMA (500 mL). The resulting solution was stirred at 110° C. for 1 hour. The reaction mixture was cooled to room temperature and the solvents were evaporated. The residue was dissolved in ethyl acetate (1 L) and the solution was washed with water (1 L). The aqueous was re-extracted with ethyl acetate (1 L) and the combined organics were washed with brine (1 L), dried over MgSO4, filtered and evaporated to give crude product. The aqueous layer was basified to pH 12 with 2M NaOH, then extracted with ethyl acetate (1 L), washed with brine (1 L), dried over MgSO4, filtered and evaporated to give further crude product. The crude product was purified by flash silica chromatography, elution gradient 0 to 3% MeOH in DCM then 5% MeOH in DCM. Pure fractions were evaporated to give 6-[4-[4-[2-(4-acetylpiperazin-1-yl)ethoxy]phenyl]piperidin-1-yl]-3-(trifluoromethyl)[1,2,4]triazolo[4,3-b]pyridazine (81 g, 77%) as a solid.
1H NMR (399.9 MHz, DMSO-d6) δ 1.59-1.73 (2H, m), 1.87 (2H, d), 1.99 (3H, s), 2.42 (2H, t), 2.71 (2H, t), 2.76-2.86 (1H, t), 3.08 (2H, t), 3.38-3.47 (4H, m), 4.08 (2H, t), 4.41 (2H, d), 6.88 (2H, d), 7.18 (2H, d), 7.62 (1H, d), 8.26 (1H, d); m/z=518 [M+H]+.

Example 5.3

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, obtained as described in Example 5.1, showed the material to be crystalline (Form A). This material had a melting point of 127.0° C. (onset). 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A material was also produced from slurries in methanol, ethylacetate or acetonitrile. These slurries were conducted by measuring approximately 20 mg of the original material in to a vial with a magnetic flea, and approximately 2 ml of methanol was added, the vial was then sealed tightly with a cap and left to stir on a magnetic stirrer plate. After 3 days, the sample was removed from the plate, the cap taken off and the slurry left to dry under ambient conditions before it was analysed by XRPD and DSC.
6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A is characterised by providing at least one of the following 2θ values measured using CuKa radiation: 4.7 and 9.5°, and by providing an X-ray powder diffraction pattern substantially as shown in Figure C. The ten most prominent peaks are shown in Table C:

TABLE C

Ten most Prominent X-Ray Powder Diffraction peaks for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A

| Angle 2-Theta (2θ) | Intensity % | Relative Intensity |
|---|---|---|
| 4.7 | 100.0 | vs |
| 9.5 | 87.3 | vs |
| 14.3 | 29.9 | vs |
| 19.0 | 21.9 | s |
| 18.8 | 15.9 | s |
| 22.5 | 15.8 | s |
| 22.7 | 11.9 | s |
| 21.7 | 11.7 | s |
| 17.4 | 10.9 | s |
| 11.9 | 10.8 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A shows a single thermal event which is a melt with an onset of 127.0° C. and a peak at 128.7° C. (Figure G). Thus DSC analysis shows 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A is a high melting solid with an onset of melting at about 127.0° C. and a peak at about 128.7° C.

Example 5.4

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate was produced by slurrying 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A, obtained as described in Example 5.1, in aqueous methanol or solutions of pure water. Approximately 20 mg of the original material was placed in a vial with a magnetic flea and approximately 2 ml of methanol added. The vial was then sealed tightly with a cap and left to stir on a magnetic stirrer plate. After 3 days, the sample was removed from the plate, the cap taken off and the slurry left to dry under ambient conditions before it was analysed by XRPD and DSC.

6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate is characterised by providing at least one of the following 2θ values measured using CuKa radiation: 17.8 and 8.9 and by providing an X-ray powder diffraction pattern substantially as shown in Figure D. The ten most prominent peaks are shown in Table D:

TABLE D

Ten most Prominent X-Ray Powder Diffraction peaks for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate

| Angle 2-Theta (2θ) | Intensity % | Relative Intensity |
|---|---|---|
| 17.8 | 100.0 | vs |
| 8.9 | 86.3 | vs |
| 19.0 | 44.1 | vs |
| 22.3 | 43.7 | vs |
| 23.9 | 29.8 | vs |
| 19.7 | 23.6 | s |
| 21.6 | 20.1 | s |
| 4.8 | 19.4 | s |
| 15.5 | 17.3 | s |
| 22.0 | 17.1 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate shows an initial event with an onset at 56.23° C. with a peak at 83.52° C. followed by a subsequent melt with an onset of 126.64° C. and a peak at 128.66° C. (Figure H). DSC analysis thus shows that 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate is a high melting solid which dehydrates at about 83.52° C.

Example 5.5

Alternative route for the preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A Methanol (375.0 mL) was added to 6-[4-[4-[2-(4-acetylpiperazin-1-yl)ethoxy]phenyl]piperidin-1-yl]-3-(trifluoromethyl)[1,2,4]triazolo[4,3-b]pyridazine (25.0 g, 48 m mol) in a 2.0 L autoclave reactor and to this was added 10% Pd/C (12.5 g, 50% w/w) paste at 22-25° C. under nitrogen gas atmosphere. The reaction was performed under hydrogen pressure (5.0 bar) at 50° C. temperature for 10.0 h. The reaction mass was cooled to room temperature and the catalyst removed by filtration. Filtered cake was washed with methanol. The solvent was evaporated and the residue was azeotropically distilled by is ethylacetate (2×125.0 mL) at 40° C. under reduced pressure to 3.0 rel vol (75.0 mL). Drop wise addition of tert-butylmethylether (MTBE, 375.0 mL) to the reaction mass resulted in solid material, which was collected by filtration and washed with MTBE (50.0 mL). The material was dried under reduced pressure with nitrogen gas bleed at 50° C. to afford the desired product 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (22.3 g, 88%) as a white color free flowing solid. The isolated material was confirmed by XRPD as Form A.

1H NMR (400.13 MHz, CDCl3): δ 1.62 (2H, m), 1.88 (2H, m), 2.02 (3H, s), 2.49 (4H, m), 2.65-2.78 (5H, m), 2.94 (2H, m), 3.15 (2H, t), 3.42 (2H, m), 3.57 (2H, m), 4.03 (2H, t), 4.24 (2H, m), 6.80 (2H, d), 7.06 (2H, d); m/z=520 [M+H]+.

The 6-[4-[4-[2-(4-acetylpiperazin-1-yl)ethoxy]phenyl]piperidin-1-yl]-3-(trifluoromethyl)[1,2,4]triazolo[4,3-b]pyridazine used as starting material was prepared as follows:—

Preparation of 4-{1-[3-(trifluoromethyl)[1,2,4]triazolo[4,3-b]pyridazin-6-yl]piperidin-4-yl}phenol Dimethylacetamide (250.0 mL) was added to 6-chloro-3-(trifluoromethyl)-[1,2,4]triazolo[4,3-b]pyridazine [CAS: 40971-95-7] (50.0 g, 225 m mol) at 22-25° C. in a suitable round bottom flask followed by 4-(piperidin-4-yl)phenol [CAS: 62614-84-0] (60.9 g, 236 m mol) at 22-25° C. The reaction mass was stirred to obtain a clear solution. Triethylamine (79.1 mL, 561 m mol) was slowly added to the reaction mass by drop wise addition over a period of 60 min at 25-30° C. Temperature was raised to 40° C. and the reaction mass stirred for 1.0 h. After completion of reaction, water (500.0 mL) was added to the reaction mass by drop wise addition over a period of 30 min at 40-43° C. The slurry mass was stirred for 30 min at 40° C. and then filtered under reduced pressure. The wet material was slurry washed using water (500.0 mL) for 30 min at 40° C. The solid was collected by filtration and the material washed with water (125.0 mL). The material was dried under reduced pressure with nitrogen gas bleed at 50° C. to afford the desired product 4-{1-[3-(trifluoromethyl)[1,2,4]triazolo[4,3-b]pyridazin-6-yl]piperidin-4-yl}phenol (75.1 g, 89.9%) as a free flowing solid.

1H NMR (400.13 MHz, DMSO-d6): δ 1.64 (2H, m), 1.87 (2H, m), 2.75 (1H, m), 3.09 (2H, m), 4.40 (2H, m), 6.69 (2H, d), 7.05 (2H, d), 7.65 (1H, d), 8.24 (1H, d), 9.15 (1H, s); m/z=364 [M+H]+.

Preparation of 6-[4-[4-[2-(4-acetylpiperazin-1-yl)ethoxy]phenyl]piperidin-1-yl]-3-(trifluoromethyl)[1,2,4]triazolo[4,3-b]pyridazine Dichloromethane (225.0 mL) and 4-{1-[3-(trifluoromethyl)[1,2,4]triazolo[4,3-b]pyridazin-6-yl]piperidin-4-yl}phenol (50.0 g, 138 m mol) were charged to a suitable round bottom flask at 22-25° C. Triphenylphosphine (72.2 g, 275 m mol) and 1-[4-(2-hydroxy-ethyl)piperazin-1-yl]ethanone [CAS: 83502-55-0] (47.4 g, 275 m mol) were added successively to the reaction mass and stirred for 10 min at 22-25° C. Di-isopropyl azodicarboxylate (55.65 g, 275 m mol) in dichloromethane (75.0 mL) was added to the reaction mass slowly drop wise at 25-30° C. over a period of 60-90 min. The resulting reaction mass was stirred for 1.0 h at 25-30° C. to complete the reaction. n-Heptane (600.0 mL) was introduced to the reaction mass by drop wise addition over a period of 15-30 min at 22-25° C. and stirred for 30 min at the same temperature. Thus precipitated solid was filtered and washed with n-heptane (150.0 mL). The material was then suck dried for 30 min under reduced pressure. The crude material was purified by slurry washing in methanol (325.0 mL) at 22-25° C. The solid was then collected by filtration and washed with methanol (50.0 mL). The material was dried under reduced pressure with nitrogen gas bleed at 50° C. to afford the desired product 6-[4-[4-[2-(4-acetylpiperazin-1-yl)ethoxy]phenyl]piperidin-1-yl]-3-(trifluoromethyl)[1,2,4]triazolo[4,3-b]pyridazine (61.2 g, 84%) as a free flowing solid.

1H NMR (400.13 MHz, DMSO-d6): δ 1.59-1.73 (2H, m), 1.87 (2H, d), 1.99 (3H, s), 2.42 (2H, t), 2.71 (2H, t), 2.76-2.86 (1H, t), 3.08 (2H, t), 3.38-3.47 (4H, m), 4.08 (2H, t), 4.41 (2H, d), 6.88 (2H, d), 7.18 (2H, d), 7.62 (1H, d), 8.26 (1H, d); m/z=518 [M+H]+.

PXRD and DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (Form A)

The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine showed the material to be crystalline (Form A) characterised by providing at least one of the following 2θ values measured using CuKa radiation: 21.0 and 18.8°, and by providing an X-ray powder diffraction pattern substantially as shown in Figure I. The ten most prominent peaks are shown in Table E. The X-ray powder diffraction pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A shown in Figure I differs from that shown in Figure C due to a preferred crystalline orientation in the sample.

TABLE E

Ten most prominent X-ray powder diffraction peaks of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (Form A)

| Angle 2-Theta (2θ) | Intensity % | Relative Intensity |
|---|---|---|
| 21.1 | 100.0 | vs |
| 18.8 | 96.2 | vs |
| 22.4 | 97.2 | vs |
| 22.6 | 87.9 | vs |
| 21.7 | 80.1 | vs |
| 20.8 | 79.2 | vs |
| 19.2 | 56.9 | s |
| 17.3 | 53.6 | s |
| 12.8 | 37.0 | s |
| 28.1 | 36.7 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A shows a single thermal event which is a melt with an onset of 126.5° C. and a peak at 128.4° C. (Figure J). Thus DSC analysis shows 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A is a high melting solid with an onset of melting at about 126.5° C. and a peak at about 128.4° C.

Example 5.6

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate

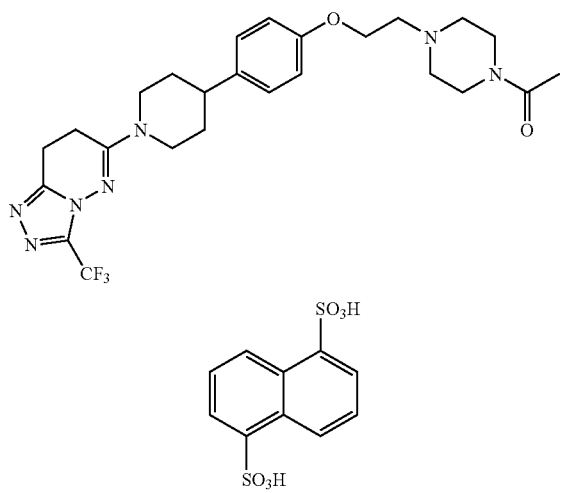

A clear solution of naphthalene-1,5-disulfonic acid (1.387 g, 3.83 m mol) in methanol (4.0 mL) was added to a clear solution of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, obtained as described in Example 5.5, (2.0 g, 3.83 m mol) in methanol (4.0 mL) at 22-25° C. and the reaction mass stirred for 60 min at 22-25° C. The resulting white material was collected by filtration and washed with methanol (5.0 mL). The material was dried under reduced pressure under nitrogen atmosphere at 50° C. to afford the desired product 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate (3.0 g, 99.0%) as free flowing solid.

1H NMR (400.13 MHz, DMSO-$d_6$): δ 1.59 (2H, m), 1.77 (2H, m), 2.03 (3H, s), 2.79 (1H, m), 2.89-3.05 (6H, m), 3.06-3.16 (3H, m), 3.41 (1H, m), 3.53-3.57 (4H, m), 4.00 (1H, m), 4.27-4.29 (4H, m), 4.4 (1H, m), 6.91 (2H, d), 7.17 (2H, d), 7.41 (2H, t), 7.93 (2H, d), 8.84 (2H, d).

PXRD and DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate showed the material to be crystalline characterised by providing at least one of the following 2θ values measured using CuKa radiation: 19.8 and 19.4°, and by providing an X-ray powder diffraction pattern substantially as shown in Figure K. The ten most prominent peaks are shown in Table F.

TABLE F

Ten most prominent X-ray powder diffraction peaks of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate

| Angle 2-Theta (2θ) | Intensity % | Relative Intensity |
|---|---|---|
| 19.8 | 100.0 | vs |
| 19.4 | 91.9 | vs |
| 18.9 | 61.0 | vs |
| 21.3 | 54.9 | vs |
| 22.4 | 53.0 | s |
| 8.7 | 43.7 | s |
| 11.9 | 40.0 | s |
| 9.4 | 39.8 | s |
| 20.3 | 32.2 | s |
| 13.8 | 31.9 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate shows two thermal events, a low endotherm at about 74.6° C. (peak) due to the moisture content present in the compound and another endotherm for melting of compound with a peak of about 219.6° C. (Figure L). Thus DSC analysis shows 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate is a high melting solid with a peak of melting at about 219.6° C.

Example 5.7

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate

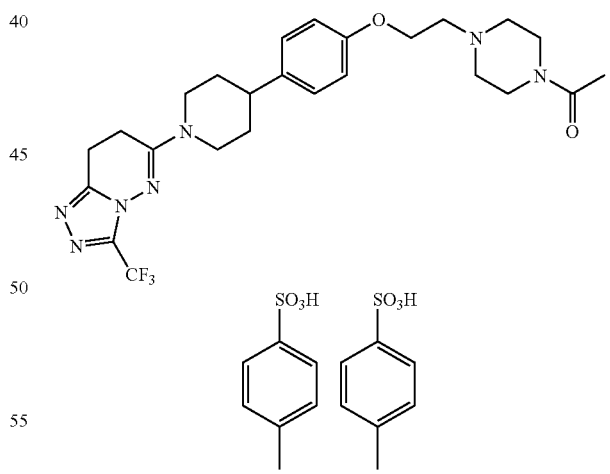

A clear solution of toluene-4-sulfonic acid (2.884 g, 15.0 m mol) in methanol (5.0 mL) was added to a clear solution of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, obtained as described in Example 5.5, (3.9 g, 7.5 m mol) in methanol (8.0 mL) at 22-25° C. Ethylacetate (20.0 mL) was added drop wise to the resulting clear solution at 22-25° C. The reaction mass was then stirred for 60 min at 22-25° C. The resulting white color material was collected by filtration and washed with methanol (105.0 mL). The material was dried under reduced pressure with nitrogen gas bleed at 50° C. to afford the desired product 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate (4.31 g, 67.0%) as free flowing white color material.

1H NMR (400.13 MHz, DMSO-$d_6$): δ 1.59 (2H, m), 1.79 (2H, m), 2.04 (3H, s), 2.29 (6H, s), 2.79 (1H, m), 2.91-3.02 (6H, m), 3.13-3.17 (3H, m), 3.41 (1H, m), 3.55-3.57 (4H, m), 4.00 (1H, m), 4.30-4.32 (4H, m), 4.4 (1H, m), 6.93 (2H, d), 7.11 (2H, d), 7.19 (2H, d), 7.48 (2H, d).

PXRD and DSC of 6-(4-[4-{2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate showed the material is in crystalline form characterised by providing at least one of the following 2θ values measured using CuKa radiation: 23.1 and 17.5°, and by providing an X-ray powder diffraction pattern substantially as shown in Figure M. The ten most prominent peaks are shown in Table G.

TABLE G

Ten most prominent X-ray powder diffraction peaks for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate

| Angle 2-Theta (2θ) | Intensity % | Relative Intensity |
|---|---|---|
| 23.1 | 100.0 | vs |
| 17.5 | 77.1 | vs |
| 22.1 | 60.3 | vs |
| 21.9 | 44.0 | vs |
| 6.5 | 36.1 | s |
| 12.8 | 26.8 | s |
| 13.6 | 25.6 | s |
| 23.5 | 25.3 | s |
| 20.1 | 22.7 | s |
| 14.9 | 22.0 | s | vs = very strong s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate shows a single endotherm with a peak of about 224.8° C. (Figure N). Thus DSC analysis shows 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate is a high melting solid with a peak of melting at about 224.8° C.

Example 5.8

Preparation of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate

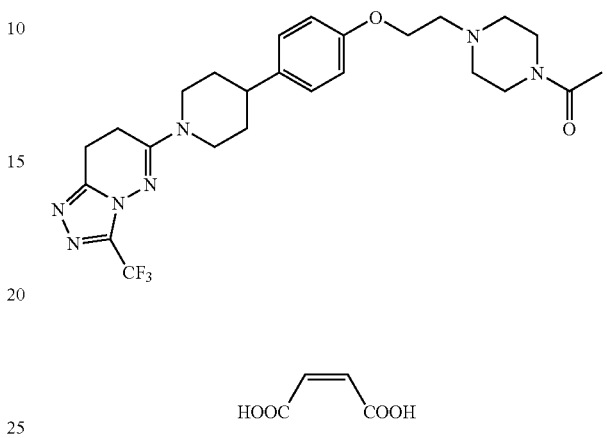

is A clear solution of maleic acid (0.445 g, 3.84 m mol) in methanol (1.0 mL) was added to a clear solution of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, obtained as described in Example 5.5, (2.0 g, 3.84 m mol) in methanol (2.0 mL) at 22-25° C. and the resulting clear solution heated to 50° C. for 30 min. The reaction mass was cooled to 22-25° C. and ethylacetate (16.0 mL) added drop wise to the reaction mass at 22-25° C. The reaction mass was then stirred for 60 min at 22-25° C. The resulting white color material was collected by filtration and washed with ethylacetate (5.0 mL). The material was dried under reduced pressure with nitrogen gas bleed at 50° C. to afford the desired product 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate (2.21 g, 90.0%) as free flowing white color material.

1H NMR (400.13 MHz, DMSO-$d_6$): δ 1.62 (2H, m), 1.77 (2H, m), 2.02 (3H, s), 2.75 (1H, m), 2.77 (2H, m), 2.80 (2H, m), 2.95 (4H, m), 3.16 (2H, t), 3.36 (6H, m), 4.22 (4H, m), 6.08 (2H, s), 6.91 (2H, d), 7.17 (2H, d).

PXRD and DSC of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate showed the material in crystalline form characterised by providing at least one of the following 2θ values measured using CuKa radiation: 20.3 and 22.0°, and by providing an X-ray powder diffraction pattern substantially as shown in Figure O. The ten most prominent peaks are shown in Table H.

TABLE H

Ten most prominent X-ray powder diffraction peaks for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate

| Angle 2-Theta (2θ) | Intensity % | Relative Intensity |
|---|---|---|
| 20.3 | 100.0 | vs |
| 22.0 | 96.6 | vs |
| 11.9 | 84.3 | vs |
| 19.4 | 84.0 | vs |
| 26.5 | 64.2 | vs |
| 19.6 | 61.5 | vs |
| 24.9 | 55.1 | s |
| 27.2 | 49.7 | s |
| 16.8 | 42.4 | s |
| 13.5 | 41.0 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate shows a single endotherm with a peak of about 179.2° C. (Figure P). Thus DSC analysis shows 6-(4-{4-[2-(4-acetylpiperazin-1-yl) ethoxy]phenyl}piperidin-1-yl)-3-(trifluoromethyl)-7,8-dihydro[1,2,4]triazolo[4,3-b]pyridazine maleate is a high melting solid with a peak of melting at about 179.2° C.

Example 5.9

Preparation of 6-(4-{4-[2-(4-acetylpiperazin-1-yl) ethoxy]phenyl}piperidin-1-yl)-3-(trifluoromethyl)-7,8-dihydro[1,2,4]triazolo[4,3-b]pyridazine fumarate

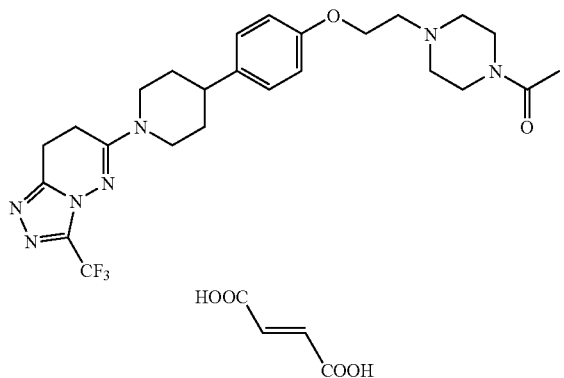

A clear solution of fumaric acid (0.223 g, 1.92 m mol) in methanol (3.0 mL) was added to a clear solution of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine, obtained as described in Example 5.5, (1.0 g, 1.92 m mol) in methanol (2.0 mL) at 22-25° C. and the resulting clear solution heated to 50° C. for 30 min. The mixture was cooled to 22-25° C. and ethylacetate (8.0 mL) charged drop wise into the reaction mass at 22-25° C. The solvent was stripped off and the reaction mass charged with fresh ethylacetate (8.0 mL). The reaction mass was then stirred for 60 min at 22-25° C. The resulting white color material was collected by filtration. The material was then dried under reduced pressure with nitrogen gas bleed at 50° C. to afford the desired product 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate (0.91 g, 74.0%) as free flowing white color material.

1H NMR (400.13 MHz, DMSO-$d_6$): δ 1.61 (2H, m), 1.81 (2H, m), 1.97 (3H, s), 2.42 (2H, m), 2.71 (3H, m), 2.90 (4H, m), 3.12 (2H, m), 3.38 (6H, m), 4.04 (2H, m), 4.27 (2H, m), 6.62 (2H, s), 6.86 (2H, d), 7.14 (2H, d).

PXRD and DSC of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate The X-ray powder diffraction spectra for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate showed the material is in crystalline form characterised by providing at least one of the following 2θ values measured using CuKa radiation: 21.1 and is 20.4°, and by providing an X-ray powder diffraction pattern substantially as shown in Figure Q. The ten most prominent peaks are shown in Table I.

TABLE I

Ten most prominent X-ray powder diffraction peaks for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate

| Angle 2-Theta (2θ) | Intensity % | Relative Intensity |
|---|---|---|
| 21.1 | 100.0 | vs |
| 20.4 | 96.5 | vs |
| 18.5 | 74.8 | vs |
| 21.9 | 72.3 | vs |
| 17.9 | 71.0 | vs |
| 23.7 | 69.9 | vs |
| 9.4 | 69.0 | s |
| 19.9 | 51.0 | s |
| 24.3 | 50.3 | s |
| 15.2 | 43.9 | s | vs = very strong
s = strong

DSC analysis of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate shows three endotherms. The first with a peak at about 65.2° C., the second with a peak at about 141.9° C., and the third one with a peak at about 147° C. (Figure R). Thus DSC analysis shows 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate is a high melting solid with an onset of melting at about 147° C.

Example 5.10

Preparation of 6-(4-{4-[2-(4-acetylpiperazin-1-yl) ethoxy]phenyl}piperidin-1-yl)-3-(trifluoromethyl)-7,8-dihydro[1,2,4]triazolo[4,3-b]pyridazine in amphorous form a)   6-(4-{4-[2-(4-acetylpiperazin-1-yl)ethoxy] phenyl}piperidin-1-yl)-3-(trifluoromethyl)-7,8-dihydro [1,2,4]triazolo[4,3-b]pyridazine:PEG400:Gelucire 44/14 10:50:40% w/w mixture.

1.00 g of Gelucire 44/14 (Lauroyl Macrogol-32 Glycerides) was weighed into a glass vial and heated to 50° C. in a temp-controlled heating block with continuous stirring (600 rpm). The Gelucire melted within 5 minutes. 1.25 g of PEG 400 (Fluka Chemika) was weighed into the molten Gelucire and stirred for 10 minutes at 50° C. 250 mg of unmilled 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (obtained as described in Example 5.5) was weighed into the molten Gelucire:PEG400 and stirred (600 rpm) for 20 minutes at 50° C. by which time the 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine had almost fully dissolved. The temperature was increased to 70° C. and the stirrer speed increased to 800 rpm. A colourless solution was achieved after 5 minutes of stirring. 500 mg of the solution was weighed into a Shinogi QualiV HPMC size 0 capsule (lot E0703189) and allowed to cool to room temperature before closing the capsule. Four 4 capsules were made using this method. The overage material remaining in the glass vial at the end of capsule filing was cooled to room temperature and analysed by XRPD.

The XRPD was compared to that XRPD pattern obtained for Gelucire. The liquid component (PEG 400) was not analysed by XRPD, due to the lack of long range order and therefore a lack of an X-ray diffraction. The comparison of XRPD's allowed the peaks associated with the formulation excipients to be subtracted from those peaks (very strong to weak) associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine. The peaks associated with the excipients did not overlap with any very strong, strong, medium or weak peaks associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine. The XRPD of the formulation did not show any peaks (strong to weak) associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine crystalline solid forms. Thus the 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine in the formulation was in an amorphous form.

b) 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine:PEG400:PEG1500 10:50:40% w/w mixture.

1.00 g of PEG 1500 (Fluka Chemika) was weighed into a glass vial and heated to 50° C. in a temp-controlled heating block with continuous stirring (600 rpm). The PEG1500 melted within 5 minutes. 1.25 g of PEG 400 (Fluka Chemika) was weighed into the molten PEG1500 and stirred for 10 minutes at 50° C. 250 mg of unmilled 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine (obtained as described in Example 5.5) was weighed into the molten PEG1500:PEG400 and stirred (800 rpm) for 20 minutes at 70° C. A colourless solution was achieved after 20 minutes of stirring. 500 mg of the solution was weighed into a Shinogi QualiV HPMC size 0 capsule (lot E0703189) and allowed to cool to room temperature before closing the capsule. Four capsules were made using this method. The overage material remaining in the glass vial at the end of capsule filing was cooled to room temperature and analysed by XRPD.

The XRPD was compared to that XRPD pattern obtained for PEG1500. The liquid component (PEG 400) was not analysed by XRPD, due to the lack of long range order and therefore a lack of an X-ray diffraction. The comparison of XRPD's allowed those peaks associated with the formulation excipients to be subtracted from those peaks (very strong to weak) associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine. The peaks associated with the excipients did not overlap with any very strong, strong, medium or weak peaks associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine. The XRPD of the formulation did not show any peaks (strong to weak) associated with 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine crystalline solid forms. Thus the 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine in the formulation was in an amorphous form.

Examples 6-9

The following compounds were prepared in 12-39% yield by an analogous method to Example 1, starting from 6-piperazin-1-yl-3-(trifluoromethyl)-7,8-dihydro[1,2,4]triazolo[4,3-b]pyridazine and the appropriate aldehyde:

| Ex. | R | 1H NMR(399.9 MHz, DMSO-d6) | m/z [M + H]+ |
|---|---|---|---|
| 6 | 3-F | δ 2.31(4H, m), 2.74(2H, t), 2.98(2H, t), 3.38(4H, m), 3.41(2H, s), 6.92-7.04(3H, m), 7.24(1H, m) | 383 |
| 7 | 3-Cl | δ 2.45(4H, m), 2.88(2H, t), 3.13(2H, t), 3.53(6H, m), 7.34(4H, m) | 399 |
| 8 | 3-CF$_3$ | δ 2.47(4H, m), 2.88(2H, t), 3.13(2H, t), 3.53(4H, m), 3.64(2H, s), 7.57-7.67(4H, m) | 433 |
| 9 | 2,3-di-F | δ 2.49(4H, m), 2.88(2H, t), 3.13(2H, t), 3.52(4H, m), 3.65(2H, s), 7.18-7.28(2H, m), 7.36(1H, m) | 401 |

Example 10

Preparation of 6-[4-[2-(difluoromethyl)-5-fluorobenzyl]piperazin-1-yl]-3-(trifluoromethyl)-7,8-dihydro[1,2,4]triazolo[4,3-b]pyridazine

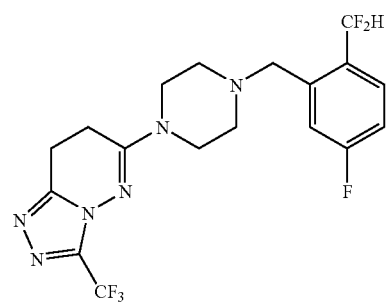

Obtained in 67% yield by an analogous method to Example 1, starting from 6-(piperazin-1-yl)-3-(trifluoromethyl)-7,8-dihydro-[1,2,4]triazolo[4,3-b]pyridazine and 2-difluoromethyl-5-fluorobenzaldehyde.

1H NMR (399.9 MHz, DMSO-d6) δ 2.46 (4H, m), 2.89 (2H, t), 3.14 (2H, t), 3.51 (4H, m), 3.67 (2H, s), 7.22-7.49 (3H, m), 7.69 (1H, m); m/z=433 [M+H]+.

The 2-difluoromethyl-5-fluorobenzaldehyde used as starting material was prepared as follows:—

Isopropylmagnesium chloride-lithium chloride complex (1M, 21.46 mL, 21.46 mmol) was added to 2-bromo-1-(difluoromethyl)-4-fluorobenzene (4.39 g, 19.51 mmol) in THF (120 mL) cooled to −20° C. under nitrogen. The resulting solution was stirred at −20° C. for 1 hour. N,N-Dimethylformamide (1.813 mL, 23.41 mmol) was added, and the mixture stirred for a further 1 hour, maintaining the temperature in the range −15 to −20° C. The mixture was allowed to warm to ambient temperature, then 2M hydrochloric acid (100 mL) was added and the mixture was extracted with EtOAc (150 mL). The organic layer was washed with saturated sodium bicarbonate (120 mL) and concentrated to yield crude product. The crude product was purified by flash silica chromatography, elution gradient 5 to 10% EtOAc in isohexane. Pure fractions were evaporated to dryness to afford 2-(difluoromethyl)-5-fluorobenzaldehyde (1.250 g, 36.8%) as a colourless liquid.

1H NMR (399.9 MHz, CDCl3) δ 7.26 (1H, t), 7.37-7.43 (1H, m), 7.63-7.67 (1H, m), 7.78-7.82 (1H, m), 10.19 (1H, d); m/z=173 [M−H]−.

Examples 11-13

The following compounds were prepared in 46-55% yield by an analogous method to Example 1, starting from 6-(piperazin-1-yl)-3-(trifluoromethyl)-7,8-dihydro-[1,2,4]triazolo[4,3-b]pyridazine and the appropriate indole-3-carboxaldehyde:

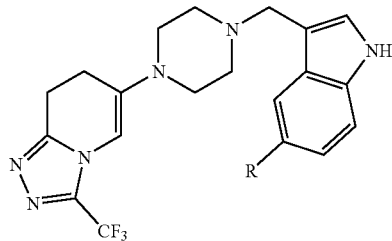

| Ex. | R | 1H NMR(399.9 MHz, DMSO-d6) | m/z [M + H]+ |
|---|---|---|---|
| 11 | H | δ 2.47(4H, m), 2.87(2H, t), 3.11(2H, t), 3.50(4H, m), 3.69(2H, s), 6.99(1H, m), 7.08(1H, m), 7.26(1H, d), 7.36(1H, d), 7.65(1H, d), 10.97(1H, s) | 404 |
| 12 | F | δ 2.46(4H, m), 2.87(2H, t), 3.11(2H, t), 3.50(4H, m), 3.66(2H, s), 6.92(1H, m), 7.37(3H, m), 11.08(1H, s) | 422 |
| 13 | CN | δ 2.47(4H, m), 2.87(2H, t), 3.11(2H, t), 3.51(4H, m), 3.73(2H, s), 7.44(1H, m), 7.49(1H, s), 7.54(1H, d), 8.19(1H, s), 11.57(1H, s) | 429 |

Example 14

Preparation of 4-(4-fluorophenyl)-1-[3-(trifluoromethyl)-7,8-dihydro[1,2,4]triazolo[4,3-b]pyridazin-6-yl]piperidin-4-ol

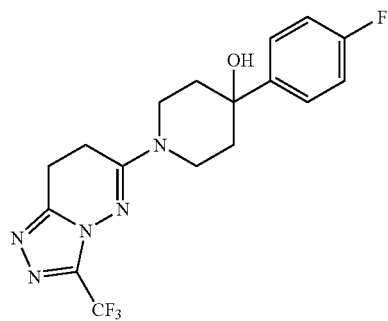

Obtained in 33% yield by an analogous method to Example 4.2, starting from 4-(4-fluorophenyl)-1-[3-(trifluoromethyl)[1,2,4]triazolo[4,3-b]pyridazin-6-yl]piperidin-4-ol.

1H NMR (399.9 MHz, DMSO-d6) δ 1.66 (2H, m), 1.97 (2H, m), 2.95 (2H, t), 3.16 (2H, t), 3.31 (2H, m), 4.09 (2H, m), 5.28 (1H, s), 7.15 (2H, m), 7.53 (2H, m); m/z=384 [M+H]+.

The 4-(4-fluorophenyl)-1-[3-(trifluoromethyl)[1,2,4]triazolo[4,3-b]pyridazin-6-yl]piperidin-4-ol used as starting material was prepared as follows:—

6-Chloro-3-(trifluoromethyl)-[1,2,4]triazolo[4,3-b]pyridazine (obtained as described in Monatsh. Chem. 1972, 103, 1591) (251 mg, 1.13 mmol), 4-(4-fluorophenyl)piperidin-4-ol (215 mg, 1.13 mmol) and DIPEA (0.20 mL, 1.13 mmol) in DMF (3 mL) were stirred and heated at 80° C. for 1 hour. The resulting solution was cooled to ambient temperature, and quenched with water (10 mL). The precipitated solid was collected by filtration, washed sequentially with water, acetonitrile and ether and dried under vacuum to give 4-(4-fluorophenyl)-1-[3-(trifluoromethyl)[1,2,4]triazolo[4,3-b]pyridazin-6-yl]piperidin-4-ol (320 mg, 74%).

1H NMR (399.9 MHz, DMSO-d6) δ 1.71-1.75 (2H, m), 1.98-2.06 (2H, m), 3.40-3.46 (2H, m), 4.19-4.22 (2H, m), 5.28 (1H, s), 7.14 (2H, t), 7.54 (2H, dd), 7.66 (1H, d), 8.24 (1H, d); m/z=382 [M+H]+.

Example 15

Preparation of 6-[4-[4-[2-(1-methyl-1H-pyrazol-5-yl)ethoxy]phenyl]piperidin-1-yl]-3-(trifluoromethyl)-7,8-dihydro[1,2,4]triazolo[4,3-b]pyridazine

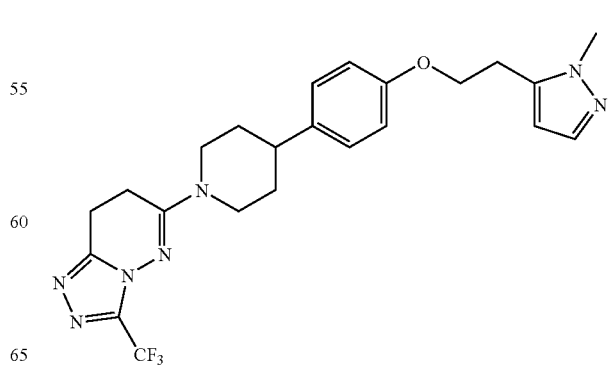

Obtained in 73% yield by an analogous method to Example 4.2, starting from 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine.

1H NMR (399.9 MHz, DMSO-d6) δ 1.61 (2H, m), 1.82 (2H, m), 2.78 (1H, m), 2.92-3.02 (4H, m), 3.09 (2H, t), 3.15 (2H, t), 3.79 (3H, s), 4.18 (2H, t), 4.29 (2H, m), 6.14 (1H, d), 6.89 (2H, d), 7.17 (2H, d), 7.30 (1H, d); m/z=474 [M+H]+.

The 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine used as starting material was prepared as follows:—

Preparation of 2-(1-methyl-1H-pyrazol-5-yl)ethanol n-Butyl lithium (1.6M in hexanes) (1226 mL, 1961.78 mmol) was added dropwise to 1-methyl-1H-pyrazole (153.4 g, 1868.37 mmol) in THF (3000 mL) cooled to −78° C. over a period of 1 hour under nitrogen. The resulting solution was stirred at −60° C. for 30 minutes, then warmed to −10° C. and stirred for a further 40 minutes. A solution of oxirane (210 mL, 4203.82 mmol) in THF (600 mL) was added slowly at −10° C. followed by further THF (1000 mL) and the resulting slurry was stirred at −10° C. for 30 minutes, then at 0° C. for 30 minutes. The mixture was then allowed to gradually warm to room temp under nitrogen and stirred for 16 hours. The reaction mixture was quenched with saturated NH4Cl solution (2000 ml), the layers separated and the aqueous phase extracted with n-butanol (3×1000 ml). The combined organics were washed with saturated brine (1500 ml), dried over MgSO4, filtered and evaporated to give an oil, which was azeotroped with toluene (1000 ml) to leave an oil with some solid. The oil was dissolved in DCM and the insoluble solid was filtered off and washed with DCM. The filtrate was purified by chromatography using a silica Novasep prep HPLC column, eluting with a gradient of 5-10% methanol in DCM. Pure fractions were evaporated to dryness to afford 2-(1-methyl-1H-pyrazol-5-yl)ethanol (195 g, 83%) as an oil.

1H NMR (400.1 MHz, DMSO-d6) δ 2.77 (2H, t), 3.63 (2H, m), 3.74 (3H, s), 4.74 (1H, t), 6.04 (1H, m), 7.26 (1H, d).

Preparation of 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine DIAD (19.73 mL, 100.18 mmol) was added dropwise to 4-[1-[3-(trifluoromethyl)[1,2,4]triazolo[4,3-b]pyridazin-6-yl]piperidin-4-yl]phenol (obtained as described in Example 5.2, preparation of starting materials) (28 g, 77.06 mmol), 2-(1-methyl-1-1H-pyrazol-5-yl)ethanol (14.53 g, 100.18 mmol) and triphenylphosphine (26.3 g, 100.18 mmol) in THF (250 mL). The resulting solution was stirred at ambient temperature for 3 days. The reaction mixture was evaporated to dryness and re-dissolved in DCM (1 L), and the solution was washed sequentially with 2M NaOH (300 mL×2) and saturated brine (250 mL). The organic layer was dried over MgSO4, filtered and evaporated to afford crude product. The crude product was purified by flash silica chromatography, eluting with 75% EtOAc in isohexane followed by a gradient of 0 to 3% MeOH in DCM. Fractions containing the desired product were evaporated to dryness then re-dissolved in DCM (500 mL) and the solution washed with 2M NaOH (300 mL×2) followed by brine (250 mL), then dried over MgSO4, filtered and evaporated. The residue was further purified by flash silica chromatography, elution gradient 80 to 100% EtOAc in isohexane. Pure fractions were evaporated to dryness to afford 6-[4-[4-[2-(1-methyl-1H-pyrazol-5-yl)ethoxy]phenyl]piperidin-1-yl]-3-(trifluoromethyl)[1,2,4]triazolo[4,3-b]pyridazine (18.21 g, 50.1%) as a solid.

1H NMR (399.9 MHz, DMSO-d6) δ 1.67 (2H, m), 1.88 (2H, m), 2.81 (1H, m), 3.07-3.14 (4H, m), 3.79 (3H, s), 4.18 (2H, t), 4.41 (2H, m), 6.14 (1H, d), 6.89 (2H, d), 7.19 (2H, d), 7.30 (1H, d), 7.66 (1H, d), 8.24 (1H, d); m/z=472 [M+H]+.

Example 16

Preparation of 6-[4-[4-[2-(1-methyl-1H-pyrazol-5-yl)ethoxy]phenyl]piperazin-1-yl]-3-(trifluoromethyl)-7,8-dihydro[1,2,4]triazolo[4,3-b]pyridazine

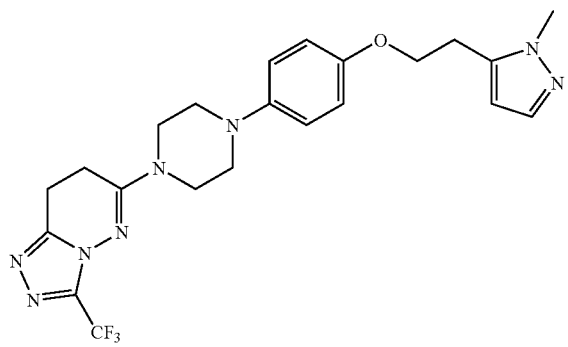

Obtained in 65% yield by an analogous method to Example 4.2, starting from 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine.

1H NMR (399.9 MHz, DMSO-d6) δ 2.95 (2H, t), 3.05-3.18 (8H, m), 3.66 (4H, m), 3.79 (3H, s), 4.14 (2H, t), 6.14 (1H, d), 6.87 (2H, d), 6.94 (2H, d), 7.31 (1H, d); m/z=475 [M+H]+.

The 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine used as starting material was prepared as follows:—

Preparation of 4-[4-[3-(trifluoromethyl)[1,2,4]triazolo[4,3-b]pyridazin-6-yl]piperazin-1-yl]phenol DIPEA (52.4 mL, 300.84 mmol) was added to 6-chloro-3-(trifluoromethyl)-[1,2,4]triazolo[4,3-b]pyridazine (obtained as described in Monatsh. Chem. 1972, 103, 1591) (44.6 g, 200.56 mmol) and 1-(4-hydroxyphenyl)piperazine (39.32 g, 220.61 mmol) in DMF (450 mL). The resulting solution was stirred at 80° C. for 2 hours. The reaction mixture was cooled to room temperature, then evaporated to dryness and partitioned between DCM (2 L) and water (1 L) containing methanol (250 mL) to aid solubility. The insoluble material was collected by filtration, washed with methanol and dried to give the desired product. The organic filtrate was separated from the aqueous, then washed with saturated brine (500 mL), dried over MgSO4 and evaporated to a brown gum. This was triturated with ether, the resulting solid was collected by filtration, washed with DCM followed by methanol, combined with the previous precipitate and dried to afford 4-{4-[3-(trifluoromethyl)[1,2,4]triazolo[4,3-b]pyridazin-6-yl]piperazin-1-yl}phenol (63.8 g, 87%) as a solid.

1H NMR (399.9 MHz, DMSO-d6) δ 3.12 (4H, m), 3.75 (4H, m), 6.69 (2H, d), 6.87 (2H, d), 7.67 (1H, d), 8.28 (1H, d), 8.87 (1H, s); m/z=365 [M+H]+.

Preparation of 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine DIAD (20.73 mL, 105.27 mmol) was added dropwise to 4-[4-[3-(trifluoromethyl)[1,2,4]triazolo[4,3-b]pyridazin-6-yl]piperazin-1-yl]phenol (32.0 g, 87.72 mmol), 2-(1-methyl-1H-pyrazol-5-yl)ethanol (obtained as described in Example 15, preparation of starting materials) (16.6 g, 131.58 mmol) and triphenylphosphine (34.5 g, 131.58 mmol) in THF (320 mL) at 0° C. under nitrogen. The resulting solution was stirred at ambient temperature for 3 days. The reaction mixture was evaporated to dryness and re-dissolved in DCM (700 mL), and the solution was washed sequentially with 2M NaOH (200 mL×2) and saturated brine (200 mL). The organic layer was dried over MgSO4, filtered and evaporated to afford crude product. The crude product was purified by flash silica chromatography, eluting with a gradient of 80 to 100% EtOAc in isohexane followed by EtOAc, then a gradient of 0 to 3% MeOH in DCM. Pure fractions were evaporated to dryness to afford 6-[4-[4-[2-(1-methyl-1H-pyrazol-5-yl)ethoxy]phenyl]piperazin-1-yl]-3-(trifluoromethyl)[1,2,4]triazolo[4,3-b]pyridazine (28.7 g, 69.3%) as a solid.

1H NMR (399.9 MHz, DMSO-d6) δ 3.07 (2H, t), 3.18 (4H, m), 3.76 (4H, m), 3.79 (3H, s), 4.15 (2H, t), 6.14 (1H, d), 6.88 (2H, d), 6.97 (2H, d), 7.30 (1H, d), 7.67 (1H, d), 8.28 (1H, d); m/z=473 [M+H]+.

Example 17

Preparation of 6-[4-(1H-pyrrolo[2,3-b]pyridin-3-yl)-3,6-dihydropyridin-1(2H)-yl]-3-(trifluoromethyl)-7,8-dihydro[1,2,4]triazolo[4,3-b]pyridazine

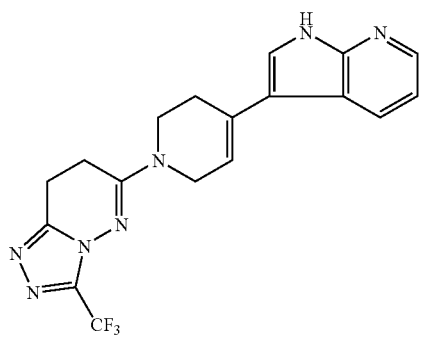

Obtained in 27% yield by an analogous method to Example 2, starting from 1-[3-(trifluoromethyl)-7,8-dihydro-[1,2,4]triazolo[4,3-b]pyridazin-6-yl]piperidin-4-one and 1H-pyrrolo[2,3-b]pyridine.

1H NMR (400 MHz, DMSO-d6) d 2.59-2.73 (2H, m), 3.00 (2H, t), 3.18 (2H, t), 3.70-3.84 (2H, m), 4.18-4.30 (2H, m), 6.28 (1H, t), 7.06-7.18 (1H, m), 7.56-7.67 (1H, m), 8.22-8.26 (1H, m), 8.29 (1H, d), 11.75 (1H, s); m/z=388 [M+H]+.

Example 18

Preparation of 6-[4-(1H-pyrrolo[2,3-b]pyridin-3-yl)piperidin-1-yl]-3-(trifluoromethyl)-7,8-dihydro[1,2,4]triazolo[4,3-b]pyridazine

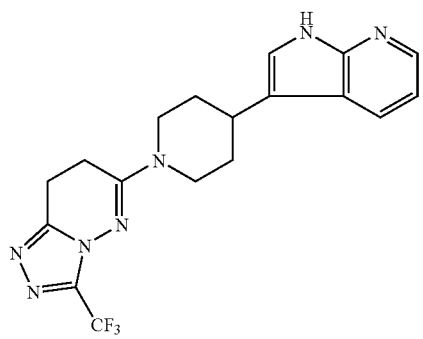

Obtained in 74% yield by an analogous method to Example 3, starting from 6-[4-(1H-pyrrolo[2,3-b]pyridin-3-yl)-3,6-dihydropyridin-1(2H)-yl]-3-(trifluoromethyl)-7,8-dihydro[1,2,4]triazolo[4,3-b]pyridazine (obtained as described in Example 17).

1H NMR (400 MHz, DMSO-d6) d 1.62-1.80 (2H, m), 2.01-2.08 (2H, m), 2.95 (2H, t), 3.03-3.19 (5H, m), 4.22-4.35 (2H, m), 6.97-7.09 (1H, m), 7.24 (1H, d), 7.98-8.09 (1H, m), 8.14-8.24 (1H, m), 11.38 (1H, s); m/z=390 [M+H]+.

Example 19

Preparation of N-(2-methoxyethyl)-N-methyl-2-(4-{1-[3-(trifluoromethyl)-7,8-dihydro[1,2,4]triazolo[4,3-b]pyridazin-6-yl]piperidin-4-yl}phenoxy)acetamide

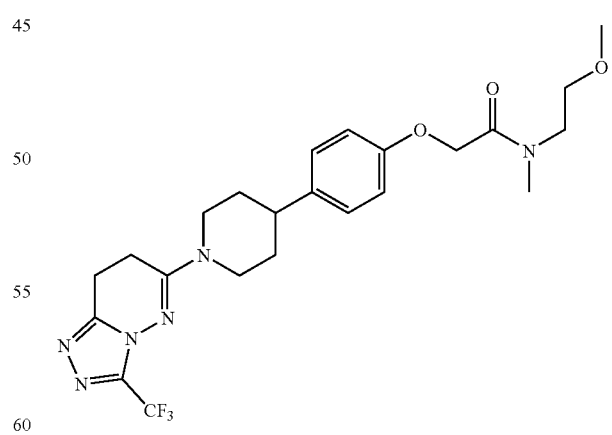

N-(2-methoxyethyl)methylamine (25 mg, 0.28 mmol) was added to 2-[4-[1-[3-(trifluoromethyl)-7,8-dihydro-[1,2,4]triazolo[4,3-b]pyridazin-6-yl]piperidin-4-yl]phenoxy]acetic acid (100 mg, 0.24 mmol), HATU (108 mg, 0.28 mmol) and DIPEA (0.123 mL, 0.71 mmol) in DMF (2 mL). The resulting solution was stirred at ambient temperature for 3 hours then purified by preparative HPLC (Waters XBridge Prep C18 OBD column, 5µ silica, 19 mm diameter, 100 mm length), using decreasingly polar mixtures of water (containing 1% ammonia) and MeCN as eluents. Fractions containing the desired compound were evaporated to dryness to afford N-(2-methoxyethyl)-N-methyl-2-(4-{1-[3-(trifluoromethyl)-7,8-dihydro[1,2,4]triazolo[4,3-b]pyridazin-6-yl]piperidin-4-yl}phenoxy)acetamide (38 mg, 32%) as a solid.

1H NMR (500.133 MHz, DMSO-d6) δ 1.65 (2H, m), 1.87 (2H, m), 2.80 (1H, m), 2.91 (2H, t), 2.96 (3H, s), 3.04 (2H, m), 3.14 (2H, t), 3.28 (3H, s), 3.49 (4H, m), 4.25 (2H, m), 4.71 (2H, s), 6.87 (2H, d), 7.15 (2H, d); m/z=495 [M+H]+.

The 2-[4-[1-[3-(trifluoromethyl)-7,8-dihydro-[1,2,4]triazolo[4,3-b]pyridazin-6-yl]piperidin-4-yl]phenoxy]acetic acid used as starting material was prepared as follows:

Preparation of methyl 2-[4-[1-[3-(trifluoromethyl)-[1,2,4]triazolo[4,3-b]pyridazin-6-yl]piperidin-4-yl]phenoxy]acetate Methyl 2-bromoacetate (0.418 mL, 4.42 mmol) was added to 4-[1-[3-(trifluoromethyl)-[1,2,4]triazolo[4,3-b]pyridazin-6-yl]piperidin-4-yl]phenol (obtained as described in Example 4.2, preparation of starting materials) (1.07 g, 2.94 mmol) and potassium carbonate (0.814 g, 5.89 mmol) in DMF (20 mL). The resulting suspension was stirred at ambient temperature for 16 hours. The reaction mixture was evaporated to dryness then water (50 mL) added and stirring continued for 20 minutes. The resulting precipitate was collected by filtration, washed with water then ether and dried to afford methyl 2-[4-[1-[3-(trifluoromethyl)-[1,2,4]triazolo[4,3-b]pyridazin-6-yl]piperidin-4-yl]phenoxy]acetate (1.290 g, 100%).

1H NMR (399.9 MHz, DMSO-d6) δ 1.67 (2H, m), 1.88 (2H, m), 2.81 (1H, m), 3.09 (2H, m), 3.70 (3H, s), 4.42 (2H, m), 4.77 (2H, s), 6.86 (2H, d), 7.19 (2H, d), 7.67 (1H, d), 8.25 (1H, d); m/z=436 [M+H]+.

Preparation of ethyl 2-[4-[1-[3-(trifluoromethyl)-7,8-dihydro-[1,2,4]triazolo[4,3-b]pyridazin-6-yl]piperidin-4-yl]phenoxy]acetate 10% Palladium on carbon (0.536 g, 0.50 mmol) was added to methyl 2-[4-[1-[3-(trifluoromethyl)-[1,2,4]triazolo[4,3-b]pyridazin-6-yl]piperidin-4-yl]phenoxy]acetate (1.096 g, 2.52 mmol) and ammonium formate (1.587 g, 25.17 mmol) in ethanol (50 mL). The resulting mixture was stirred at 78° C., with further portions of ammonium formate being added every 5 hours until the reaction was complete. The reaction mixture was cooled to room temperature and the catalyst was removed by filtration. The filtrate was evaporated to dryness, redissolved in DCM (100 mL) and the solution was washed with water (50 mL) followed by brine (50 mL), then the solvents were evaporated to give crude product. The crude product was purified by flash silica chromatography, eluting with a gradient of 50 to 80% EtOAc in isohexane. Pure fractions were evaporated to afford ethyl 2-[4-[1-[3-(trifluoromethyl)-7,8-dihydro-[1,2,4]triazolo[4,3-b]pyridazin-6-yl]piperidin-4-yl]phenoxy]acetate (0.820 g, 72.2%) as a gum.

1H NMR (399.9 MHz, DMSO-d6) δ 1.22 (3H, t), 1.62 (2H, m), 1.83 (2H, m), 2.79 (1H, m), 2.92-3.03 (4H, m), 3.16 (2H, t), 4.17 (2H, q), 4.29 (2H, m), 4.74 (2H, s), 6.86 (2H, d), 7.18 (2H, d); m/z=452 [M+H]+.

Preparation of 2-[4-[1-[3-(trifluoromethyl)-7,8-dihydro-[1,2,4]triazolo[4,3-b]pyridazin-6-yl]piperidin-4-yl]phenoxy]acetic acid Lithium hydroxide monohydrate (381 mg, 9.08 mmol) was added to ethyl 2-[4-[1-[3-(trifluoromethyl)-7,8-dihydro-[1,2,4]triazolo[4,3-b]pyridazin-6-yl]piperidin-4-yl]phenoxy]acetate (820 mg, 1.82 mmol) in a mixture of THF (20 mL), water (10 mL) and MeOH (5 mL). The resulting mixture was stirred at ambient temperature for 16 hours. The solvents were evaporated then the residue was suspended in water and acidified to pH 4 with 1M citric acid. The resulting precipitate was collected by filtration, washed with water and dried to afford 2-[4-[1-[3-(trifluoromethyl)-7,8-dihydro-[1,2,4]triazolo[4,3-b]pyridazin-6-yl]piperidin-4-yl]phenoxy]acetic acid (575 mg, 74.8%) as a solid.

1H NMR (399.9 MHz, DMSO-d6) δ 1.62 (2H, m), 1.83 (2H, m), 2.78 (1H, m), 2.92-3.03 (4H, m), 3.16 (2H, t), 4.29 (2H, m), 4.61 (2H, s), 6.84 (2H, d), 7.17 (2H, d); m/z=424 [M+H]+.

Examples 20-22

The following compounds were prepared in 40-57% yield by an analogous method to Example 19, starting from 2-[4-[1-[3-(trifluoromethyl)-7,8-dihydro-[1,2,4]triazolo[4,3-b]pyridazin-6-yl]piperidin-4-yl]phenoxy]acetic acid and the appropriate amine:—

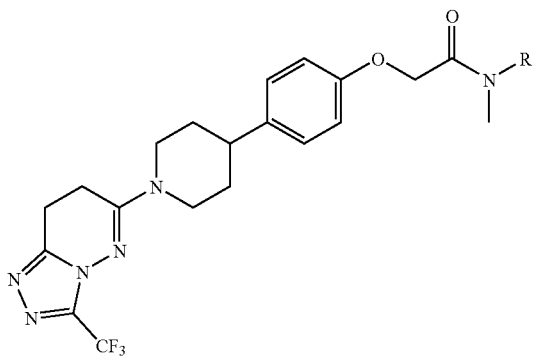

| Ex. | R | 1H NMR(500 MHz, DMSO-d6) | m/z [M + H]+ |
|---|---|---|---|
| 20 | CH3 | δ 1.65(2H, m), 1.87(2H, m), 2.77-2.95(9H, m), 3.04(2H, m), 3.14(2H, t), 4.26(2H, m), 4.69(2H, s), 6.88(2H, d), 7.15(2H, d) | 451 |

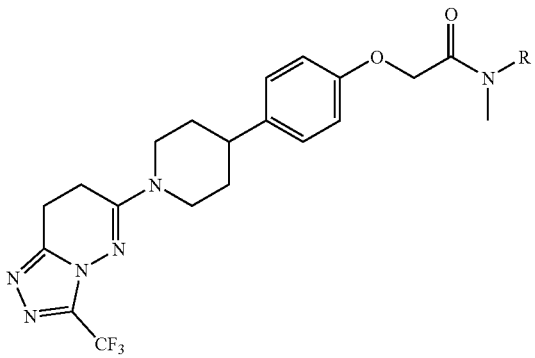

| Ex. | R | 1H NMR(500 MHz, DMSO-d6) | m/z [M + H]+ |
|---|---|---|---|
| 21 | (CH$_2$)$_2$OH | δ 1.64(2H, m), 1.86(2H, m), 2.79(1H, m), 2.91(2H, m), 3.03(2H, m), 3.14(2H, t), 3.40(2H, t), 3.57(2H, m), 4.26(2H, m), 4.73(2H, s), 6.87(2H, d), 7.14 (2H, d)(3H obscured by water in NMR solvent) | 481 |
| 22 | (CH$_2$)$_3$CH$_3$ | δ 0.89(3H, t), 1.28(2H, m), 1.50(2H, m), 1.64(2H, m), 1.86(2H, m), 2.79(1H, m), 2.91(2H, m), 3.03 (2H, m), 3.14(2H, t), 3.30(2H, t), 4.26( 2H, m), 4.69 (2H, s), 6.86(2H, d), 7.15(2H, d)(3H obscured by water in NMR solvent) | 493 |

Example 23

Preparation of N-(2-methoxyethyl)-N-methyl-4-(4-{1-[3-(trifluoromethyl)-7,8-dihydro[1,2,4]triazolo[4,3-b]pyridazin-6-yl]piperidin-4-yl}phenoxy)butanamide

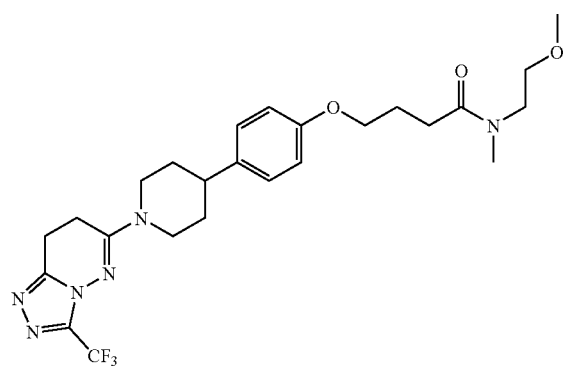

Obtained in 42% yield by an analogous method to Example 4.2, starting from N-(2-methoxyethyl)-N-methyl-4-(4-{1-[3-(trifluoromethyl)[1,2,4]triazolo[4,3-b]pyridazin-6-yl]piperidin-4-yl}phenoxy)butanamide.

1H NMR (399.9 MHz, CDCl3) δ 1.68 (2H, m), 1.94 (2H, m), 2.12 (2H, m), 2.50-2.58 (2H, m), 2.70-2.80 (3H, m), 2.96-3.06 (5H, m), 3.22 (2H, m), 3.32 (3H, m), 3.48-3.57 (4H, m), 4.02 (2H, m), 4.30 (2H, m), 6.86 (2H, d), 7.11 (2H, d); m/z=523 [M+H]+.

The N-(2-methoxyethyl)-N-methyl-4-(4-{1-[3-(trifluoromethyl)[1,2,4]triazolo[4,3-b]pyridazin-6-yl]piperidin-4-yl}phenoxy)butanamide used as starting material was is prepared as follows:

Preparation of methyl 4-[4-[1-[3-(trifluoromethyl)-[1,2,4]triazolo[4,3-b]pyridazin-6-yl]piperidin-4-yl]phenoxy]butanoate Obtained in 63% yield by an analogous method to Example 19, preparation of starting materials, starting from 4-[1-[3-(trifluoromethyl)-[1,2,4]triazolo[4,3-b]pyridazin-6-yl]piperidin-4-yl]phenol and methyl 4-bromobutanoate.

1H NMR (399.9 MHz, DMSO-d6) δ 1.57 (2H, m), 1.82 (4H, m), 2.37 (2H, m), 2.71 (1H, m), 3.01 (2H, m), 3.51 (3H, s), 3.86 (2H, m), 4.31 (2H, m), 6.75 (2H, m), 7.08 (2H, m), 7.57 (1H, d), 8.15 (1H, d); m/z=464 [M+H]+.

Preparation of 4-[4-[1-[3-(trifluoromethyl)-[1,2,4]triazolo[4,3-b]pyridazin-6-yl]piperidin-4-yl]phenoxy]butanoic acid Obtained in 78% yield by an analogous method to Example 19, preparation of starting materials, starting from methyl 4-[4-[1-[3-(trifluoromethyl)-[1,2,4]triazolo[4,3-b]pyridazin-6-yl]piperidin-4-yl]phenoxy]butanoate.

1H NMR (399.9 MHz, DMSO-d6) δ 1.57 (2H, m), 1.81 (4H, m), 2.28 (2H, m), 2.71 (1H, m), 3.00 (2H, m), 3.86 (2H, m), 4.31 (2H, m), 6.76 (2H, m), 7.08 (2H, m), 7.56 (1H, d), 8.14 (1H, d), 12.00 (1H, s); m/z=450 [M+H]+.

Preparation of N-(2-methoxyethyl)-N-methyl-4-(4-{1-[3-(trifluoromethyl)[1,2,4]triazolo[4,3-b]pyridazin-6-yl]piperidin-4-yl}phenoxy)butanamide Obtained in 50% yield by an analogous method to Example 19, starting from 4-[4-[1-[3-(trifluoromethyl)-[1,2,4]triazolo[4,3-b]pyridazin-6-yl]piperidin-4-yl]phenoxy]butanoic acid and N-(2-methoxyethyl)methylamine.

1H NMR (499.803 MHz, DMSO-d6) δ 1.69 (2H, m), 1.94 (4H, m), 2.44 (2H, m), 2.83 (1H, m), 2.94 (3H, s), 3.14 (2H, m), 3.26 (3H, s), 3.45 (4H, s), 3.98 (2H, m), 4.37 (2H, m), 6.85 (2H, m), 7.15 (2H, m), 7.55 (1H, d), 8.13 (1H, d); m/z=521 [M+H]+.

Example 24

Preparation of N-(2-methoxyethyl)-N-methyl-4-(4-{1-[3-(trifluoromethyl)-7,8-dihydro[1,2,4]triazolo[4,3-b]pyridazin-6-yl]piperidin-4-yl}phenoxy)butanamide

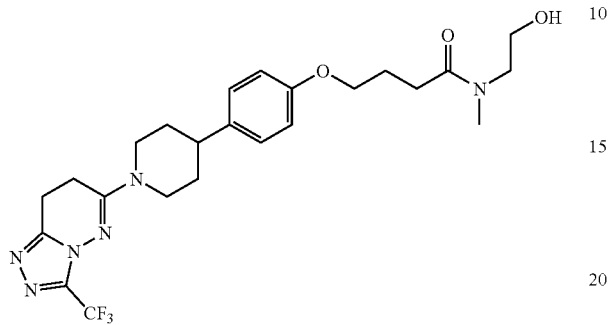

Obtained in 50% yield by an analogous method to Example 4.2, starting from N-(2-hydroxyethyl)-N-methyl-4-(4-{1-[3-(trifluoromethyl)[1,2,4]triazolo[4,3-b]pyridazin-6-yl]piperidin-4-yl}phenoxy)butanamide.

1H NMR (399.9 MHz, CDCl3) δ 1.68 (2H, m), 1.94 (2H, m), 2.13 (2H, m), 2.55 (2H, m), 2.72-2.80 (3H, m), 2.92-3.07 (6H, m), 3.22 (2H, t), 3.56 (2H, t), 3.77 (2H, m), 4.02 (2H, t), 4.31 (2H, m), 6.86 (2H, d), 7.11 (2H, d); m/z=509 [M+H]+.

The N-(2-hydroxyethyl)-N-methyl-4-(4-{1-[3-(trifluoromethyl)[1,2,4]triazolo[4,3-b]pyridazin-6-yl]piperidin-4-yl}phenoxy)butanamide used as starting material was prepared in 39% yield by an analogous method to Example 19, starting from 4-[4-[1-[3-(trifluoromethyl)-[1,2,4]triazolo[4,3-b]pyridazin-6-yl]piperidin-4-yl]phenoxy]butanoic acid (obtained as described in Example 23, preparation of starting materials) and N-(2-hydroxyethyl)methylamine.

Example 25

Preparation of 6-(4-{4-[2-(4-pentanoylpiperazin-1-yl)ethoxy]phenyl}piperidin-1-yl)-3-(trifluoromethyl)-7,8-dihydro[1,2,4]triazolo[4,3-b]pyridazine

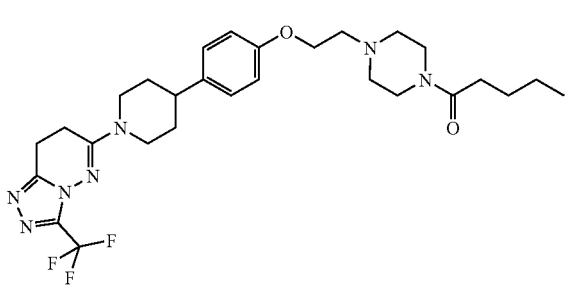

Obtained in 36% yield by an analogous method to Example 4.1, starting from 6-[4-[4-[2-(piperazin-1-yl)ethoxy]phenyl]piperidin-1-yl]-3-(trifluoromethyl)-7,8-dihydro-[1,2,4]triazolo[4,3-b]pyridazine and pentanoic acid.

1H NMR (399.9 MHz, CDCl3) δ 0.93 (3H, t), 1.36 (2H, m), 1.57-1.74 (4H, m), 1.95 (2H, m), 2.31 (2H, m), 2.56 (4H, m), 2.71-2.83 (5H, m), 3.00 (2H, m), 3.22 (2H, t), 3.49 (2H, m), 3.64 (2H, m), 4.10 (2H, t), 4.31 (2H, m), 6.86 (2H, d), 7.12 (2H, d); m/z=562 [M+H]+.

Example 26

Preparation of 6-[4-(4-{2-[4-(methylsulfonyl)piperazin-1-yl]ethoxy}phenyl)piperidin-1-yl]-3-(trifluoromethyl)-7,8-dihydro[1,2,4]triazolo[4,3-b]pyridazine

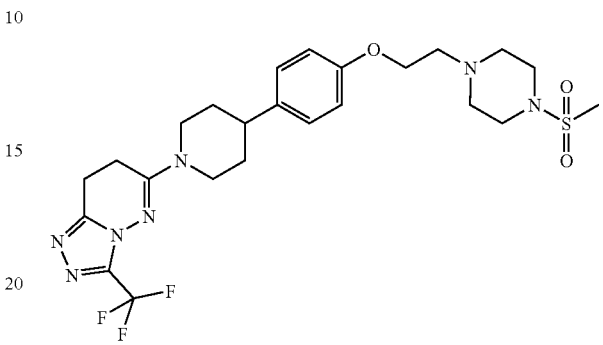

A solution of methanesulfonyl chloride (0.029 mL, 0.38 mmol) in DCM (0.5 mL) was is added dropwise to 6-[4-[4-[2-(piperazin-1-yl)ethoxy]phenyl]piperidin-1-yl]-3-(trifluoromethyl)-7,8-dihydro-[1,2,4]triazolo[4,3-b]pyridazine (obtained as described in Example 5.1, preparation of starting materials) (150 mg, 0.31 mmol) and triethylamine (0.088 mL, 0.63 mmol) in DCM (1 mL) cooled to 0° C. under nitrogen. The resulting solution was stirred at 0° C. for 5 minutes then allowed to warm to room temperature and stirred for a further 15 minutes. The reaction mixture was diluted with water (2 mL), passed through a phase separating cartridge and then the organic layer was evaporated to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-[4-(4-{2-[4-(methylsulfonyl)piperazin-1-yl]ethoxy}phenyl)piperidin-1-yl]-3-(trifluoromethyl)-7,8-dihydro[1,2,4]triazolo[4,3-b]pyridazine (92 mg, 52.7%) as a solid.

1H NMR (399.9 MHz, CDCl3) δ 1.69 (2H, m), 1.95 (2H, m), 2.69-2.80 (10H, m), 2.86 (2H, t), 3.00 (2H, m), 3.20-3.28 (6H, m), 4.09 (2H, t), 4.31 (2H, m), 6.86 (2H, d), 7.12 (2H, d); m/z=556 [M+H]+.

Example 27

Preparation of 6-(4-{4-[3-(4-pentanoylpiperazin-1-yl)propoxy]phenyl}piperidin-1-yl)-3-(trifluoromethyl)-7,8-dihydro[1,2,4]triazolo[4,3-b]pyridazine

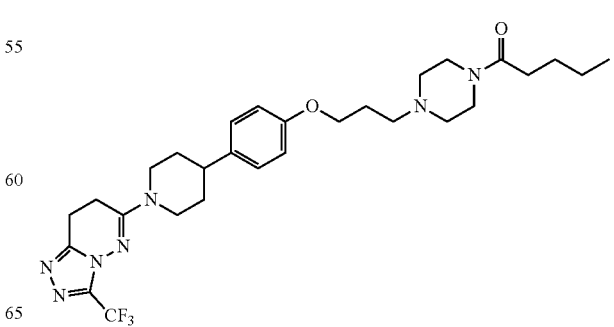

Obtained in 66% yield by an analogous method to Example 4.1, starting from 6-[4-[4-[3-(piperazin-1-yl)propoxy]phenyl]piperidin-1-yl]-3-(trifluoromethyl)-7,8-dihydro-[1,2,4]triazolo[4,3-b]pyridazine and pentanoic acid.

1H NMR (399.9 MHz, CDCl3) δ 0.93 (3H, t), 1.37 (2H, m), 1.57-1.74 (4H, m), 1.92-2.02 (4H, m), 2.32 (2H, m), 2.50 (4H, m), 2.60 (2H, t), 2.71-2.80 (3H, m), 3.00 (2H, m), 3.22 (2H, t), 3.51 (2H, m), 3.65 (2H, m), 4.01 (2H, t), 4.31 (2H, m), 6.85 (2H, d), 7.11 (2H, d); m/z=576 [M+H]+.

Example 28

Preparation of 6-[4-(4-{3-[4-(methylsulfonyl)piperazin-1-yl]propoxy}phenyl)piperidin-1-yl]-3-(trifluoromethyl)-7,8-dihydro[1,2,4]triazolo[4,3-b]pyridazine

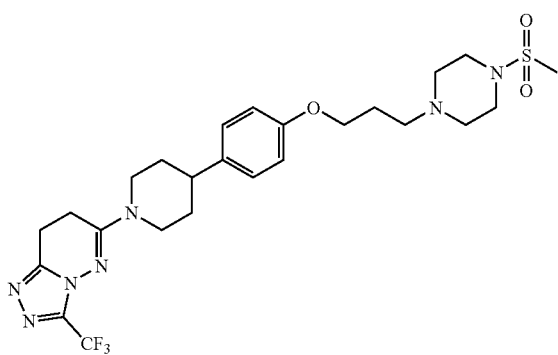

Obtained in 24% yield by an analogous method to Example 26, starting from 6-[4-[4-[3-(piperazin-1-yl)propoxy]phenyl]piperidin-1-yl]-3-(trifluoromethyl)-7,8-dihydro-[1,2,4]triazolo[4,3-b]pyridazine (obtained as described in Example 4.1, preparation of starting materials) and methanesulfonyl chloride.

1H NMR (399.9 MHz, CDCl3) δ 1.69 (2H, m), 1.92-1.97 (4H, m), 2.55-2.60 (6H, m), 2.71-2.80 (6H, m), 3.00 (2H, m), 3.20-3.26 (6H, m), 4.00 (2H, t), 4.31 (2H, m), 6.85 (2H, d), 7.11 (2H, d); m/z=570 [M+H]+.

Example 29

Preparation of 6-(4-{4-[3-(4-acetylpiperazin-1-yl)propoxy]phenyl}piperazin-1-yl)-3-(trifluoromethyl)-7,8-dihydro[1,2,4]triazolo[4,3-b]pyridazine

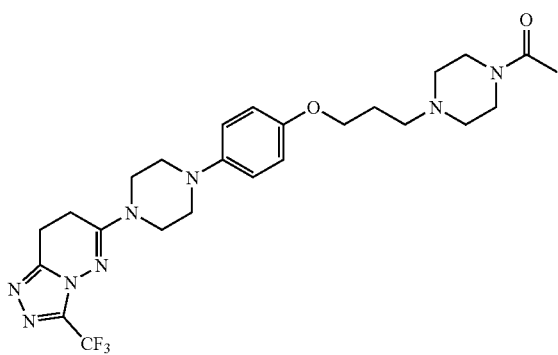

Obtained in 74% yield by an analogous method to Example 4.1, starting from 6-{4-[4-(3-piperazin-1-ylpropoxy)phenyl]piperazin-1-yl}-3-(trifluoromethyl)-7,8-dihydro[1,2,4]triazolo[4,3-b]pyridazine and acetic acid.

1H NMR (399.9 MHz, CDCl3) δ 1.96 (2H, m), 2.08 (3H, s), 2.46 (4H, m), 2.56 (2H, t), 2.79 (2H, t), 3.13 (4H, m), 3.23 (2H, t), 3.47 (2H, m), 3.63 (2H, m), 3.70 (4H, m), 3.99 (2H, t), 6.84-6.92 (4H, m); m/z=535 [M+H]+

The 6-{4-[4-(3-piperazin-1-ylpropoxy)phenyl]piperazin-1-yl}-3-(trifluoromethyl)-7,8-dihydro[1,2,4]triazolo[4,3-b]pyridazine used as starting material was prepared as follows:—

Preparation of tert-butyl 4-[3-(4-{4-[3-(trifluoromethyl)[1,2,4]triazolo[4,3-b]pyridazin-6-yl]piperazin-1-yl}phenoxy)propyl]piperazine-1-carboxylate DIAD (3.24 mL, 16.47 mmol) was added dropwise to 4-{4-[3-(trifluoromethyl)[1,2,4]triazolo[4,3-b]pyridazin-6-yl]piperazin-1-yl}phenol (obtained as described in Example 16, preparation of starting materials) (5 g, 13.72 mmol), tert-butyl 4-(3-hydroxypropyl)piperazine-1-carboxylate (CAS 132710-90-8, 5.03 g, 20.59 mmol) and triphenylphosphine (5.40 g, 20.59 mmol) in THF (50 mL) at 0° C. under nitrogen. The resulting solution was stirred at ambient temperature for 16 hours. The reaction mixture was evaporated to dryness and redissolved in DCM (100 mL), and washed sequentially with 2M NaOH (100 mL) and saturated brine (100 mL). The organic layer was dried over MgSO4, filtered and evaporated to afford crude product. The crude product was purified by flash silica chromatography, eluting with EtOAc. Pure fractions were evaporated to dryness to give tert-butyl 4-[3-(4-{4-[3-(trifluoromethyl)[1,2,4]triazolo[4,3-b]pyridazin-6-yl]piperazin-1-yl}phenoxy)propyl]piperazine-1-carboxylate (3.66 g, 45%).

1H NMR (399.9 MHz, CDCl3) δ 1.46 (9H, s), 1.95 (2H, m), 2.40 (4H, m), 2.52 (2H, t), 3.21 (4H, m), 3.43 (4H, m), 3.78 (4H, m), 3.99 (2H, t), 6.87 (2H, d), 6.93 (2H, d), 7.11 (1H, d), 7.96 (1H, d); m/z=591 [M+H]+.

Preparation of tert-butyl 4-[3-(4-{4-[3-(trifluoromethyl)-7,8-dihydro[1,2,4]triazolo[4,3-b]pyridazin-6-yl]piperazin-1-yl}phenoxy)propyl]piperazine-1-carboxylate Obtained in 29% yield by an analogous method to Example 4.1, preparation of starting materials, starting from tert-butyl 4-[3-(4-{4-[3-(trifluoromethyl)[1,2,4]triazolo[4,3-b]pyridazin-6-yl]piperazin-1-yl}phenoxy)propyl]piperazine-1-carboxylate.

1H NMR (399.9 MHz, CDCl3) δ 1.46 (9H, s), 1.95 (2H, m), 2.40 (4H, m), 2.52 (2H, t), 2.79 (2H, t), 3.13 (4H, m), 3.23 (2H, t), 3.43 (4H, m), 3.70 (4H, m), 3.99 (2H, t), 6.84-6.92 (4H, m); m/z=593 [M+H]+.

Preparation of 6-{4-[4-(3-piperazin-1-ylpropoxy)phenyl]piperazin-1-yl}-3-(trifluoromethyl)-7,8-dihydro[1,2,4]triazolo[4,3-b]pyridazine Obtained in 97% yield by an analogous method to Example 4.1, preparation of starting materials, starting from tert-butyl 4-[3-(4-{4-[3-(trifluoromethyl)-7,8-dihydro[1,2,4]triazolo[4,3-b]pyridazin-6-yl]piperazin-1-yl}phenoxy)propyl]piperazine-1-carboxylate.

m/z=493 [M+H]+.

Example 30

Preparation of 6-(4-{4-[3-(4-pentanoylpiperazin-1-yl)propoxy]phenyl}piperazin-1-yl)-3-(trifluoromethyl)-7,8-dihydro[1,2,4]triazolo[4,3-b]pyridazine

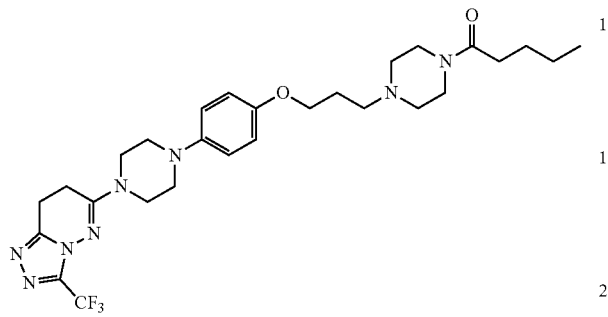

Obtained in 70% yield by an analogous method to Example 4.1, starting from 6-{4-[4-(3-piperazin-1-ylpropoxy)phenyl]piperazin-1-yl}-3-(trifluoromethyl)-7,8-dihydro[1,2,4]triazolo[4,3-b]pyridazine (obtained as described in Example 29, preparation of starting materials) and pentanoic acid.

1H NMR (399.9 MHz, CDCl3) δ 0.93 (3H, t), 1.37 (2H, m), 1.61 (2H, m), 1.95 (2H, m), 2.31 (2H, m), 2.43 (4H, m), 2.53 (2H, t), 2.79 (2H, t), 3.13 (4H, m), 3.23 (2H, t), 3.47 (2H, m), 3.62 (2H, m), 3.70 (4H, m), 3.99 (2H, t), 6.85-6.92 (4H, m); m/z=577 [M+H]+.

Example 31

Preparation of 6-[4-(4-{3-[4-(methylsulfonyl)piperazin-1-yl]propoxy}phenyl)piperidin-1-yl]-3-(trifluoromethyl)-7,8-dihydro[1,2,4]triazolo[4,3-b]pyridazine

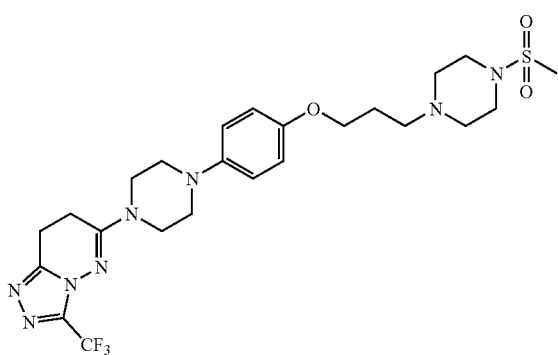

Obtained in 55% yield by an analogous method to Example 26, starting from 6-{4-[4-(3-piperazin-1-ylpropoxy)phenyl]piperazin-1-yl}-3-(trifluoromethyl)-7,8-dihydro[1,2,4]triazolo[4,3-b]pyridazine (obtained as described in Example 29, preparation of starting materials) and methanesulfonyl chloride.

1H NMR (399.9 MHz, CDCl3) δ 1.95 (2H, m), 2.58 (6H, m), 2.77-2.81 (5H, m), 3.14 (4H, m), 3.21-3.26 (6H, m), 3.70 (4H, m), 3.98 (2H, t), 6.84-6.92 (4H, m); m/z=571 [M+H]+.

Example 32

Preparation of 6-(4-{4-[2-(4-acetylpiperazin-1-yl)ethoxy]phenyl}piperazin-1-yl)-3-(trifluoromethyl)-7,8-dihydro[1,2,4]triazolo[4,3-b]pyridazine

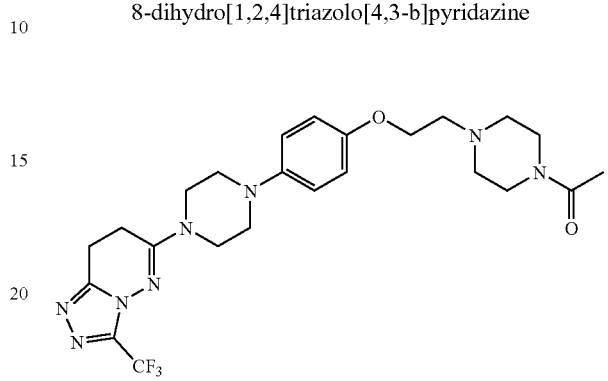

Obtained in 78% yield by an analogous method to Example 4.1, starting from 6-[4-[4-[2-(piperazin-1-yl)ethoxy]phenyl]piperazin-1-yl]-3-(trifluoromethyl)-7,8-dihydro-[1,2,4]triazolo[4,3-b]pyridazine and acetic acid.

1H NMR (399.9 MHz, CDCl3) δ 2.08 (3H, s), 2.53-2.60 (4H, m), 2.77-2.83 (4H, m), 3.14 (4H, m), 3.23 (2H, t), 3.48 (2H, m), 3.64 (2H, m), 3.71 (4H, m), 4.08 (2H, t), 6.85-6.92 (4H, m); m/z=521 [M+H]+.

The 6-[4-[4-[2-(piperazin-1-yl)ethoxy]phenyl]piperazin-1-yl]-3-(trifluoromethyl)-7,8-dihydro-[1,2,4]triazolo[4,3-b]pyridazine used as starting material was prepared as follows:—

Preparation of tert-butyl 4-[2-(4-{4-[3-(trifluoromethyl)[1,2,4]triazolo[4,3-b]pyridazin-6-yl]piperazin-1-yl}phenoxy)ethyl]piperazine-1-carboxylate Obtained in 60% yield by an analogous method to Example 29, preparation of starting materials, starting from 4-{4-[3-(trifluoromethyl)[1,2,4]triazolo[4,3-b]pyridazin-6-yl]piperazin-1-yl}phenol (obtained as described in Example 16, preparation of starting materials) and tert-butyl 4-(2-hydroxyethyl)piperazine-1-carboxylate (CAS 77279-24-4).

1H NMR (399.9 MHz, CDCl3) δ 1.46 (9H, s), 2.52 (4H, m), 2.80 (2H, t), 3.21 (4H, m), 3.45 (4H, m), 3.78 (4H, m), 4.08 (2H, t), 6.88 (2H, d), 6.93 (2H, d), 7.11 (1H, d), 7.96 (1H, d); m/z=577 [M+H]+.

Preparation of tert-butyl 4-[2-(4-{4-[3-(trifluoromethyl)-7,8-dihydro[1,2,4]triazolo[4,3-b]pyridazin-6-yl]piperazin-1-yl}phenoxy)ethyl]piperazine-1-carboxylate Obtained in 82% yield by an analogous method to Example 4.1, preparation of starting materials, starting from tert-butyl 4-[2-(4-{4-[3-(trifluoromethyl)[1,2,4]triazolo[4,3-b]pyridazin-6-yl]piperazin-1-yl}phenoxy)ethyl]piperazine-1-carboxylate.

1H NMR (399.9 MHz, CDCl3) δ 1.46 (9H, s), 2.52 (4H, m), 2.79 (4H, m), 3.14 (4H, m), 3.23 (2H, t), 3.45 (4H, m), 3.70 (4H, m), 4.07 (2H, t), 6.89 (4H, m); m/z=579 [M+H]+.

Preparation of 6-{4-[4-(2-piperazin-1-ylethoxy)phenyl]piperazin-1-yl}-3-(trifluoromethyl)-7,8-dihydro[1,2,4]triazolo[4,3-b]pyridazine Obtained in 96% yield by an analogous method to Example 4.1, preparation of starting materials, starting from tert-butyl 4-[2-(4-{4-[3-(trifluoromethyl)-7,8-dihydro[1,2,4]triazolo[4,3-b]pyridazin-6-yl]piperazin-1-yl}phenoxy)ethyl]piperazine-1-carboxylate.

1H NMR (399.9 MHz, CDCl3) δ 2.55 (4H, m), 2.79 (4H, m), 2.91 (4H, m), 3.14 (4H, m), 3.23 (2H, t), 3.70 (4H, m), 4.07 (2H, t), 6.89 (4H, m); m/z=479 [M+H]+.

Example 33

Preparation of 6-(4-{4-[2-(4-pentanoylpiperazin-1-yl)ethoxy]phenyl}piperazin-1-yl)-3-(trifluoromethyl)-7,8-dihydro[1,2,4]triazolo[4,3-b]pyridazine

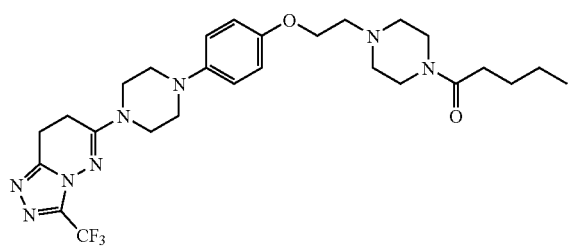

Obtained in 77% yield by an analogous method to Example 4.1, starting from 6-[4-[4-[2-(piperazin-1-yl)ethoxy]phenyl]piperazin-1-yl]-3-(trifluoromethyl)-7,8-dihydro-[1,2,4]triazolo[4,3-b]pyridazine (obtained as described in Example 32, preparation of starting materials) and pentanoic acid.

1H NMR (399.9 MHz, CDCl3) δ 0.93 (3H, t), 1.36 (2H, m), 1.61 (2H, m), 2.32 (2H, m), 2.59 (4H, m), 2.77-2.85 (4H, m), 3.14 (4H, m), 3.23 (2H, t), 3.51 (2H, m), 3.65-3.72 (6H, m), 4.09 (2H, t), 6.85-6.92 (4H, m); m/z=563 [M+H]+.

Example 34

Preparation of 6-[4-(4-{2-[4-(methylsulfonyl)piperazin-1-yl]ethoxy}phenyl)piperazin-1-yl]-3-(trifluoromethyl)-7,8-dihydro[1,2,4]triazolo[4,3-b]pyridazine

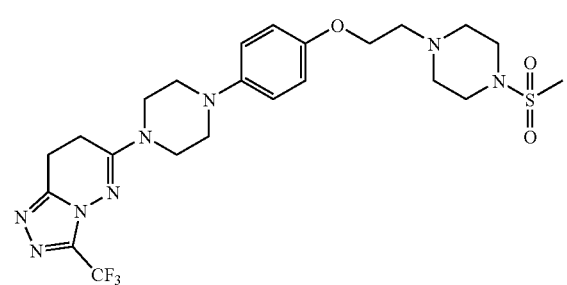

Obtained in 75% yield by an analogous method to Example 26, starting from 6-[4-[4-[2-(piperazin-1-yl)ethoxy]phenyl]piperazin-1-yl]-3-(trifluoromethyl)-7,8-dihydro-[1,2,4]triazolo[4,3-b]pyridazine (obtained as described in Example 32, preparation of starting materials) and methanesulfonyl chloride.

1H NMR (399.9 MHz, CDCl3) δ 2.70 (4H, m), 2.78-2.81 (5H, m), 2.85 (2H, t), 3.14 (4H, m), 3.21-3.28 (6H, m), 3.71 (4H, m), 4.07 (2H, t), 6.85-6.92 (4H, m); m/z=557 [M+H]+.

Example 35

Preparation of 6-{4-[4-(4,4,4-trifluorobutoxy)phenyl]piperidin-1-yl}-3-(trifluoromethyl)-7,8-dihydro[1,2,4]triazolo[4,3-b]pyridazine

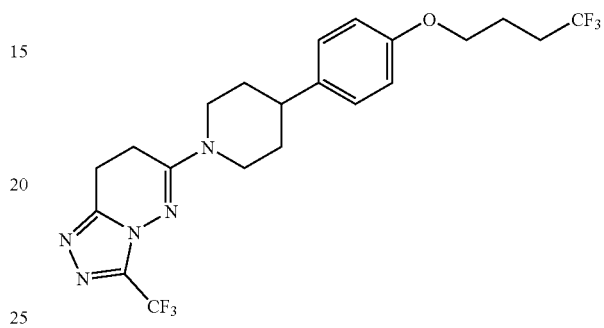

Obtained in 81% yield by an analogous method to Example 4.2, starting from 6-{4-[4-(4,4,4-trifluorobutoxy)phenyl]piperidin-1-yl}-3-(trifluoromethyl)[1,2,4]triazolo[4,3-b]pyridazine.

1H NMR (399.9 MHz, CDCl3) δ 1.69 (2H, m), 1.95 (2H, m), 2.04 (2H, m), 2.31 (2H, m), 2.71-2.80 (3H, m), 3.00 (2H, m), 3.22 (2H, t), 4.00 (2H, t), 4.31 (2H, m), 6.85 (2H, d), 7.12 (2H, d); m/z=476 [M+H]+.

The 6-{4-[4-(4,4,4-trifluorobutoxy)phenyl]piperidin-1-yl}-3-(trifluoromethyl)[1,2,4]triazolo[4,3-b]pyridazine used as starting material was prepared as follows:—

Preparation of 6-{4-[4-(4,4,4-trifluorobutoxy)phenyl]piperidin-1-yl}-3-(trifluoromethyl)[1,2,4]triazolo[4,3-b]pyridazine 4-[1-[3-(trifluoromethyl)[1,2,4]triazolo[4,3-b]pyridazin-6-yl]piperidin-4-yl]phenol (obtained as described in Example 5.2, preparation of starting materials) (200 mg, 0.55 mmol), 4-bromo-1,1,1-trifluorobutane (526 mg, 2.75 mmol) and potassium carbonate (152 mg, 1.10 mmol) were suspended in DMA (4 mL) and sealed into a microwave tube. The reaction was heated to 200° C. for 30 minutes in the microwave reactor and cooled to room temperature. The mixture was evaporated to dryness and redissolved in DCM (20 mL) and the solution was washed with water (20 mL). The organic layer was dried over MgSO4, filtered and evaporated to afford crude product. The crude product was purified by preparative HPLC (Waters XBridge Prep C18 OBD column, 5μ silica, 19 mm diameter, 100 mm length), using decreasingly polar mixtures of water (containing 1% ammonia) and MeCN as eluents. Fractions containing the desired compound were evaporated to dryness to afford 6-{4-[4-(4,4,4-trifluorobutoxy)phenyl]piperidin-1-yl}-3-(trifluoromethyl)[1,2,4]triazolo[4,3-b]pyridazine (95 mg, 37%) as a solid.

1H NMR (399.9 MHz, DMSO-d6) δ 1.66 (2H, m), 1.91 (4H, m), 2.38-2.47 (2H, m), 2.81 (1H, m), 3.10 (2H, m), 4.01 (2H, t), 4.41 (2H, m), 6.88 (2H, d), 7.19 (2H, d), 7.66 (1H, d), 8.24 (1H, d); m/z=474 [M+H]+.

Example 36

Preparation of 4-{4-[2-(1-methyl-1H-pyrazol-5-yl)ethoxy]phenyl}-1-[3-(trifluoromethyl)-7,8-dihydro[1,2,4]triazolo[4,3-b]pyridazin-6-yl]piperidin-4-ol

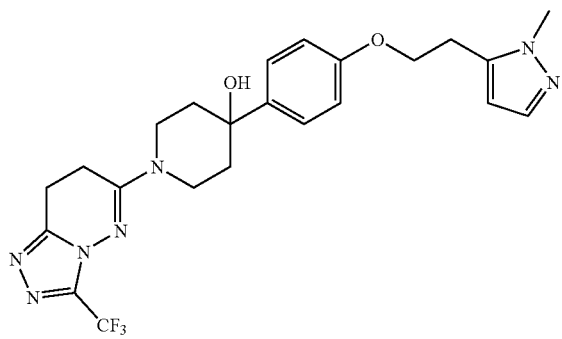

Obtained in 72% yield by an analogous method to Example 4.2, starting from 4-{4-[2-(1-methyl-1H-pyrazol-5-yl)ethoxy]phenyl}-1-[3-(trifluoromethyl)[1,2,4]triazolo[4,3-b]pyridazin-6-yl]piperidin-4-ol.

1H NMR (399.9 MHz, DMSO-d6) δ 1.66 (2H, m), 1.94 (2H, m), 2.94 (2H, t), 3.09 (2H, t), 3.16 (2H, t), 3.36 (2H, m), 3.80 (3H, s), 4.06 (2H, m), 4.20 (2H, t), 5.09 (1H, s), 6.14 (1H, s), 6.91 (2H, d), 7.30 (1H, s), 7.40 (2H, d); m/z=490 [M+H]+.

The 4-{4-[2-(1-methyl-1H-pyrazol-5-yl)ethoxy]phenyl}-1-[3-(trifluoromethyl)[1,2,4]triazolo[4,3-b]pyridazin-6-yl]piperidin-4-ol used as starting material was prepared as follows:—

Preparation of benzyl 4-[4-(benzyloxy)phenyl]-4-hydroxypiperidine-1-carboxylate n-Butyllithium (1.6M in hexane, 42.9 ml, 107.18 mmol) was added dropwise to 1-(benzyloxy)-4-bromobenzene (28.2 g, 107.18 mmol, CAS 6793-92-6) in THF (367 ml) at −78° C. over a period of 15 minutes under nitrogen. The resulting solution was stirred at −78° C. for 1 hour then benzyl 4-oxopiperidine-1-carboxylate (20 g, 85.74 mmol) in THF (122 ml) was added dropwise. The resulting mixture was stirred at −78° C. for 10 minutes, then allowed to warm to room temperature and stirred for 16 hours. The reaction mixture was evaporated to dryness and quenched with saturated ammonium chloride (50 mL), then then extracted with EtOAc (500 mL). The organic layer was dried over MgSO4, filtered and evaporated to afford crude product. The crude product was purified by flash silica chromatography, elution gradient 1 to 100% EtOAc in isohexane. Pure fractions were evaporated to dryness to afford crude product. The crude product was further purified by flash silica chromatography, elution gradient 0 to 3% MeOH in DCM. Pure fractions were evaporated to dryness to afford benzyl 4-[4-(benzyloxy)phenyl]-4-hydroxypiperidine-1-carboxylate (13.49 g, 30.1%) as a gum.

1H NMR (399.9 MHz, DMSO-d6) δ 1.58 (2H, m), 1.80 (2H, m), 3.27 (2H, m), 3.71 (1H, m), 3.92 (2H, m), 5.10 (4H, m), 6.95 (2H, m), 7.39 (12H, m); m/z=416 [M−H]+.

Preparation of 4-(4-hydroxyphenyl)piperidin-4-ol

10% Palladium on carbon (3.44 g, 3.23 mmol) was added to benzyl 4-[4-(benzyloxy)phenyl]-4-hydroxypiperidine-1-carboxylate (13.49 g, 32.31 mmol) in MeOH (146 mL). The resulting mixture was stirred at room temperature for 20 hours under an atmosphere of hydrogen. The reaction mixture was filtered and evaporated to afford crude product. The crude material was triturated with DCM (100 mL) and MeOH (50 mL) to give a solid which was collected by filtration and dried under vacuum to give 4-(4-hydroxyphenyl)piperidin-4-ol (4.16 g, 66.6%). The preparation of 4-(4-hydroxyphenyl)piperidin-4-ol is also described in Journal of Medicinal Chemistry (2000), 43(5), 984-994.

1H NMR (399.9 MHz, DMSO-d6) δ 1.50 (2H, m), 1.73 (2H, m), 2.70 (2H, m), 2.90 (2H, m), 4.52 (1H, s), 6.69 (2H, m), 7.25 (2H, m), 9.21 (1H, s); m/z=192 [M−H]+.

Preparation of 4-(4-hydroxyphenyl)-1-[3-(trifluoromethyl)[1,2,4]triazolo[4,3-b]pyridazin-6-yl]piperidin-4-ol DIPEA (1.174 mL, 6.74 mmol) was added to 6-chloro-3-(trifluoromethyl)-[1,2,4]triazolo[4,3-b]pyridazine (obtained as described in Monatsh. Chem. 1972, 103, 1591) (1 g, 4.49 mmol) and 4-(4-hydroxyphenyl)piperidin-4-ol (0.955 g, 4.94 mmol) in DMF (10 mL). The resulting solution was stirred at 80° C. for 1 hour. The reaction mixture was cooled to room temperature then evaporated to dryness. The residues were triturated with water and the resulting solid collected by filtration, washed with further water followed by ether, then dried under vacuum to afford 4-(4-hydroxyphenyl)-1-[3-(trifluoromethyl)[1,2,4]triazolo[4,3-b]pyridazin-6-yl]piperidin-4-ol (1.680 g, 99%) as a solid.

1H NMR (399.9 MHz, DMSO-d6) δ 1.72 (2H, m), 1.95 (2H, m), 3.42 (2H, m), 4.17 (2H, m), 5.01 (1H, s), 6.70 (2H, d), 7.28 (2H, d), 7.65 (1H, d), 8.23 (1H, d), 9.20 (1H, s); m/z=380 [M+H]+.

Preparation of 4-{4-[2-(1-methyl-1H-pyrazol-5-yl)ethoxy]phenyl}-1-[3-(trifluoromethyl)[1,2,4]triazolo[4,3-b]pyridazin-6-yl]piperidin-4-ol DIAD (0.311 mL, 1.58 mmol) was added dropwise to 4-(4-hydroxyphenyl)-1-[3-(trifluoromethyl)[1,2,4]triazolo[4,3-b]pyridazin-6-yl]piperidin-4-ol (500 mg, 1.32 mmol), 2-(1-methyl-1H-pyrazol-5-yl)ethanol (obtained as described in Example 15, preparation of starting materials) (249 mg, 1.98 mmol) and triphenylphosphine (519 mg, 1.98 mmol) in THF (10 mL) under nitrogen. The resulting suspension was stirred at ambient temperature for 16 hours then the solvents were evaporated to give crude product. The crude product was purified by flash silica chromatography, eluting with EtOAc then a gradient of 3 to 5% MeOH in DCM. Pure fractions were evaporated to dryness to give a solid which was triturated with ether, filtered and dried to give 4-[4-[2-(1-methyl-1H-pyrazol-5-yl)ethoxy]phenyl]-1-[3-(trifluoromethyl)[1,2,4]triazolo[4,3-b]pyridazin-6-yl]piperidin-4-ol (464 mg, 72.2%) as a solid.

1H NMR (399.9 MHz, DMSO-d6) δ 1.72 (2H, m), 1.99 (2H, m), 3.09 (2H, t), 3.43 (2H, m), 3.79 (3H, s), 4.18 (4H, m), 5.12 (1H, s), 6.13 (1H, d), 6.90 (2H, d), 7.30 (1H, d), 7.41 (2H, d), 7.65 (1H, d), 8.23 (1H, d); m/z=488 [M+H]+.

Example 37

Preparation of 1-methyl-4-[2-(4-{1-[3-(trifluoromethyl)-7,8-dihydro[1,2,4]triazolo[4,3-b]pyridazin-6-yl]piperidin-4-yl}phenoxy)ethyl]piperazin-2-one

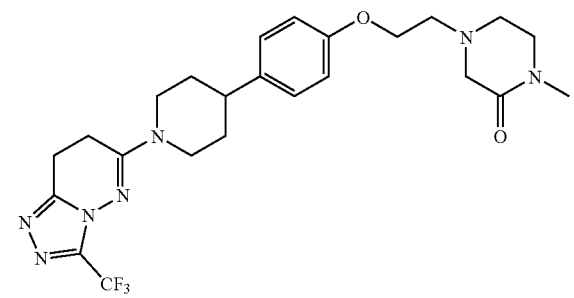

Obtained in 49% yield by an analogous method to Example 4.2, starting from 1-methyl-4-[2-(4-{1-[3-(trifluoromethyl)[1,2,4]triazolo[4,3-b]pyridazin-6-yl]piperidin-4-yl}phenoxy)ethyl]piperazin-2-one.

1H NMR (399.9 MHz, CDCl3) δ 1.69 (2H, m), 1.95 (2H, m), 2.71-2.88 (7H, m), 2.95 (3H, s), 3.00 (2H, m), 3.22 (2H, t), 3.27-3.36 (4H, m), 4.10 (2H, t), 4.30 (2H, m), 6.86 (2H, d), 7.12 (2H, d); m/z=506 [M+H]+.

The 1-methyl-4-[2-(4-{1-[3-(trifluoromethyl)[1,2,4]triazolo[4,3-b]pyridazin-6-yl]piperidin-4-yl}phenoxy)ethyl]piperazin-2-one used as starting material was prepared as follows:—

Preparation of 2-(4-{1-[3-(trifluoromethyl)[1,2,4]triazolo[4,3-b]pyridazin-6-yl]piperidin-4-yl}phenoxy)ethanol A solution of ethylene carbonate (18.18 g, 206.42 mmol) in DMF (30 mL) was added dropwise to a stirred suspension of 4-{1-[3-(trifluoromethyl)[1,2,4]triazolo[4,3-b]pyridazin-6-yl]piperidin-4-yl}phenol (obtained as described in Example 4.2, preparation of starting materials) (15 g, 41.28 mmol) and potassium carbonate (11.41 g, 82.57 mmol) in DMF (30 mL) at 80° C. over a period of 10 minutes under nitrogen. The resulting mixture was stirred at 80° C. for 20 hours. The reaction mixture was cooled to room temperature then concentrated and diluted with DCM (500 mL), and washed sequentially with water (500 mL) and saturated brine (250 mL). The organic layer was dried over MgSO4, filtered and evaporated to afford crude product. The crude product was purified by flash silica chromatography, elution gradient 70 to 100% EtOAc in isohexane. Pure fractions were evaporated to dryness to give 2-(4-{1-[3-(trifluoromethyl)[1,2,4]triazolo[4,3-b]pyridazin-6-yl]piperidin-4-yl}phenoxy)ethanol (12.04 g, 71.6%) as a solid.

1H NMR (399.9 MHz, DMSO-d6) δ 1.67 (2H, m), 1.89 (2H, m), 2.81 (1H, m), 3.10 (2H, m), 3.70 (2H, m), 3.95 (2H, t), 4.41 (2H, m), 4.81 (1H, t), 6.87 (2H, d), 7.18 (2H, d), 7.66 (1H, d), 8.24 (1H, d); m/z=408 [M+H]+.

Preparation of 2-(4-{1-[3-(trifluoromethyl)[1,2,4]triazolo[4,3-b]pyridazin-6-yl]piperidin-4-yl}phenoxy)ethyl methanesulfonate A solution of methanesulfonyl chloride (2.74 mL, 35.46 mmol) in DCM (40 mL) was added dropwise to a stirred solution of 2-(4-{1-[3-(trifluoromethyl)[1,2,4]triazolo[4,3-b]pyridazin-6-yl]piperidin-4-yl}phenoxy)ethanol (12.04 g, 29.55 mmol) and triethylamine (8.24 mL, 59.11 mmol) in DCM (120 mL) cooled to 0° C. under nitrogen. The resulting solution was stirred at 0° C. for 15 minutes then warmed to room temperature and stirred for a further 15 minutes. The reaction mixture was diluted with DCM (100 mL), and washed with water (250 mL) and saturated brine (100 mL). The organic layer was dried over MgSO4, filtered and evaporated to give 2-(4-{1-[3-(trifluoromethyl)[1,2,4]triazolo[4,3-b]pyridazin-6-yl]piperidin-4-yl}phenoxy)ethyl methanesulfonate (14.32 g, 100%) as a solid.

1H NMR (399.9 MHz, CDCl3) δ 1.70 (2H, m), 1.93 (2H, m), 2.73 (1H, m), 3.00-3.08 (5H, m), 4.17 (2H, m), 4.30 (2H, m), 4.49 (2H, m), 6.80 (2H, d), 7.04-7.10 (3H, m), 7.86 (1H, d); m/z=486 [M+H]+.

Preparation of 1-methyl-4-[2-(4-{1-[3-(trifluoromethyl)[1,2,4]triazolo[4,3-b]pyridazin-6-yl]piperidin-4-yl}phenoxy)ethyl]piperazin-2-one DIPEA (15.27 mL, 87.69 mmol) was added to 2-(4-{1-[3-(trifluoromethyl)[1,2,4]triazolo[4,3-b]pyridazin-6-yl]piperidin-4-yl}phenoxy)ethyl methanesulfonate (14.19 g, 29.23 mmol) and 1-methylpiperazin-2-one (CAS 59702-07-7, 3.67 g, 32.15 mmol) in DMA (70 mL). The resulting solution was stirred at 110° C. for 1 hour. The reaction mixture was cooled to room temperature, absorbed onto silica, evaporated to dryness and then purified by flash silica chromatography, elution gradient 0 to 3% MeOH in DCM. Pure fractions were evaporated and the resulting gum was scratched with ether until solid. The solid was stirred in ether (100 mL) for 4 hours then collected by filtration and dried to give 1-methyl-4-[2-(4-{1-[3-(trifluoromethyl)[1,2,4]triazolo[4,3-b]pyridazin-6-yl]piperidin-4-yl}phenoxy)ethyl]piperazin-2-one (10.08 g, 68.5%) as a solid.

1H NMR (399.9 MHz, CDCl3) δ 1.76 (2H, m), 2.00 (2H, m), 2.75-2.87 (5H, m), 2.95 (3H, s), 3.11 (2H, m), 3.28 (2H, s), 3.34 (2H, t), 4.09 (2H, t), 4.37 (2H, m), 6.86 (2H, d), 7.11-7.14 (3H, m), 7.92 (1H, d); m/z=504 [M+H]+.

Examples 38-40

The following compounds were prepared in 28-31% yield by an analogous method to Example 4.2, starting from the appropriate triazolopyridazine:

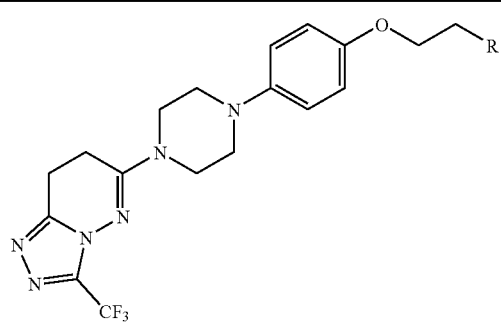

| Ex. | R | 1H NMR(399.9 MHz, DMSO-d6) | m/z [M + H]+ |
|---|---|---|---|
| 38 | 1-imidazolyl | δ 2.90-2.99(2H, m), 3.06-3.19(6H, m), 3.62-3.71(4H, m), 4.20(2H, t), 4.32(2H, t), 6.81-6.97 (5H, m), 7.23(1H, s) and 7.68(1H, s). | 462 |

-continued

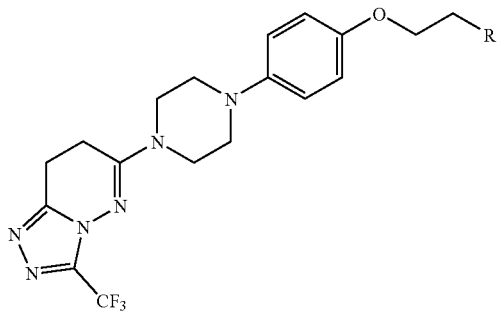

| Ex. | R | 1H NMR(399.9 MHz, DMSO-d6) | m/z [M + H]+ |
|---|---|---|---|
| 39 | 2-ethyl-1-imidazol-yl | δ 1.23(3H, t), 2.68(2H, q), 2.96(2H, q), 3.06-3.19(6H, m), 3.66(4H, t), 4.16(2H, t), 4.25(2H, t), 6.76(1H, s), 6.84(2H, d), 6.95(2H, d) and 7.10(1H, s). | 490 |
| 42 | 3-trifluoro-methyl-1-pyrazolyl | δ 2.90-2.99(2H, m), 3.08-3.22(6H, m), 3.63-3.74(4H, m), 4.32(2H, t), 4.56(2H, t), 6.72(1H, d), 6.85(2H, d), 6.93(2H, d), and 8.04(1H, s). | 530 |

The starting materials used in Example 38-40 were prepared in 6-20% yield by an analogous method to Example 16, preparation of starting materials, starting from 4-[4-[3-(trifluoromethyl)[1,2,4]triazolo[4,3-b]pyridazin-6-yl]piperazin-1-yl]phenol and the appropriate alcohol:—

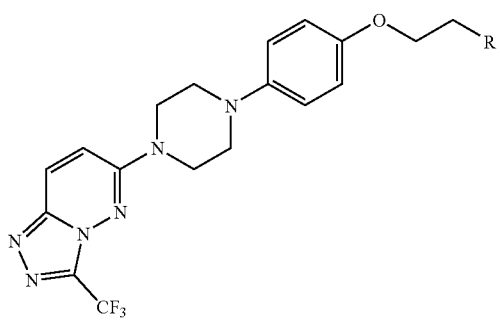

| Precursor to Ex. | R | 1H NMR(399.9 MHz, DMSO-d6) | m/z [M + H]+ |
|---|---|---|---|
| 38 | 1-imidazolyl | δ 3.18(4H, t), 3.76(1H, t), 4.18 (2H, t), 4.33(2H, t), 6.82-6.99(5H, m), 7.26(1H, s), 7.53-7.72(2H, m), 8.29(1H, d) | 460 |
| 39 | 2-ethyl-1-imidazol-yl | δ 1.23(3H, t), 2.69(2H, q), 3.15 (4H, t), 3.75(4H, t), 4.13(2H, t), 4.22(1H, t), 6.77(1H, s), 6.82(2H, d), 6.96(2H, d), 7.12(2H, d), 7.67 (2H, d) and 8.28(1H, d). | 488 |
| 40 | 3-trifluoro-methyl-1-pyrazolyl | δ 3.17(4H, t), 3.75(4H, t), 4.32 (2H, t), 4.56(2H, t), 6.74(1H, d), 6.86(2H, d), 6.97(2H, d), 7.67 (1H, d), 8.02(1H, d) and 8.29(1H, d). | 528 |

Examples 41-44

The following compounds were prepared in 20-48% yield by an analogous method to Example 4.2, starting from the appropriate triazolopyridazine:

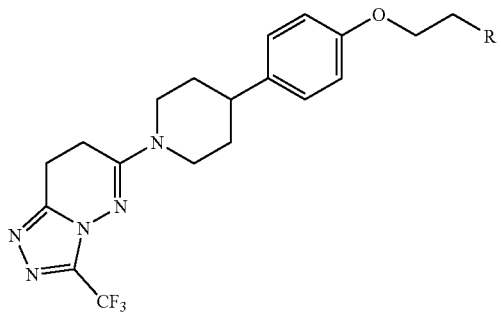

| Ex. | R | 1H NMR(399.9 MHz, DMSO-d6) | m/z [M + H]+ |
|---|---|---|---|
| 41 | 1-imidazolyl | δ 1.55-1.68(2H, m), 1.80(2H, d), 2.74-2.84 (1H, m), 2.91-3.07(4H, m), 3.12-3.22(2H, m), 4.19-4.38(6H, m), 6.85-6.93(3H, m), 7.18(2H, d), 7.24(1H, s) and 7.68(1H, s). | 461 |
| 42 | 2-ethyl-1-imidazol-yl | δ 1.24(3H, t), 1.55-1.68(2H, m), 1.80(2H, d), 2.68(2H, q), 2.75-2.81(1H, m), 2.91-3.04 (4H, m), 3.14(2H, t), 4.15-4.35(6H, m), 6.76 (1H, s), 6.86(2H, d), 7.12(1H, s) and 7.18 (2H, d). | 489 |
| 43 | 3,5-dimethyl-1-pyrazolyl | δ 1.55-1.68(2H, m), 1.82(2H, d), 2.08(3H, s), 2.26(3H, s), 2.73-2.85(1H, m), 2.92-3.06 (4H, m), 3.18(2H, t), 4.19-4.33(6H, m), 5.80 (1H, s), 6.84(2H, d), and 7.16(2H, d). | 489 |
| 44 | 3-trifluoro-methyl-1-pyrazolyl | δ 1.53-1.76(2H, m), 1.88(2H, d), 2.81-2.91 (1H, m), 2.98-3.13(4H, m), 3.23(2H, t), 4.32-4.47(4H, m), 4.63(2H, t), 6.79(1H, s), 6.94(2H, d), 7.25(2H, d) and 8.10(1H, s). | 529 |

The starting materials used in Example 41-44 were prepared in 15-38% yield by an analogous method to Example 15, preparation of starting materials, starting from 4-[1-[3-(trifluoromethyl)[1,2,4]triazolo[4,3-b]pyridazin-6-yl]piperidin-4-yl]phenol and the appropriate alcohol:—

| Precursor to Ex. | R | 1H NMR(399.9 MHz, DMSO-d6) | m/z [M + H]+ |
|---|---|---|---|
| 41 | 1-imidazolyl | δ 1.58-1.73(2H, m), 1.86(2H, d), 2.76- | 459 |
| 42 | 2-ethyl-1-imidazol-yl | δ 1.19(3H, t), 1.58-1.74(2H, m), 1.85(2H, d), 2.67(2H, q), 2.77-2.85(1H, m), 3.04-3.16(2H, m), 4.15-4.29(4H, m), 4.39(2H, d), 6.75(1H, d), 6.84(2H, d), 7.09 (1H, d), 7.17(2H, d), 7.65(2H, d) and 8.23(2H, d). | 487 |
| 43 | 3,5-dimethyl-1-pyrazolyl | δ 1.59-1.72(2H, m), 1.87(2H, d), 2.09(3H, s), 2.26(3H, s), 2.76-2.86(1H, m), 3.05-3.16 (2H, m), 4.21-4.30(4H, m), 4.41 (2H, d), 5.79(1H, s), 6.83(2H, d), 7.16(2H, d), 7.64(1H, d) and 8.24(1H, d). | 486 |

-continued

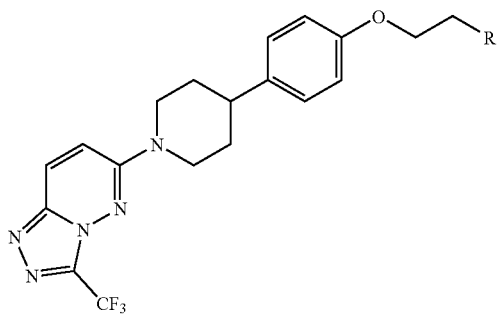

| Precursor to Ex. | R | 1H NMR(399.9 MHz, DMSO-d6) | m/z [M + H]+ |
| --- | --- | --- | --- |
| 44 | 3-trifluoromethyl-1-pyrazolyl | δ 1.59-1.73(2H, m), 1.85(2H, d), 2.76-2.87(1H, m), 3.03-3.15 (2H, m), 4.31-4.48(4H, m), 4.58 (2H, t), 6.73(1H, d), 6.84(2H, d), 7.18(2H, d), 7.65(1H, d), 8.02(1H, d) and 8.23(1H, d). | 527 |

Example 45

Preparation of 4-{4-[2-(4-acetylpiperazin-1-yl)ethoxy]phenyl}-1-[3-(trifluoromethyl)-7,8-dihydro[1,2,4]triazolo[4,3-b]pyridazin-6-yl]piperidin-4-ol

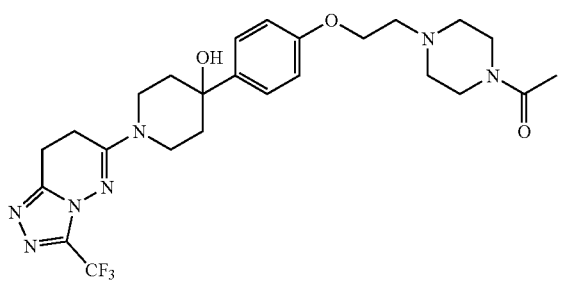

Obtained in 21% yield by an analogous method to Example 4.2, starting from 4-[4-[2-(4-acetylpiperazin-1-yl)ethoxy]phenyl]-1-[3-(trifluoromethyl)[1,2,4]triazolo[4,3-b]pyridazin-6-yl]piperidin-4-ol.

1H NMR (399.902 MHz, DMSO-d6) δ 1.66 (2H, d), 1.89-2.05 (5H, m), 2.43 (2H, t), 2.73 (2H, t), 2.2.95 (2H, t), 3.18 (2H, t), 3.42 (4H, t), 4.09 (4H, t), 5.08 (1H, s), 1H, s), 6.89 (2H, d) and 7.38 (1H, d). m/z=537 [M+H]+.

The 4-[4-[2-(4-acetylpiperazin-1-yl)ethoxy]phenyl]-1-[3-(trifluoromethyl)[1,2,4]triazolo[4,3-b]pyridazin-6-yl]piperidin-4-ol used as starting material was obtained in 55% yield by an analogous method to Example 36, preparation of starting materials, starting from 4-(4-hydroxyphenyl)-1-[3-(trifluoromethyl)[1,2,4]triazolo[4,3-b]pyridazin-6-yl]piperidin-4-ol and 2-(4-acetylpiperazine-1-yl)ethanol (obtained as described in PCT Int. Appl. WO2003064413, Example 28, preparation of starting materials).

1H NMR (499.8 MHz, DMSO-d6, spectrum recorded at 100° C.) δ 1.79 (2H, d), 1.97-2.07 (8H, m), 2.75 (2H, t), 3.39-3.48 (7H, m), 4.08-4.16 (4H, m), 6.89 (2H, d), 7.41 (2H, d), 7.55 (1H, d), 8.12 (1H, d); m/z=534 [M+H]+.

Example 46

Preparation of 1-ethyl-4-[2-(4-{1-[3-(trifluoromethyl)-7,8-dihydro[1,2,4]triazolo[4,3-b]pyridazin-6-yl]piperidin-4-yl}phenoxy)ethyl]piperazin-2-one

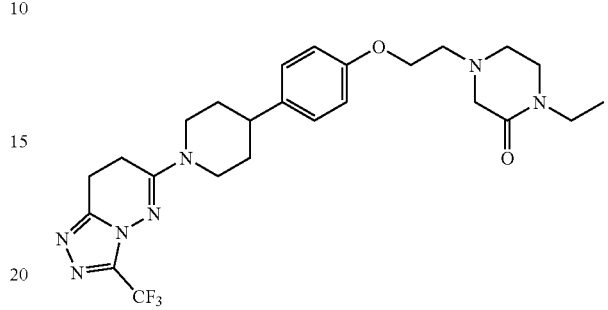

DIPEA (0.219 mL, 1.23 mmol) was added to 2-(4-{1-[3-(trifluoromethyl)-7,8-dihydro[1,2,4]triazolo[4,3-b]pyridazin-6-yl]piperidin-4-yl}phenoxy)ethyl methanesulfonate (200 mg, 0.41 mmol) and 1-ethylpiperazin-2-one (52.6 mg, 0.41 mmol) in DMF (5 mL) at 20° C. under nitrogen. The resulting solution was stirred at 110° C. for 3 hours and the solvent was removed in vacuo to give an orange gum, which was dissolved in DCM (100 mL) and the solution washed with water (100 mL). The organic layer was passed through a phase separating cartridge and then evaporated to dryness to give an orange gum. The crude product was purified by flash silica chromatography, elution gradient 0 to 10% EtOAc in isohexane then 10% methanolic ammonia in EtOAc. Pure fractions were evaporated to dryness to afford a yellow gum, which was triturated with ether to give 1-ethyl-4-[2-(4-{1-[3-(trifluoromethyl)-7,8-dihydro[1,2,4]triazolo[4,3-b]pyridazin-6-yl]piperidin-4-yl}phenoxy)ethyl]piperazin-2-one (77 mg, 36.1%) as a white solid.

1H NMR (399.9 MHz, DMSO-d6) δ 1.03 (3H, t), 1.55-1.69 (2H, m), 1.80 (2H, d), 2.70-2.84 (5H, m), 2.90-3.05 (4H, m), 3.13 (2H, t), 3.23-3.33 (6H, m), 4.08 (2H, t), 4.29 (2H, m), 6.88 (2H, d) and 7.17 (2H, d); m/z=m/z=521 [M+H]+.

The 2-(4-{1-[3-(trifluoromethyl)-7,8-dihydro[1,2,4]triazolo[4,3-b]pyridazin-6-yl]piperidin-4-yl}phenoxy)ethyl methanesulfonate used as starting material was prepared as follows:—

Preparation of 4-{1-[3-(trifluoromethyl)-7,8-dihydro[1,2,4]triazolo[4,3-b]pyridazin-6-yl]piperidin-4-yl}phenol 4-{1-[3-(Trifluoromethyl)[1,2,4]triazolo[4,3-b]pyridazin-6-yl]piperidin-4-yl}phenol (obtained as described in Example 5.2, preparation of starting materials) (30 g, 82.57 mmol) and 5% Pd on carbon (50% wet, JM Type 87L) (35.1 g, 8.26 mmol) in MeOH (50 mL) were stirred under an atmosphere of hydrogen at 5 bar and 50° C. for 5 days. The mixture was cooled to room temperature and the catalyst removed by filtration. The solvent was evaporated to give 4-{1-[3-(trifluoromethyl)-7,8-dihydro[1,2,4]triazolo[4,3-b]pyridazin-6-yl]piperidin-4-yl}phenol (20.54 g, 68%).

1H NMR (399.9 MHz, DMSO-d6) δ 1.58 (2H, m), 1.80 (2H, m), 2.71 (1H, m), 2.91-3.01 (4H, m), 3.15 (2H, t), 4.27 (2H, m), 6.69 (2H, d), 7.04 (2H, d), 9.19 (1H, s); m/z=366 [M+H]+.

Preparation of 2-(4-{1-[3-(trifluoromethyl)-7,8-dihydro[1,2,4]triazolo[4,3-b]pyridazin-6-yl]piperidin-4-yl}phenoxy)ethanol 1,3-Dioxolan-2-one (1093 mg, 12.41 mmol) was added to 4-{1-[3-(trifluoromethyl)-7,8-dihydro[1,2,4]triazolo[4,3-b]pyridazin-6-yl]piperidin-4-yl}phenol (907 mg, 2.48 mmol) and potassium carbonate (686 mg, 4.97 mmol) in DMF (10 mL). The resulting mixture was stirred at 80° C. for 16 hours. The reaction mixture was evaporated to dryness, the residue redissolved in DCM (100 mL) and the solution washed with water (100 mL). The aqueous washings were re-extracted with DCM (100 mL), then the combined organic phases were washed with saturated brine (50 mL), dried over MgSO4, filtered and evaporated to afford crude product. The crude product was purified by flash silica chromatography, elution gradient 0 to 2% MeOH in EtOAc. Pure fractions were evaporated to dryness to afford 2-(4-{1-[3-(trifluoromethyl)-7,8-dihydro[1,2,4]triazolo[4,3-b]pyridazin-6-yl]piperidin-4-yl}phenoxy)ethanol (695 mg, 68%).

1H NMR (399.9 MHz, DMSO-d6) δ 1.61 (2H, m), 1.82 (2H, m), 2.77 (1H, m), 2.90-3.03 (4H, m), 3.16 (2H, t), 3.70 (2H, m), 3.95 (2H, t), 4.29 (2H, m), 4.85 (1H, t), 6.87 (2H, d), 7.16 (2H, d); m/z=410 [M+H]+.

Preparation of 2-(4-{1-[3-(trifluoromethyl)-7,8-dihydro[1,2,4]triazolo[4,3-b]pyridazin-6-yl]piperidin-4-yl}phenoxy)ethyl methanesulfonate A solution of methanesulfonyl chloride (0.158 mL, 2.04 mmol) in DCM (1 mL) was added dropwise to a stirred solution of 2-(4-{1-[3-(trifluoromethyl)-7,8-dihydro[1,2,4]triazolo[4,3-b]pyridazin-6-yl]piperidin-4-yl}phenoxy)ethanol (695 mg, 1.70 mmol) and triethylamine (0.473 mL, 3.40 mmol) in DCM (7 mL) cooled to 0° C. under nitrogen. The resulting solution was stirred at 0° C. for 15 minutes, then warmed to room temperature and stirred for a further 15 minutes. The reaction mixture was diluted with DCM (50 mL), and washed with water (50 mL) and saturated brine (25 mL). The organic layer was dried over MgSO4, filtered and evaporated to afford 2-(4-{1-[3-(trifluoromethyl)-7,8-dihydro[1,2,4]triazolo[4,3-b]pyridazin-6-yl]piperidin-4-yl}phenoxy)ethyl methanesulfonate (796 mg, 96%).

1H NMR (399.9 MHz, DMSO-d6) δ 1.62 (2H, m), 1.82 (2H, m), 2.79 (1H, m), 2.92-3.03 (4H, m), 3.16 (2H, t), 3.24 (3H, s), 4.22-4.33 (4H, m), 4.52 (2H, m), 6.92 (2H, d), 7.19 (2H, d); m/z=488 [M+H]+.

Examples 47-50

The following compounds were prepared in 35-60% yield by an analogous method to Example 46, starting from 2-(4-{1-[3-(trifluoromethyl)-7,8-dihydro[1,2,4]triazolo[4,3-b]pyridazin-6-yl]piperidin-4-yl}phenoxy)ethyl methanesulfonate and the appropriate is amine:—

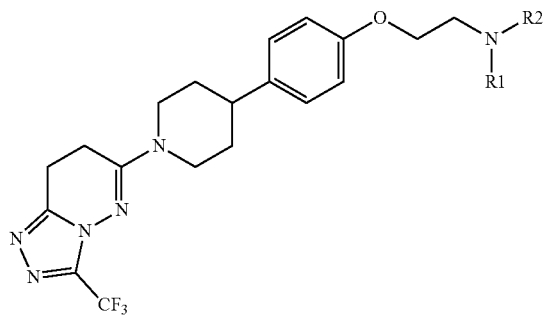

| Ex. | NR1R2 | 1H NMR(399 MHz, DMSO-d6) | m/z [M + H]+ |
|---|---|---|---|
| 47 | (piperazinone with N-cyclopropyl) | δ 0.57-0.73(4H, m), 1.55-1.69(2H, m), 1.81 (2H, d), 2.66-2.84(6H, m), 2.88-3.06(4H, m), 3.10(2H, s), 3.12-3.22(4H, m), 4.07(2H, t), 4.28(2H, d), 6.88(2H, d), 7.15(2H, d). | 533 |
| 48 | (N-acetyl diazepane) | δ 1.54-1.89(6H, m), 1.98(3H, s), 2.63-3.07 (11H, m), 3.17(2H, t), 3.40-3.55(4H, m), 3.98-4.07(2H, m), 4.27(2H, d), 6.87(2H, d), 7.15 (2H, d). | 535 |
| 49 | (methyl-substituted piperazinone) | δ 1.24(3H, d), 1.55-1.68(2H, m), 1.81(2H, d), 2.64-2.84(6H, m), 2.88-3.10(6H, m), 3.15(2H, t), 3.20-3.31(3H, m), 4.06(2H, t), 4.28(2H, d), 6.88(2H, d), 7.18(2H, d). | 521 |

-continued

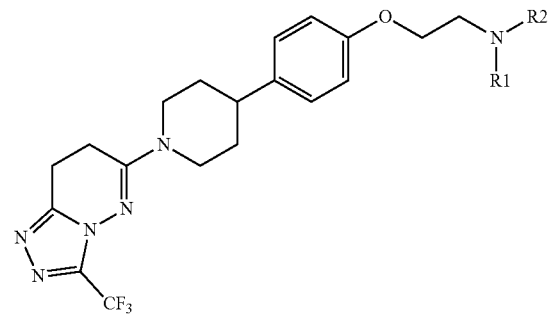

| Ex. | NR1R2 | 1H NMR(399 MHz, DMSO-d6) | m/z [M + H]+ |
|---|---|---|---|
| 50 | (piperazinone with HN, methyl, N-methyl, C=O) | δ 1.24(3H, d), 1.55-1.68(2H, m), 1.81(2H, d), 2.64-2.84(6H, m), 2.88-3.10(6H, m), 3.15(2H, t), 3.20-3.31(3H, m), 4.06(2H, t), 4.28(2H, d), 6.88(2H, d), 7.18(2H, d). | 521 |

Example 51

Preparation of 6-[4-(4-{2-[(3R)-4-acetyl-3-methylpiperazin-1-yl]ethoxy}phenyl)piperidin-1-yl]-3-(trifluoromethyl)-7,8-dihydro[1,2,4]triazolo[4,3-b]pyridazine

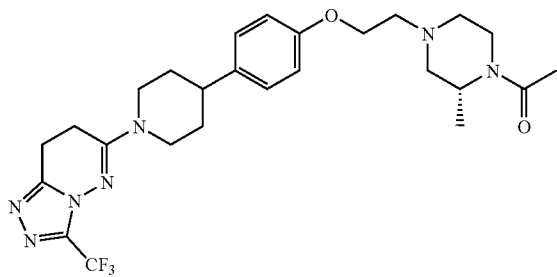

Methanesulfonyl chloride (0.165 mL, 2.12 mmol) was added dropwise to (R)-2-(4-acetyl-3-methylpiperazin-1-yl)ethanol (360 mg, 1.94 mmol) and triethylamine (0.404 mL, 2.90 mmol) in DCM (5 mL) at 0° C. under nitrogen. The resulting solution was stirred at 0° C. for 15 minutes, warmed to room temperature and stirred for 2 hours. The reaction mixture was diluted with DCM (50 mL) and washed with water (15 mL). The organic layer was passed through a phase separating cartridge and concentrated in vacuo. The residual orange gum was dissolved in DMF (5 mL) and added to 4-{1-[3-(trifluoromethyl)-7,8-dihydro[1,2,4]triazolo[4,3-b]pyridazin-6-yl]piperidin-4-yl}phenol (obtained as described in Example 46, preparation of starting materials) (235 mg, 0.64 mmol) and potassium carbonate (445 mg, 3.22 mmol) in DMF (10 mL) at 20° C. under nitrogen. The resulting suspension was stirred at 100° C. for 3 hours and the solvent was removed in vacuo. The residue was partitioned between DCM (100 mL) and water (100 mL) and the organic phase was separated. The aqueous phase was re-extracted with DCM (100 mL), and the is combined organic phases were washed with brine (100 mL), passed through phase separating cartridge and concentrated under reduced pressure to give an orange gum. The crude product was purified by flash silica chromatography, elution gradient 0 to 10% MeOH in EtOAc. Pure fractions were evaporated to dryness to afford a pale yellow gum, which was triturated with ether to give 6-[4-(4-{2-[(3R)-4-acetyl-3-methylpiperazin-1-yl]ethoxy}phenyl)piperidin-1-yl]-3-(trifluoromethyl)-7,8-dihydro[1,2,4]triazolo[4,3-b]pyridazine (101 mg, 29.4%) as a white solid.

1H NMR (499.8 MHz, DMSO-d6) δ 1.18 (3H, d), 1.59-1.69 (2H, m), 1.87 (2H, d), 1.97 (3H, s), 2.01-2.08 (1H, m), 2.18-2.24 (1H, m), 2.61-2.83 (4H, m), 2.85-2.98 (6H, m), 3.04 (2H, t), 3.14 (2H, t), 4.08 (2H, t), 4.26 (2H, d), 6.88 (2H, d), 7.15 (2H, d); m/z=535 [M+H]+.

The (R)-2-(4-acetyl-3-methylpiperazin-1-yl)ethanol used as starting material was prepared as follows:—

2-Bromoethanol (7.34 mL, 103.38 mmol) was added to a stirred mixture of (R)-1-acetyl-2-methylpiperazine (2.94 g, 20.68 mmol) and potassium carbonate (8.57 g, 62.03 mmol) in THF (75 mL). The resulting mixture was stirred at 80° C. for 18 hours before, then filtered and evaporated. The residue was purified by ion exchange chromatography, using an SCX column and eluting with 2M ammonia in methanol. Pure fractions were evaporated to dryness to give (R)-2-(4-acetyl-3-methylpiperazin-1-yl)ethanol (3.74 g, 97%) as a yellow oil.

1H NMR (400.1 MHz, CDCl3) δ 1.30 (3H, d), 1.63 (1H, s), 2.06-2.12 (3H, m), 2.12-2.89 (6H, m), 2.89-3.47 (1H, m), 3.51-4.84 (2H, m), 3.60-3.67 (2H, m)

Example 52

Preparation of 6-[4-(4-{2-[(3S)-4-acetyl-3-methylpiperazin-1-yl]ethoxy}phenyl)piperidin-1-yl]-3-(trifluoromethyl)-7,8-dihydro[1,2,4]triazolo[4,3-b]pyridazine

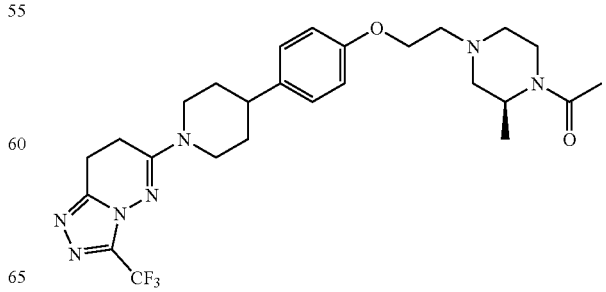

Obtained in 41% yield by an analogous method to Example 51, starting from 4-{1-[3-(trifluoromethyl)-7,8-dihydro[1,2,4]triazolo[4,3-b]pyridazin-6-yl]piperidin-4-yl}phenol and (S)-2-(4-acetyl-3-methylpiperazin-1-yl)ethanol (obtained by an analogous method to the R enantiomer as described in Example 51, preparation of starting materials).

1H NMR (499.8 MHz, DMSO-d6) δ 1.18 (3H, d), 1.59-1.69 (2H, m), 1.87 (2H, d), 1.97 (3H, s), 2.01-2.08 (1H, m), 2.18-2.24 (1H, m), 2.61-2.83 (4H, m), 2.85-2.98 (6H, m), 3.04 (2H, t), 3.14 (2H, t), 4.08 (2H, t), 4.26 (2H, d), 6.88 (2H, d), 7.15 (2H, d); m/z=535 [M+H]+.

Examples 53 and 54

Preparation of (R)-6-(4-{4-[2-(4-acetylpiperazin-1-yl)propoxyl]phenyl}piperidin-1-yl)-3-(trifluoromethyl)-7,8-dihydro[1,2,4]triazolo[4,3-b]pyridazine and (S)-6-(4-{4-[2-(4-acetylpiperazin-1-yl)propoxy]phenyl}piperidin-1-yl)-3-(trifluoromethyl)-7,8-dihydro[1,2,4]triazolo[4,3-b]pyridazine

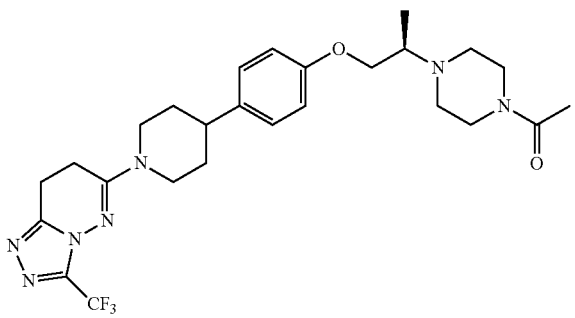

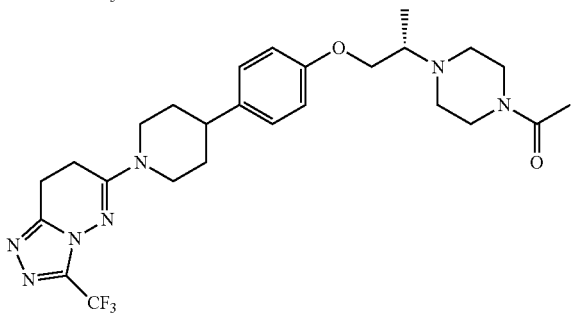

Acetic acid (0.081 mL, 1.41 mmol) was added to 1-(4-{1-[3-(trifluoromethyl)-7,8-dihydro[1,2,4]triazolo[4,3-b]pyridazin-6-yl]piperidin-4-yl}phenoxy)propan-2-one (595 mg, 1.41 mmol), N-acetylpiperazine (199 mg, 1.55 mmol) and a catalytic amount of MgSO4 in THF (5 mL). The resulting mixture was stirred at ambient temperature for 1 hour, then sodium triacetoxyborohydride (359 mg, 1.69 mmol) was added and stirring was continued for a further 16 hours. The reaction mixture was concentrated, diluted with DCM (25 mL), washed with saturated NaHCO3 (25 mL) and then filtered through a PTFE cup. The organic layer was evaporated to afford crude product. The crude product was purified by flash silica chromatography, elution gradient 0 to 5% MeOH in DCM. Pure fractions were evaporated to dryness to afford racemic 6-(4-{4-[2-(4-acetylpiperazin-1-yl)propoxy]phenyl}piperidin-1-yl)-3-(trifluoromethyl)-7,8-dihydro[1,2,4]triazolo[4,3-b]pyridazine (199 mg, 26.4%) as a gum.

The racemic material was purified by preparative chiral-HPLC on a Merck 50 mm 20 μm Chiralcel OD column, eluting isocratically with 30% MeOH/EtOH in isohexanes. The fractions containing the desired compounds were evaporated to dryness to afford 6-(4-{4-[2-(4-acetylpiperazin-1-yl)propoxy]phenyl}piperidin-1-yl)-3-(trifluoromethyl)-7,8-dihydro[1,2,4]triazolo[4,3-b]pyridazine (first eluting enantiomer) (91 mg) as a solid.

1H NMR (399.9 MHz, DMSO-d6) δ 1.07 (3H, d), 1.55-1.66 (2H, m), 1.81 (2H, d), 1.98 (3H, s), 2.53-2.63 (4H, m), 2.74-2.80 (1H, m), 2.92-3.03 (5H, m), 3.16 (2H, t), 3.37-3.42 (4H, m), 3.82-3.86 (1H, m), 4.00-4.04 (1H, m), 4.29 (2H, br s), 6.86-6.90 (2H, m), 7.16 (2H, d); m/z=534 [M+H]+.

Further elution from the chiral chromatography column gave the second eluting enantiomer of 6-(4-{4-[2-(4-acetylpiperazin-1-yl)propoxy]phenyl}piperidin-1-yl)-3-(trifluoromethyl)-7,8-dihydro[1,2,4]triazolo[4,3-b]pyridazine (97 mg).

1H NMR (399.9 MHz, DMSO-d6) δ 1.07 (3H, d), 1.55-1.66 (2H, m), 1.81 (2H, d), 1.98 (3H, s), 2.53-2.63 (4H, m), 2.74-2.80 (1H, m), 2.92-3.03 (5H, m), 3.16 (2H, t), 3.37-3.42 (4H, m), 3.82-3.86 (1H, m), 4.00-4.04 (1H, m), 4.29 (2H, br s), 6.86-6.90 (2H, m), 7.16 (2H, d); m/z=534 [M+H]+.

The 1-(4-{1-[3-(trifluoromethyl)-7,8-dihydro[1,2,4]triazolo[4,3-b]pyridazin-6-yl]piperidin-4-yl}phenoxy)propan-2-one used as starting material was prepared as follows:—

Potassium carbonate (1.214 g, 8.79 mmol) was added to 4-{1-[3-(trifluoromethyl)-7,8-dihydro[1,2,4]triazolo[4,3-b]pyridazin-6-yl]piperidin-4-yl}phenol (obtained as described in Example 46, preparation of starting materials) (1.07 g, 2.93 mmol) and 1-chloropropan-2-one (0.466 mL, 5.86 mmol) in DMA (10 mL). The resulting mixture was stirred at 100° C. for 2 hours. The reaction mixture was cooled to room temperature, concentrated and diluted with water (25 mL) then extracted with DCM (2×25 mL). The organic layer was dried over MgSO4, filtered and evaporated to afford crude product. The crude product was purified by flash silica chromatography, elution gradient 50 to 100% EtOAc in isohexane. Pure fractions were evaporated to dryness to afford 1-(4-{1-[3-(trifluoromethyl)-7,8-dihydro[1,2,4]triazolo[4,3-b]pyridazin-6-yl]piperidin-4-yl}phenoxy)propan-2-one (1.190 g, 96%) as a gum.

1H NMR (399.9 MHz, CDCl3) δ 1.61 (2H, m), 1.88 (2H, m), 2.20 (3H, s), 2.65-2.74 (3H, m), 2.94 (2H, m), 3.15 (2H, t), 4.25 (2H, m), 4.45 (2H, s), 6.77 (2H, d), 7.07 (2H, d); m/z=422 [M+H]+.

Example 55.1

Preparation of (S)-1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one

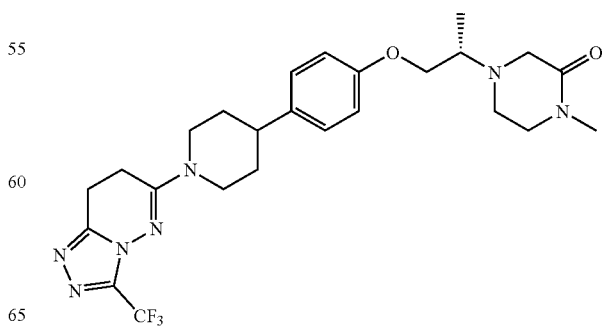

Racemic 1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one was obtained in 18% yield by an analogous procedure to Example 53, starting from 1-(4-{1-[3-(trifluoromethyl)-7,8-dihydro[1,2,4]triazolo[4,3-b]pyridazin-6-yl]piperidin-4-yl}phenoxy)propan-2-one and 1-methylpiperazin-2-one.

The racemic material was purified by preparative chiral-HPLC on a Merck 50 mm 20 μm Chiralpak AS column, eluting isocratically with MeOH. The fractions containing the desired compounds were evaporated to dryness to afford (S)-1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one (first eluting enantiomer, 65% recovery from racemate) as a solid, which was shown by chiral hplc to correspond to the enantiomer obtained by chiral synthesis in Example 55.2.

$^1$H NMR (399.9 MHz, DMSO-d6) δ 1.07 (3H, d), 1.61 (2H, dt), 1.81 (2H, d), 2.72-2.84 (6H, m), 2.89-3.07 (5H, m), 3.15 (2H, d), 3.19 (2H, d), 3.20-3.25 (2H, m), 3.87 (1H, dd), 4.02 (1H, dd), 4.29 (2H, s), 6.89 (2H, d), 7.16 (2H, d); m/z=520 [M+H]+.

Example 55.2

Preparation of (S)-1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one

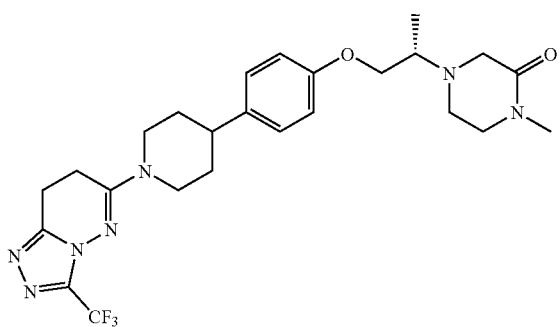

Palladium (8.22 mg, 0.08 mmol) was added to (S)-1-methyl-4-[1-methyl-2-(4-{1-[3-(trifluoromethyl)[1,2,4]triazolo[4,3-b]pyridazin-6-yl]piperidin-4-yl}phenoxy)ethyl]piperazin-2-one (0.040 g, 0.08 mmol) and ammonium formate (0.146 g, 2.32 mmol) in ethanol (5 mL) at 20° C. The resulting suspension was stirred at 78° C. for 24 hours. The catalyst was filtered off through a pad of diatomaceous earth and the filtrate was concentrated under reduced pressure to give a yellow gum. The crude product was purified by flash silica chromatography, elution gradient 0 to 10% MeOH in DCM. Pure fractions were evaporated to dryness to afford (S)-1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one (0.018 g, 44.8%), which was shown by chiral hplc to correspond to the first eluting isomer obtained in Example 55.1.

$^1$H NMR (399.9 MHz, DMSO-d6) δ 1.07 (3H, d), 1.61 (2H, dt), 1.81 (2H, d), 2.72-2.84 (6H, m), 2.89-3.07 (5H, m), 3.15 (2H, d), 3.19 (2H, d), 3.20-3.25 (2H, m), 3.87 (1H, dd), 4.02 (1H, dd), 4.29 (2H, s), 6.89 (2H, d), 7.16 (2H, d); m/z=520 [M+H]+.

The (S)-1-methyl-4-[1-methyl-2-(4-{1-[3-(trifluoromethyl)[1,2,4]triazolo[4,3-b]pyridazin-6-yl]piperidin-4-yl}phenoxy)ethyl]piperazin-2-one used as starting material was prepared as follows:—

DIAD (1.639 ml, 8.32 mmol) was added to a solution of 4-{1-[3-(trifluoromethyl)[1,2,4]triazolo[4,3-b]pyridazin-6-yl]piperidin-4-yl}phenol (obtained as described in Example 5.2, preparation of starting materials) (2.16 g, 5.94 mmol), (S)-tert-butyl 1-hydroxypropan-2-ylcarbamate (1.458 g, 8.32 mmol) and triphenylphosphine (2.183 g, 8.32 mmol) in THF (21.60 ml) at 0° C. The mixture was stirred at room temperature for 4 days. Further portions of (S)-tert-butyl 1-hydroxypropan-2-ylcarbamate (1.042 g, 5.94 mmol), triphenylphosphine (1.559 g, 5.94 mmol) and DIAD (1.171 ml, 5.94 mmol) were added and the mixture was stirred for a further 24 hours. Further portions of (S)-tert-butyl 1-hydroxypropan-2-ylcarbamate (1.042 g, 5.94 mmol), triphenylphosphine (1.559 g, 5.94 mmol) and DIAD (1.171 ml, 5.94 mmol) were added and the mixture was stirred for 3 days. The reaction mixture was diluted with EtOAc (43.2 ml, 20 vol), washed with 50% saturated brine (2×21.60 ml), dried over MgSO$_4$, filtered and concentrated in vacuo to give a dark oil that crystallised on standing. 4 M HCl in dioxane (14.84 ml, 59.36 mmol) was added and the mixture was stirred at room temperature for 5 days. The solid precipitate was collected by filtration, washed with dioxane and water, and dried under air. A 200 mg aliquot was dissolved in DMF (2.5 mL) containing DIPEA (0.708 mL, 4.05 mmol) and a solution of 2-chloro-N-(2-chloroethyl)-N-methylacetamide (obtained as described in J Chem Soc, 1949, 550) (0.224 g, 1.32 mmol) in DMF (2.5 mL) was added. The mixture was stirred at room temperature for 1.5 hours then heated to 60° C. for 24 hours. The mixture was evaporated to dryness and partitioned between EtOAc (20 ml) and 2M NaOH (20 ml). The aqueous phase was extracted with a further portion of EtOAc (20 mL). The combined were organics washed with 50% saturated brine and saturated brine, dried over MgSO$_4$, filtered and concentrated in vacuo. The crude product was purified by flash silica chromatography, elution gradient 0 to 10% MeOH in DCM. Fractions containing the product were evaporated to dryness to afford a brown gum. The product was purified by ion exchange chromatography, using an SCX column. The desired product was eluted from the column using 7M ammonia in methanol, and pure fractions were evaporated to dryness to afford (S)-1-methyl-4-[1-methyl-2-(4-{1-[3-(trifluoromethyl)[1,2,4]triazolo[4,3-b]pyridazin-6-yl]piperidin-4-yl}phenoxy)ethyl]piperazin-2-one (0.042 g) as a brown gum.

$^1$H NMR (499.8 MHz, DMSO-d6) δ 1.08 (3H, d), 1.64-1.72 (2H, m), 1.88 (2H, d), 2.78-2.84 (6H, m), 3.01 (1H, q), 3.07-3.14 (2H, m), 3.18-3.24 (4H, m), 3.85-3.89 (1H, m), 4.00-4.04 (1H, m), 4.41 (2H, d), 6.87-6.90 (2H, m), 7.18 (2H, s), 7.66 (1H, d), 8.24 (1H, d); m/z=518 [M+H]+.

Example 56

Preparation of (R) 1-methyl-4-[1-methyl-2-(4-{1-[3-(trifluoromethyl)-7,8-dihydro[1,2,4]triazolo[4,3-b]pyridazin-6-yl]piperidin-4-yl}phenoxy)ethyl]piperazin-2-one

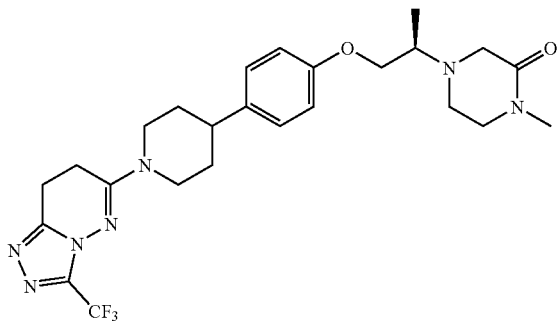

Obtained in 62% recovery from the racemate by further elution from the chiral chromatography column used in Example 55.1 and assigned R stereochemistry by inference from Example 55.2.

$^1$H NMR (399.9 MHz, DMSO-d6) δ 1.07 (3H, d), 1.61 (2H, dt), 1.81 (2H, d), 2.72-2.84 (6H, m), 2.89-3.07 (5H, m), 3.15 (2H, d), 3.19 (2H, d), 3.20-3.25 (2H, m), 3.87 (1H, dd), 4.02 (1H, dd), 4.29 (2H, s), 6.89 (2H, d), 7.16 (2H, d); m/z=520 [M+H]+.

LIST OF FIGURES

Figure A: X-Ray Powder Diffraction Pattern for 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A when measured using CuKa radiation.

Figure B: X-Ray Powder Diffraction Pattern for 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate when measured using CuKa radiation.

Figure C: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A when measured using CuKa radiation and the crystalline material is in the preferred orientation.

Figure D: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate when measured using CuKa radiation.

Figure E: DSC Thermogram of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A.

Figure F: DSC Thermogram of 6-[4-[4-[3-(4-acetylpiperazin-1-yl)propoxy]phenyl]piperidin-1-yl]-3-(trifluoromethyl)-7,8-dihydro[1,2,4]triazolo[4,3-b]pyridazine Form A ethylacetate solvate.

Figure G: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A when the crystalline material is in the preferred orientation.

Figure H: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A hydrate.

Figure I: Alternative X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A when measured using CuKa radiation, obtained from an alternative crystal morphology.

Figure J: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A, obtained from an alternative morphology of the Form A crystalline material.

Figure K: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate when measured using CuKa radiation.

Figure L: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine napadisylate.

Figure M: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate when measured using CuKa radiation.

Figure N: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine di-tosylate.

Figure O: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate when measured using CuKa radiation.

Figure P: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate.

Figure Q: X-Ray Powder Diffraction Pattern for 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate when measured using CuKa radiation.

Figure R: DSC Thermogram of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine fumarate.

The invention claimed is:

1. A compound which is 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof.

2. A compound according to claim 1 which is 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine.

3. A compound according to claim 2 which is 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine Form A.

4. A compound according to claim 1 which is 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine maleate.

5. A pharmaceutical composition comprising:
   a. 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof; and
   b. a pharmaceutically acceptable diluent or carrier.

6. A method for treating prostate cancer which comprises administering to a warm-blooded animal in need thereof a therapeutically effective amount of 6-(4-{4-[2-(4-acetylpiperazin-1-yl)ethoxy]phenyl}piperidin-1-yl)-3-(trifluoromethyl)-7,8-dihydro[1,2,4]triazolo[4,3-b]pyridazine or a pharmaceutically acceptable salt thereof.

7. The method of claim 6, wherein said warm-blooded animal is a human.

8. The method of claim 6, wherein said prostate cancer is castrate-resistant prostate cancer.

* * * * *